US008003097B2

(12) United States Patent
Schroeter et al.

(10) Patent No.: US 8,003,097 B2
(45) Date of Patent: *Aug. 23, 2011

(54) TREATMENT OF CEREBRAL AMYLOID ANGIOPATHY

(75) Inventors: Sally Schroeter, Belmont, CA (US); Kate Dora Games, Belmont, CA (US); Wagner Zago, San Mateo, CA (US)

(73) Assignees: Janssen Alzheimer Immunotherapy, County Cork (IE); Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/181,238

(22) Filed: Jul. 28, 2008

(65) Prior Publication Data

US 2009/0142270 A1    Jun. 4, 2009

Related U.S. Application Data

(63) Continuation-in-part of application No. 12/106,206, filed on Apr. 18, 2008.

(60) Provisional application No. 60/925,228, filed on Apr. 18, 2007.

(51) Int. Cl.
  *A61K 39/395* (2006.01)
(52) U.S. Cl. .................. 424/133.1; 424/139.1
(58) Field of Classification Search ............ None
  See application file for complete search history.

(56) References Cited

U.S. PATENT DOCUMENTS

| | | | |
|---|---|---|---|
| 4,666,829 A | 5/1987 | Glenner et al. |
| 4,713,366 A | 12/1987 | Stevens |
| 4,816,397 A | 3/1989 | Boss et al. |
| 4,816,567 A | 3/1989 | Cabilly et al. |
| 4,879,213 A | 11/1989 | Fox et al. |
| 4,883,666 A | 11/1989 | Sabel et al. |
| 4,912,206 A | 3/1990 | Goldgaber et al. |
| 5,004,697 A | 4/1991 | Pardridge |
| 5,057,540 A | 10/1991 | Kensil et al. |
| 5,096,706 A | 3/1992 | Flint |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,225,539 A | 7/1993 | Winter |
| 5,227,159 A | 7/1993 | Miller |
| 5,231,000 A | 7/1993 | Majocha et al. |
| 5,231,170 A | 7/1993 | Averback |
| 5,245,015 A | 9/1993 | Fung et al. |
| 5,258,498 A | 11/1993 | Huston et al. |
| 5,262,332 A | 11/1993 | Selkoe |
| 5,270,165 A | 12/1993 | Van Nostrand et al. |
| 5,278,049 A | 1/1994 | Baker et al. |
| 5,358,708 A | 10/1994 | Patel |
| 5,385,887 A | 1/1995 | Yim et al. |
| 5,387,742 A | 2/1995 | Cordell |
| 5,417,986 A | 5/1995 | Reid et al. |
| 5,434,170 A | 7/1995 | Andrulis, Jr. |
| 5,441,870 A | 8/1995 | Seubert et al. |
| 5,464,823 A | 11/1995 | Lehrer et al. |
| 5,470,951 A | 11/1995 | Roberts |
| 5,472,693 A | 12/1995 | Gourlie et al. |
| 5,514,548 A | 5/1996 | Krebber et al. |
| 5,530,101 A | 6/1996 | Queen et al. |
| 5,571,499 A | 11/1996 | Hafler et al. |
| 5,571,500 A | 11/1996 | Hafler et al. |
| 5,576,184 A | 11/1996 | Better et al. |
| 5,583,112 A | 12/1996 | Kensil et al. |
| 5,585,089 A | 12/1996 | Queen et al. |
| 5,585,100 A | 12/1996 | Mond et al. |
| 5,589,154 A | 12/1996 | Anderson |
| 5,593,846 A | 1/1997 | Schenk et al. |
| 5,601,827 A | 2/1997 | Collier et al. |
| 5,605,811 A | 2/1997 | Seubert et al. |
| 5,612,486 A | 3/1997 | McConlogue et al. |
| 5,618,920 A | 4/1997 | Robinson et al. |
| 5,620,844 A | 4/1997 | Neurath et al. |
| 5,622,701 A | 4/1997 | Berg |
| 5,624,821 A | 4/1997 | Winter et al. |
| 5,624,937 A | 4/1997 | Reel et al. |
| 5,641,473 A | 6/1997 | Hafler et al. |
| 5,641,474 A | 6/1997 | Hafler et al. |
| 5,645,820 A | 7/1997 | Hafler et al. |
| 5,648,260 A | 7/1997 | Winter et al. |
| 5,652,334 A | 7/1997 | Roberts |
| 5,677,425 A | 10/1997 | Bodmer et al. |

(Continued)

FOREIGN PATENT DOCUMENTS

AU    707083    7/1999

(Continued)

OTHER PUBLICATIONS

Prada 2007 (Journal of Neuroscience 27(8):1973-1980).*
Bard 2003 (Proc Natl Acad Sci USA 100(4):2023-2028).*
Pangalos 2005 (Biochemical Society Transactions 33(4):553-558).*
Racke et al 2005 (Journal of Neuroscience 25:629-636).*
Pfeifer 2002 (Science 298:1379).*
U.S. Appl. No. 09/201,430, Notice of Allowance mailed Mar. 26, 2003.
U.S. Appl. No. 09/201,430, Notice of Allowance mailed Sep. 23, 2003.

(Continued)

*Primary Examiner* — Daniel E. Kolker
(74) *Attorney, Agent, or Firm* — Rosemarie L. Celli; Alston + Bird LLP

(57) ABSTRACT

The invention provides improved agents and methods for treatment of cerebral amyloid angiopathy (CAA) and methods to effect prophylaxis of CAA. The methods can treat CAA concurrently with Alzheimer's disease or separately. The methods can effect prophylaxis of CAA concurrently with Alzheimer's disease or separately. The methods involve administering antibody that is specific for the N-terminus of Aβ or an agent that can induce such an antibody.

13 Claims, 10 Drawing Sheets

U.S. PATENT DOCUMENTS

| | | | |
|---|---|---|---|
| 5,679,348 A | 10/1997 | Nesburn et al. |
| 5,688,651 A | 11/1997 | Solomon |
| 5,693,761 A | 12/1997 | Queen et al. |
| 5,693,762 A | 12/1997 | Queen et al. |
| 5,702,906 A | 12/1997 | Rosenthal |
| 5,721,130 A | 2/1998 | Seubert et al. |
| 5,723,130 A | 3/1998 | Hancock et al. |
| 5,731,284 A | 3/1998 | Williams |
| 5,733,547 A | 3/1998 | Weiner et al. |
| 5,733,548 A | 3/1998 | Restifo et al. |
| 5,736,142 A | 4/1998 | Sette et al. |
| 5,744,132 A | 4/1998 | Warne et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,773,007 A | 6/1998 | Penney et al. |
| 5,776,468 A | 7/1998 | Hauser et al. |
| 5,780,587 A | 7/1998 | Potter |
| 5,786,180 A | 7/1998 | Konig et al. |
| 5,798,102 A | 8/1998 | McMichael et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,858,981 A | 1/1999 | Schreiber et al. |
| 5,859,205 A | 1/1999 | Adair et al. |
| 5,866,129 A | 2/1999 | Chang et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,910,427 A | 6/1999 | Mikayama et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 5,994,083 A | 11/1999 | Felici et al. |
| 6,015,662 A | 1/2000 | Hackett, Jr. et al. |
| 6,022,859 A | 2/2000 | Kiessling et al. |
| 6,054,297 A | 4/2000 | Carter et al. |
| 6,057,098 A | 5/2000 | Buechler et al. |
| 6,057,367 A | 5/2000 | Stamler et al. |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,339,068 B1 | 1/2002 | Krieg et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,432,710 B1 | 8/2002 | Boss, Jr. et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,582,945 B1 | 6/2003 | Raso |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,727,349 B1 | 4/2004 | LaRosa et al. |
| 6,743,427 B1 | 6/2004 | Schenk |
| 6,750,324 B1 | 6/2004 | Schenk et al. |
| 6,761,888 B1 | 7/2004 | Schenk |
| 6,787,129 B1 | 9/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk et al. |
| 6,808,712 B2 | 10/2004 | Schenk |
| 6,818,218 B2 | 11/2004 | Schenk |
| 6,824,780 B1 | 11/2004 | Devaux et al. |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 | 7/2005 | Schenk |
| 6,923,964 B1 | 8/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,962,984 B2 | 11/2005 | Ishiwata et al. |
| 6,972,127 B2 | 12/2005 | Schenk |
| 6,982,084 B2 | 1/2006 | Schenk |
| 7,014,855 B2 | 3/2006 | Schenk |
| 7,112,661 B1 | 9/2006 | Miller |
| 7,147,851 B1 | 12/2006 | Ponath et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,575,880 B1 | 8/2009 | Schenk et al. |
| 7,582,733 B2 | 9/2009 | Basi et al. |
| 7,588,766 B1 | 9/2009 | Schenk |
| 7,625,550 B2 | 12/2009 | Basi et al. |
| 7,635,473 B2 | 12/2009 | Warne et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione et al. |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0009104 A1* | 1/2003 | Hyman et al. ............... 600/476 |
| 2003/0039645 A1 | 2/2003 | Adair et al. |
| 2003/0054484 A1 | 3/2003 | Fong et al. |
| 2003/0068316 A1 | 4/2003 | Klein et al. |
| 2003/0068325 A1 | 4/2003 | Wang |
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |

| | | | | | | |
|---|---|---|---|---|---|---|
| 2003/0166558 A1 | 9/2003 | Frangione et al. | | 2009/0155256 A1* | 6/2009 | Black et al. ............... 424/133.1 |
| 2003/0202972 A1 | 10/2003 | James et al. | | 2009/0191231 A1 | 7/2009 | Schenk |
| 2003/0207828 A1 | 11/2003 | Ishiwata et al. | | 2009/0297511 A1 | 12/2009 | Schenk |
| 2004/0043418 A1 | 3/2004 | Holtzman et al. | | 2010/0266505 A1 | 10/2010 | Black |
| 2004/0081657 A1 | 4/2004 | Schenk | | | | |
| 2004/0082762 A1 | 4/2004 | Basi et al. | | FOREIGN PATENT DOCUMENTS | | |
| 2004/0087777 A1 | 5/2004 | Basi et al. | | | | |
| 2004/0171815 A1 | 9/2004 | Schenk et al. | EP | 285 159 A1 | 10/1988 | |
| 2004/0171816 A1 | 9/2004 | Schenk et al. | EP | 0 391 714 A2 | 10/1990 | |
| 2004/0197324 A1 | 10/2004 | Jun et al. | EP | 451 700 A1 | 10/1991 | |
| 2004/0213800 A1 | 10/2004 | Seubert et al. | EP | 276 723 B1 | 12/1993 | |
| 2004/0219146 A1 | 11/2004 | Schenk | EP | 613007 A2 | 2/1994 | |
| 2004/0241164 A1 | 12/2004 | Bales et al. | EP | 616 814 A1 | 3/1994 | |
| 2004/0247590 A1 | 12/2004 | Schenk et al. | EP | 597 101 A1 | 5/1994 | |
| 2004/0247591 A1 | 12/2004 | Schenk et al. | EP | 613 007 A2 | 8/1994 | |
| 2004/0247612 A1 | 12/2004 | Wang | EP | 620 276 A1 | 10/1994 | |
| 2004/0265301 A1 | 12/2004 | Schenk et al. | EP | 626 390 A1 | 11/1994 | |
| 2004/0265308 A1 | 12/2004 | Schenk | EP | 666 080 A1 | 8/1995 | |
| 2004/0265919 A1 | 12/2004 | Vanderstichele et al. | EP | 359 783 B1 | 11/1995 | |
| 2005/0013815 A1 | 1/2005 | Schenk | EP | 683 234 A1 | 11/1995 | |
| 2005/0019328 A1 | 1/2005 | Schenk | EP | 440 619 B1 | 1/1996 | |
| 2005/0019330 A1 | 1/2005 | Schenk | EP | 758 248 B1 | 2/1997 | |
| 2005/0048049 A1 | 3/2005 | Schenk | EP | 758 901 B1 | 2/1997 | |
| 2005/0059591 A1 | 3/2005 | Schenk et al. | EP | 526 511 B1 | 5/1997 | |
| 2005/0059802 A1 | 3/2005 | Schenk et al. | EP | 782 859 A1 | 7/1997 | |
| 2005/0090648 A1* | 4/2005 | Tsurushita et al. ...... 530/388.26 | EP | 783 104 A1 | 7/1997 | |
| 2005/0118651 A1* | 6/2005 | Basi et al. .................... 435/7.2 | EP | 594 607 B1 | 8/1997 | |
| 2005/0123534 A1 | 6/2005 | Adair et al. | EP | 752 886 B1 | 1/1998 | |
| 2005/0123544 A1 | 6/2005 | Schenk et al. | EP | 845 270 A1 | 6/1998 | |
| 2005/0136054 A1 | 6/2005 | Adair et al. | EP | 1 690 547 B1 | 8/1998 | |
| 2005/0142132 A1 | 6/2005 | Schenk et al. | EP | 863 211 A1 | 9/1998 | |
| 2005/0147613 A1 | 7/2005 | Raso | EP | 868 918 A2 | 10/1998 | |
| 2005/0152878 A1 | 7/2005 | Solomon et al. | EP | 652 962 B1 | 12/1998 | |
| 2005/0158304 A1 | 7/2005 | Schenk et al. | EP | 911 036 A2 | 4/1999 | |
| 2005/0163788 A1 | 7/2005 | Schenk | EP | 561 087 B1 | 8/1999 | |
| 2005/0169925 A1 | 8/2005 | Bardroff et al. | EP | 639 081 B1 | 11/1999 | |
| 2005/0191292 A1 | 9/2005 | Schenk | EP | 506 785 B1 | 3/2000 | |
| 2005/0191314 A1 | 9/2005 | Schenk | EP | 1 172 378 A1 | 1/2002 | |
| 2005/0196399 A1 | 9/2005 | Schenk et al. | EP | 1 481 992 A2 | 12/2004 | |
| 2005/0249725 A1 | 11/2005 | Schenk et al. | EP | 1 481 992 A3 | 12/2004 | |
| 2005/0249727 A1 | 11/2005 | Schenk | EP | 921 189 B1 | 1/2005 | |
| 2005/0255122 A1 | 11/2005 | Schenk | EP | 1 033 998 B1 | 10/2005 | |
| 2006/0029611 A1 | 2/2006 | Schenk | EP | 1 185 298 B1 | 6/2009 | |
| 2006/0034858 A1 | 2/2006 | Schenk | GB | 2 220 211 A | 1/1990 | |
| 2006/0057701 A1 | 3/2006 | Rosenthal et al. | GB | 2 335 192 A | 9/1999 | |
| 2006/0099206 A1 | 5/2006 | Sinacore | JP | 62-267297 A | 11/1987 | |
| 2006/0121038 A9 | 6/2006 | Schenk et al. | JP | 07-132033 A | 5/1995 | |
| 2006/0153772 A1 | 7/2006 | Jacobsen | JP | 7-165799 A | 6/1995 | |
| 2006/0160161 A1 | 7/2006 | Pavliakova et al. | WO | WO 87/02671 A | 5/1987 | |
| 2006/0182321 A1 | 8/2006 | Hu et al. | WO | WO 87/06838 A1 | 11/1987 | |
| 2006/0188512 A1 | 8/2006 | Yednock et al. | WO | WO 88/10120 A1 | 12/1988 | |
| 2006/0193850 A1 | 8/2006 | Warne et al. | WO | WO 89/01343 A1 | 2/1989 | |
| 2006/0198851 A1 | 9/2006 | Basi et al. | WO | WO 89/03687 A1 | 5/1989 | |
| 2006/0210557 A1 | 9/2006 | Luisi et al. | WO | WO 89/06242 A1 | 7/1989 | |
| 2006/0234912 A1 | 10/2006 | Wang et al. | WO | WO 89/06689 A1 | 7/1989 | |
| 2006/0240486 A1 | 10/2006 | Johnson-Wood et al. | WO | WO 90/05142 A1 | 5/1990 | |
| 2006/0257396 A1 | 11/2006 | Jacobsen | WO | WO 90/07861 | 7/1990 | |
| 2006/0280743 A1 | 12/2006 | Basi et al. | WO | WO 90/12870 A1 | 11/1990 | |
| 2007/0021454 A1 | 1/2007 | Coburn et al. | WO | WO 90/12871 A1 | 11/1990 | |
| 2007/0072307 A1 | 3/2007 | Godavarti et al. | WO | WO 90/14837 A1 | 12/1990 | |
| 2007/0082367 A1 | 4/2007 | Godavarti et al. | WO | WO 90/14840 A1 | 12/1990 | |
| 2007/0134762 A1 | 6/2007 | Arumugham et al. | WO | WO 91/08760 A1 | 6/1991 | |
| 2007/0154480 A1 | 7/2007 | Schenk et al. | WO | WO 91/09967 A1 | 7/1991 | |
| 2007/0161088 A1 | 7/2007 | Arumugham et al. | WO | WO 91/10741 A1 | 7/1991 | |
| 2007/0196375 A1 | 8/2007 | Tobinick | WO | WO 91/12816 A1 | 9/1991 | |
| 2007/0238154 A1 | 10/2007 | Basi et al. | WO | WO 91/16819 A1 | 11/1991 | |
| 2008/0031954 A1 | 2/2008 | Paris et al. | WO | WO 91/16928 A1 | 11/1991 | |
| 2008/0050367 A1 | 2/2008 | Basi et al. | WO | WO 91/19795 A1 | 12/1991 | |
| 2008/0096818 A1 | 4/2008 | Schenk | WO | WO 91/19810 A1 | 12/1991 | |
| 2008/0145373 A1 | 6/2008 | Arumugham | WO | WO 92/01059 A1 | 1/1992 | |
| 2008/0221306 A1 | 9/2008 | Basi | WO | WO 92/05793 A1 | 4/1992 | |
| 2008/0227718 A1 | 9/2008 | Schenk | WO | WO 92/06187 A1 | 4/1992 | |
| 2008/0227719 A1 | 9/2008 | Schenk | WO | WO 92/06708 A1 | 4/1992 | |
| 2008/0279873 A1 | 11/2008 | Seubert | WO | WO 92/07944 A1 | 5/1992 | |
| 2008/0281082 A1 | 11/2008 | Basi | WO | WO 92/13069 A1 | 8/1992 | |
| 2008/0292625 A1 | 11/2008 | Schroeter | WO | WO 92/15330 A1 | 9/1992 | |
| 2008/0299074 A1 | 12/2008 | Arumugham | WO | WO 92/19267 A1 | 11/1992 | |
| 2009/0069544 A1 | 3/2009 | Basi | WO | WO 92/22653 A1 | 12/1992 | |
| 2009/0142270 A1 | 6/2009 | Schroeter et al. | WO | WO 93/02189 A1 | 2/1993 | |
| | | | WO | WO 93/04194 A1 | 3/1993 | |

| | | | | | | |
|---|---|---|---|---|---|---|
| WO | WO 93/12227 | A1 | 6/1993 | WO | WO 99/06545 A2 | 11/1999 |
| WO | WO 93/14200 | A1 | 7/1993 | WO | WO 99/58564 | 11/1999 |
| WO | WO 93/15760 | A1 | 8/1993 | WO | WO 99/60021 A2 | 11/1999 |
| WO | WO 93/16724 | A1 | 9/1993 | WO | WO 99/60024 A1 | 11/1999 |
| WO | WO 93/21950 | A1 | 11/1993 | WO | WO 00/20027 A2 | 4/2000 |
| WO | WO 94/00153 | A1 | 1/1994 | WO | WO 00/23082 A1 | 4/2000 |
| WO | WO 94/01772 | A1 | 1/1994 | WO | WO 00/26238 A2 | 5/2000 |
| WO | WO 94/03208 | A1 | 2/1994 | WO | WO 00/43039 A1 | 7/2000 |
| WO | WO 94/03615 | A1 | 2/1994 | WO | WO 00/43049 A1 | 7/2000 |
| WO | WO 94/05311 | A1 | 3/1994 | WO | WO 00/68263 A2 | 11/2000 |
| WO | WO 94/09364 | A1 | 4/1994 | WO | WO 00/72870 A1 | 12/2000 |
| WO | WO 94/09823 | A1 | 5/1994 | WO | WO 00/72876 A2 | 12/2000 |
| WO | WO 94/10569 | A1 | 5/1994 | WO | WO 00/72876 A3 | 12/2000 |
| WO | WO 94/16731 | A1 | 8/1994 | WO | WO 00/72880 A2 | 12/2000 |
| WO | WO 94/17197 | A1 | 8/1994 | WO | WO 00/72880 A3 | 12/2000 |
| WO | WO 94/21288 | A1 | 9/1994 | WO | WO 00/77178 A1 | 12/2000 |
| WO | WO 94/28412 | A1 | 12/1994 | WO | WO 01/05355 A2 | 1/2001 |
| WO | WO 94/29459 | A1 | 12/1994 | WO | WO 01/10900 A2 | 2/2001 |
| WO | WO 94/40895 | A1 | 12/1994 | WO | WO 01/18169 A3 | 3/2001 |
| WO | WO 95/04151 | A2 | 2/1995 | WO | WO 01/39796 A2 | 6/2001 |
| WO | WO 95/05393 | A2 | 2/1995 | WO | WO 01/42306 A2 | 6/2001 |
| WO | WO 95/05849 | A1 | 3/1995 | WO | WO 01/62284 A2 | 8/2001 |
| WO | WO 95/05853 | A1 | 3/1995 | WO | WO 01/62801 A2 | 8/2001 |
| WO | WO 95/06407 | A1 | 3/1995 | WO | WO 01/77167 A2 | 10/2001 |
| WO | WO 95/07301 | A1 | 3/1995 | WO | WO 01/78777 A2 | 10/2001 |
| WO | WO 95/08999 | A1 | 4/1995 | WO | WO 01/90182 A2 | 11/2001 |
| WO | WO 95/11008 | A2 | 4/1995 | WO | WO 02/03911 A2 | 1/2002 |
| WO | WO 95/11311 | A1 | 4/1995 | WO | WO 02/21141 A2 | 3/2002 |
| WO | WO 95/11994 | A1 | 5/1995 | WO | WO 02/34777 A1 | 5/2002 |
| WO | WO 95/12815 | A1 | 5/1995 | WO | WO 02/34878 A2 | 5/2002 |
| WO | WO 95/17085 | A1 | 6/1995 | WO | WO 02/46237 A2 | 6/2002 |
| WO | WO 95/23166 | A1 | 8/1995 | WO | WO 02/46237 A3 | 6/2002 |
| WO | WO 95/23860 | A2 | 9/1995 | WO | WO 02/060481 A1 | 8/2002 |
| WO | WO 95/31996 | A1 | 11/1995 | WO | WO 02/088306 A2 | 11/2002 |
| WO | WO 96/01126 | A1 | 1/1996 | WO | WO 02/088307 A2 | 11/2002 |
| WO | WO 96/08565 | A2 | 3/1996 | WO | WO 02/096457 A2 | 12/2002 |
| WO | WO 96/14061 | A1 | 5/1996 | WO | WO 02/096937 A2 | 12/2002 |
| WO | WO 96/18900 | A1 | 6/1996 | WO | WO 03/009817 A2 | 2/2003 |
| WO | WO 96/22373 | A1 | 7/1996 | WO | WO 03/015691 A2 | 2/2003 |
| WO | WO 96/03144 | A1 | 8/1996 | WO | WO 03/016466 A2 | 2/2003 |
| WO | WO 96/25435 | A1 | 8/1996 | WO | WO 03/016467 A2 | 2/2003 |
| WO | WO 96/28471 | A1 | 9/1996 | WO | WO 03/016467 A3 | 2/2003 |
| WO | WO 96/29421 | A1 | 9/1996 | WO | WO 03/020212 A2 | 3/2003 |
| WO | WO 96/33739 | A1 | 10/1996 | WO | WO 03/039485 A2 | 5/2003 |
| WO | WO 96/37621 | A2 | 11/1996 | WO | WO 03/051374 A2 | 6/2003 |
| WO | WO 96/39176 | A1 | 12/1996 | WO | WO 03/072036 A2 | 9/2003 |
| WO | WO 96/39834 | A1 | 12/1996 | WO | WO 03/072036 A3 | 9/2003 |
| WO | WO 96/40895 | A1 | 12/1996 | WO | WO 03/074081 A1 | 9/2003 |
| WO | WO 97/03192 | A3 | 1/1997 | WO | WO 03/077858 A2 | 9/2003 |
| WO | WO 97/05164 | A1 | 2/1997 | WO | WO 03/077858 A3 | 9/2003 |
| WO | WO 97/08320 | A1 | 3/1997 | WO | WO 03/104437 A2 | 12/2003 |
| WO | WO 97/10505 | A1 | 3/1997 | WO | WO 03/105894 A1 | 12/2003 |
| WO | 97/13855 | | 4/1997 | WO | WO 2004/013172 A2 | 2/2004 |
| WO | WO 97/17613 | A1 | 5/1997 | WO | WO 2004/013172 A3 | 2/2004 |
| WO | WO 97/18855 | A1 | 5/1997 | WO | WO 2004/016282 A1 | 2/2004 |
| WO | WO 97/21728 | A1 | 6/1997 | WO | WO 2004/031400 A2 | 4/2004 |
| WO | WO 97/28816 | A1 | 8/1997 | WO | WO 2004/044204 A2 | 5/2004 |
| WO | WO 97/32017 | A1 | 9/1997 | WO | WO 2004/044204 A3 | 5/2004 |
| WO | WO 97/36601 | A1 | 10/1997 | WO | WO 2004/055164 A2 | 7/2004 |
| WO | WO 97/37031 | A1 | 10/1997 | WO | WO 2004/069182 A2 | 8/2004 |
| WO | WO 97/40147 | A1 | 10/1997 | WO | WO 2004/069182 A3 | 8/2004 |
| WO | WO 98/02462 | A1 | 1/1998 | WO | WO 2004/071408 A2 | 8/2004 |
| WO | 98/04720 | A1 | 2/1998 | WO | WO 2004/080419 A2 | 9/2004 |
| WO | WO 98/05350 | A1 | 2/1998 | WO | WO 2004/080419 A3 | 9/2004 |
| WO | WO 98/07850 | A2 | 2/1998 | WO | WO 2004/108895 A2 | 12/2004 |
| WO | WO 98/08098 | A1 | 2/1998 | WO | WO 2004/108895 A3 | 12/2004 |
| WO | WO 98/08868 | A1 | 3/1998 | WO | WO 2005/014041 A2 | 2/2005 |
| WO | WO 98/22120 | A1 | 5/1998 | WO | WO 2005/026211 A2 | 3/2005 |
| WO | WO 98/33815 | A1 | 8/1998 | WO | WO 2005/026211 A3 | 3/2005 |
| WO | WO 98/39303 | A1 | 9/1998 | WO | WO 2005/035753 A | 4/2005 |
| WO | WO 98/44955 | A1 | 10/1998 | WO | WO 2005/058940 A2 | 6/2005 |
| WO | WO 98/56418 | A1 | 12/1998 | WO | WO 2005/058941 A2 | 6/2005 |
| WO | WO 99/00150 | A2 | 1/1999 | WO | WO 2006/042158 A | 4/2006 |
| WO | WO 99/06066 | A2 | 2/1999 | WO | WO 2006/066049 A2 | 6/2006 |
| WO | WO 99/06587 | A2 | 2/1999 | WO | WO 2006/066171 A1 | 6/2006 |
| WO | WO 99/10008 | A1 | 3/1999 | WO | WO 2006/081587 A2 | 8/2006 |
| WO | WO 99/27911 | A1 | 6/1999 | WO | WO 2006/081587 A3 | 8/2006 |
| WO | WO 99/27944 | A1 | 6/1999 | WO | WO 2006/083689 A2 | 8/2006 |
| WO | WO 99/27949 | A1 | 6/1999 | WO | WO 2008/131298 A2 | 10/2008 |

| | | |
|---|---|---|
| WO | WO 2008/131298 A3 | 12/2008 |
| WO | 2009/052439 A2 | 4/2009 |
| WO | WO 2010/044803 A1 | 4/2010 |

OTHER PUBLICATIONS

U.S. Appl. No. 09/724,477, Notice of Allowance mailed Apr. 30, 2003.
U.S. Appl. No. 09/724,477, Notice of Allowance mailed Sep. 23, 2003
U.S. Appl. No. 09/723,927, Notice of Allowance mailed Sep. 23, 2003.
U.S. Appl. No. 09/723,762, Notice of Allowance mailed May 1, 2003
U.S. Appl. No. 09/724,102, Notice of Allowance mailed Aug. 22, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 10/232,030, Notice of Allowance mailed Sep. 4, 2008.
U.S. Appl. No. 10/816,022, Notice of Allowance mailed Jul. 1, 2004.
U.S. Appl. No. 10/816,529, Notice of Allowance mailed Jul. 1, 2004.
U.S. Appl. No. 10/815,391, Notice of Allowance mailed Jul. 1, 2004.
U.S. Appl. No. 10/815,353, Notice of Allowance mailed Jul. 1, 2004.
U.S. Appl. No. 10/816,380, Notice of Allowance mailed Dec. 22, 2004.
U.S. Appl. No. 10/815,404, Notice of Allowance mailed Oct. 15, 2004.
U.S. Appl. No. 10/884,892, Notice of Allowance mailed Mar. 28, 2005.
U.S. Appl. No. 09/723,384, Notice of Allowance mailed Mar. 31, 2003.
U.S. Appl. No. 09/724,940, Notice of Allowance mailed Oct. 4, 2004.
U.S. Appl. No. 09/724,961, Notice of Allowance mailed Dec. 3, 2003.
U.S. Appl. No. 09/580,018, Notice of Allowance mailed Dec. 3, 2003.
U.S. Appl. No. 09/724,552, Notice of Allowance mailed Dec. 3, 2003.
U.S. Appl. No. 09/724,551, Notice of Allowance mailed Dec. 4, 2003.
U.S. Appl. No. 09/724,567, Notice of Allowance mailed Mar. 3, 2004.
U.S. Appl. No. 09/724,953, Notice of Allowance mailed Mar. 11, 2004.
U.S. Appl. No. 09/979,952, Notice of Allowance mailed Nov. 12, 2004.
U.S. Appl. No. 10/934,609, Notice of Allowance mailed Dec. 22, 2004.
U.S. Appl. No. 10/934,609, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Aug. 17, 2005.
U.S. Appl. No. 10/933,559, Notice of Allowance mailed Dec. 22, 2004.
U.S. Appl. No. 10/010,942, Notice of Allowance mailed May 11, 2006.
U.S. Appl. No. 10/388,389, Notice of Allowance mailed May 31, 2006.
U.S. Appl. No. 10/388,214, Notice of Allowance mailed Mar. 1, 2007.
U.S. Appl. No. 09/201,430, Office Action mailed Dec. 21, 1999.
U.S. Appl. No. 09/201,430, Office Action mailed May 10, 2000.
U.S. Appl. No. 09/204,838, Office Action mailed Mar. 17, 2000.
U.S. Appl. No. 09/322,289, Office Action mailed Sep. 29, 2000.
U.S. Appl. No. 09/497,553, Office Action mailed Oct. 3, 2003.
U.S. Appl. No. 09/580,015, Office Action mailed Feb. 11, 2002.
U.S. Appl. No. 09/580,018, Office Action mailed Mar. 12, 2002.
U.S. Appl. No. 09/580,019, Office Action mailed Mar. 12, 2002.
U.S. Appl. No. 09/723,544, Office Action mailed Sep. 23, 2002.
U.S. Appl. No. 09/723,760, Office Action mailed Mar. 12, 2002.
U.S. Appl. No. 09/723,765, Office Action mailed Mar. 12, 2002.
U.S. Appl. No. 09/723,766, Office Action mailed Mar. 5, 2002.
U.S. Appl. No. 09/723,766, Office Action mailed Jun. 11, 2002.
U.S. Appl. No. 09/724,273, Office Action mailed Jul. 02, 2002.
U.S. Appl. No. 09/724,273, Office Action mailed Nov. 08, 2005.
U.S. Appl. No. 09/724,288, Office Action mailed Mar. 12, 2002.
U.S. Appl. No. 09/724,288, Office Action mailed May 3, 2004.
U.S. Appl. No. 09/724,319, Office Action mailed Jul. 21, 2003.
U.S. Appl. No. 09/724,495, Office Action mailed Sep. 24, 2002.
U.S. Appl. No. 09/724,495, Office Action mailed Mar. 13, 2003.
U.S. Appl. No. 09/724,551, Office Action mailed Jul. 2, 2002.
U.S. Appl. No. 09/724,552, Office Action mailed May 6, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,921, Office Action mailed Apr. 30, 2002.
U.S. Appl. No. 09/724,929, Office Action mailed Mar. 22, 2002.
U.S. Appl. No. 09/724,940, Office Action mailed Mar. 13, 2003.
U.S. Appl. No. 09/724,953, Office Action mailed Mar. 26, 2002.
U.S. Appl. No. 09/724,961, Office Action mailed Mar. 12, 2002.
U.S. Appl. No. 09/979,701, Office Action mailed Feb. 15, 2005.
U.S. Appl. No. 09/979,701, Office Action mailed Sep. 15, 2005.
U.S. Appl. No. 09/979,952, Office Action mailed Aug. 7, 2003.
U.S. Appl. No. 09/980,568, Office Action mailed May 29, 2003.
U.S. Appl. No. 10/010,942, Office Action mailed Sep. 24, 2003.
U.S. Appl. No. 10/232,030, Office Action mailed Dec. 2, 2004.
U.S. Appl. No. 10/388,214, Office Action mailed May 31, 2005.
U.S. Appl. No. 10/388,389, Office Action mailed Nov. 22, 2005.
U.S. Appl. No. 10/429,216, Office Action mailed Dec. 28, 2005.
U.S. Appl. No. 10/544,093, Office Action, mailed Jun. 16, 2008.
U.S. Appl. No. 10/625,854, Office Action mailed Nov. 10, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/777,792, Office Action mailed Mar. 2, 2006.
U.S. Appl. No. 10/788,666 , Office Action mailed Jan. 12, 2005.
U.S. Appl. No. 10/789,273, Office Action mailed Sep. 22, 2006.
U.S. Appl. No. 10/822,968, Office Action mailed Mar. 22, 2006.
U.S. Appl. No. 10/823,463, Office Action mailed Feb. 4, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/858,855, Office Action mailed Jun. 22, 2006.
U.S. Appl. No. 10/923,267, Office Action mailed Jul. 21, 2006.
U.S. Appl. No. 10/923,469, Office Action mailed Mar. 29, 2007.
U.S. Appl. No. 10/923,474, Office Action mailed Feb. 15, 2005.
U.S. Appl. No. 10/928,926, Office Action mailed Jan. 12, 2007.
U.S. Appl. No. 10/934,819, Office Action mailed Oct. 14, 2005.
U.S. Appl. No. 11/058,757, Office Action mailed May 3, 2005.
U.S. Appl. No. 11/058,757, Office Action mailed Aug. 24, 2005.
U.S. Appl. No. 11/244,678, Office Action mailed Apr. 18, 2007.
U.S. Appl. No. 11/245,524, Office Action mailed May 15, 2007.
U.S. Appl. No. 11/245,916, Office Action mailed Jan. 13, 2006.
U.S. Appl. No. 11/260,047, Office Action mailed Oct. 26, 2006.
U.S. Appl. No. 11/303,478, Office Action mailed Apr. 1, 2008.
U.S. Appl. No. 11/303,478, Office Action mailed Oct. 16, 2008.
U.S. Appl. No. 11/304,072, Office Action mailed Dec. 20, 2006.
U.S. Appl. No. 11/304,986, Office Action mailed Jan. 2, 2008.
U.S. Appl. No. 11/305,889, Office Action mailed Jul. 25, 2008.
U.S. Appl. No. 11/305,889, Office Action mailed May 4, 2007.
U.S. Appl. No. 11/305,899, Office Action mailed Apr. 4, 2008.
U.S. Appl. No. 11/342,353, Office Action mailed Mar. 26, 2008.
U.S. Appl. No. 11/342,353, Office Action mailed Jul. 09, 2008.
U.S. Appl. No. 11/454,772, Office Action mailed Feb. 27, 2007.
U.S. Appl. No. 09/201,430, Office Action mailed Jan. 17, 2001.
U.S. Appl. No. 09/201,430, Examiner Interview Summary mailed May 30, 2001.
U.S. Appl. No. 09/204,838, Office Action mailed Dec. 21, 2000.
U.S. Appl. No. 09/322,289, Office Action mailed Jun. 19, 2001.
U.S. Appl. No. 09/322,289, Examiner Interview Summary mailed Jun. 27, 2006.
U.S. Appl. No. 09/497,553, Office Action mailed Nov. 29, 2005.
U.S. Appl. No. 09/580,018, Office Action mailed May 20, 2003.
U.S. Appl. No. 09/723,384, Office Action mailed Oct. 9, 2002.
U.S. Appl. No. 09/723,384, Examiner Interview Summary mailed Mar. 28, 2003.
U.S. Appl. No. 09/723,544, Office Action mailed Aug. 11, 2003.

U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Office Action mailed Dec. 3, 2002.
U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,765, Examiner Interview Summary mailed Oct. 8, 2008.
U.S. Appl. No. 09/723,766, Office Action mailed Nov. 1, 2002.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 9/724,319, Office Action mailed Apr. 26, 2004.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Office Action mailed Jun. 3, 2003.
U.S. Appl. No. 09/724,552, Examiner Interview Summary mailed Dec. 3, 2003.
U.S. Appl. No. 09/724,567, Office Action mailed Nov. 15, 2002.
U.S. Appl. No. 09/724,575, Office Action mailed Nov. 21, 2002.
U.S. Appl. No. 09/724,575, Examiner Interview Summary mailed May 6, 2005.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961 Office Action mailed May 16, 2003.
U.S. Appl. No. 09/724,961, Examiner Interview Summary mailed Dec. 3, 2003.
U.S. Appl. No. 09/979,701, Office Action mailed Jan. 10, 2006.
U.S. Appl. No. 09/979,952, Office Action mailed Dec. 30, 2003.
U.S. Appl. No. 09/980,568, Office Action mailed Feb. 23, 2004.
U.S. Appl. No. 10/010,942, Office Action mailed May 26, 2004.
U.S. Appl. No. 10/010,942, Examiner Interview Summary mailed Nov. 18, 2004.
U.S. Appl. No. 10/010,942, Examiner Interview Summary mailed Jan. 19, 2005.
U.S. Appl. No. 10/010,942, Examiner Interview Summary mailed Feb. 22, 2006.
U.S. Appl. No. 10/010,942 ,Examiner Interview Summary mailed May 10, 2006.
U.S. Appl. No. 10/010,942 ,Examiner Interview Summary mailed May 11, 2006.
U.S. Appl. No. 10/010,942, Examiner Interview Summary mailed May 11, 2006.
U.S. Appl. No. 10/232,030, Office Action mailed Oct. 14, 2005.
U.S. Appl. No. 10/232,030, Examiner Interview Summary mailed Feb. 17, 2006.
U.S. Appl. No. 10/388,214, Office Action mailed Jan. 31, 2006.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,389, Examiner Interview Summary mailed May 22, 2006.
U.S. Appl. No. 10/388,389, Examiner Interview Summary mailed May 31, 2006.
U.S. Appl. No. 10/429,216, Office Action mailed Apr. 11, 2006.
U.S. Appl. No. 10/625,854, Office Action mailed Feb. 7, 2006.
U.S. Appl. No. 10/625,854, Examiner Interview Summary mailed Jun. 26, 2007.
U.S. Appl. No. 10/703,713, Office Action mailed Sep. 27, 2005.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/889,999, Office Action mailed Jan. 5, 2005.
U.S. Appl. No. 10/923,469, Examiner Interview Summary mailed Apr. 9, 2008.
U.S. Appl. No. 10/923,469, Office Action mailed Jul. 3, 2007.
U.S. Appl. No. 10/923,471, Office Action mailed Jan. 5, 2005.
U.S. Appl. No. 10/923,471, Examiner Interview Summary mailed Oct. 20, 2008.
U.S. Appl. No. 10/923,474 Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.
U.S. Appl. No. 10/934,819, Office Action mailed Jan. 24, 2006.
U.S. Appl. No. 11/058,757, Office Action mailed Oct. 20, 2005.
U.S. Appl. No. 11/108,102, Office Action mailed Jan. 11, 2006.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Office Action mailed May 15, 2007.
U.S. Appl. No. 11/260,047, Examiner Interview Summary mailed May 15, 2007.
U.S. Appl. No. 11/274,493, Office Action mailed Apr. 23, 2007.
U.S. Appl. No. 11/305,889, Office Action mailed Aug. 14, 2007.
U.S. Appl. No. 11/342,353, Office Action mailed Nov. 14, 2008.
U.S. Appl. No. 11/45,772, Examiner Interview Summary mailed Apr. 13, 2007.
U.S. Appl. No. 11/454,772, Office Action mailed Jun. 27, 2007.
U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 24, 2005.
U.S. Appl. No. 09/322,289, Office Action mailed Nov. 17, 2006.
U.S. Appl. No. 09/322,289, Office Action mailed Feb. 7, 2008.
U.S. Appl. No. 09/322,289, Office Action mailed Nov. 4, 2008.
U.S. Appl. No. 09/723,713, Office Action mailed Oct. 24, 2003.
U.S. Appl. No. 09/723,713, Office Action mailed Apr. 19, 2005.
U.S. Appl. No. 09/723,725, Office Action mailed Dec. 9, 2002.
U.S. Appl. No. 09/723,760, Office Action mailed May 4, 2005.
U.S. Appl. No. 09/723,765, Office Action mailed May 22, 2008.
U.S. Appl. No. 09/723,765, Office Action mailed Aug. 10, 2004.
U.S. Appl. No. 09/724,273, Office Action mailed Jun. 22, 2004.
U.S. Appl. No. 09/724,273, Office Action mailed Jun. 8, 2006.
U.S. Appl. No. 09/724,273, Office Action mailed Dec. 22, 2006.
U.S. Appl. No. 09/724,288, Office Action mailed Dec. 14, 2004.
U.S. Appl. No. 09/724,288, Office Action mailed Jun. 21, 2006.
U.S. Appl. No. 09/724,288, Office Action mailed Apr. 23, 2007.
U.S. Appl. No. 09/724,288, Office Action mailed Oct. 3, 2007.
U.S. Appl. No. 09/724,288, Office Action mailed Mar. 18, 2008.
U.S. Appl. No. 09/724,319, Office Action mailed Aug. 15, 2005.
U.S. Appl. No. 09/724,319, Office Action mailed May 16, 2007.
U.S. Appl. No. 09/724,319, Office Action mailed Jan. 11, 2008.
U.S. Appl. No. 09/724,575, Office Action mailed May 6, 2005.
U.S. Appl. No. 09/724,575, Office Action mailed Oct. 17, 2005.
U.S. Appl. No. 09/724,575, Office Action mailed Mar. 31, 2006.
U.S. Appl. No. 09/980,568, Office Action mailed Nov. 2, 2004.
U.S. Appl. No. 10/010,942, Office Action mailed Jan. 19, 2005.
U.S. Appl. No. 10/010,942, Office Action mailed Oct. 3, 2005.
U.S. Appl. No. 10/232,030, Office Action mailed Jun. 15, 2007.
U.S. Appl. No. 10/429,216, Office Action mailed Jan. 28, 2008.
U.S. Appl. No. 10/625,854, Office Action mailed May 15, 2007.
U.S. Appl. No. 10/703,713, Office Action mailed Jun. 2, 2006.
U.S. Appl. No. 10/777,792, Office Action mailed Apr. 3, 2008.
U.S. Appl. No. 10/828,548, Office Action mailed Sep. 11, 2007.

U.S. Appl. No. 10/889,999, Office Action mailed Aug. 15, 2005.
U.S. Appl. No. 10/890,000, Office Action mailed Sep. 19, 2005.
U.S. Appl. No. 10/890,000, Office Action mailed Mar. 10, 2006.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Aug. 24, 2005.
U.S. Appl. No. 10/923,471, Office Action mailed May 15, 2006.
U.S. Appl. No. 10/923,471, Office Action mailed Jul. 31, 2007.
U.S. Appl. No. 10/923,474 Office Action mailed Jun. 26, 2007.
U.S. Appl. No. 11/244,678, Office Action mailed Sep. 23, 2008.
U.S. Appl. No. 11/245,524, Office Action mailed Jun. 4, 2008.
U.S. Appl. No. 11/245,916, Office Action mailed Jan. 28, 2008.
U.S. Appl. No. 11/342,353, Office Action mailed Jul. 22, 2008.
U.S. Appl. No. 11/244,678, Office Action mailed Mar. 24, 2008.
U.S. Appl. No. 10/232,030, Advisory Action mailed Oct. 30, 2006.
U.S. Appl. No. 10/232,030, Office Action mailed Apr. 1, 2008.
U.S. Appl. No. 10/704,070, Office Action mailed Jun. 6, 2006.
U.S. Appl. No. 10/771,174, Office Action mailed Aug. 23, 2007.
U.S. Appl. No. 10/858,855, Office Action mailed Nov. 23, 2007.
U.S. Appl. No. 10/858,855, Advisory Action mailed Apr. 7, 2008.
U.S. Appl. No. 10/388,214, Office Action mailed Jul. 28, 2006.
U.S. Appl. No. 11/305,889, Office Action mailed May 23, 2008.
U.S. Appl. No. 11/454,772, Office Action mailed Dec. 21, 2007.
U.S. Appl. No. 09/201,430, Office Action mailed Nov. 26, 2001.
U.S. Appl. No. 09/201,430, Advisory Action mailed Jun. 18, 2002.
U.S. Appl. No. 09/322,289, Office Action mailed Oct. 16, 2005.
U.S. Appl. No. 09/322,289, Office Action mailed Nov. 29, 2005.
U.S. Appl. No. 09/322,289, Office Action mailed Jul. 17, 2007.
U.S. Appl. No. 09/723,713, Office Action mailed Feb. 12, 2002.
U.S. Appl. No. 09/723,713, Office Action mailed Jun. 3, 2004.
U.S. Appl. No. 09/723,713, Office Action mailed Jan. 11, 2006.
U.S. Appl. No. 09/723,713, Advisory Action mailed Dec. 20, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,760, Advisory Action mailed Dec. 16, 2004.
U.S. Appl. No. 09/724,319 Office Action mailed May 2, 2006.
U.S. Appl. No. 09/724,495, Office Action mailed Sep. 26, 2005.
U.S. Appl. No. 09/724,495, Advisory Action mailed May 16, 2004.
U.S. Appl. No. 10/429,216, Office Action mailed Oct. 16, 2008.
U.S. Appl. No. 10/828,548, Office Action mailed Oct. 24, 2006.
U.S. Appl. No. 10/828,548, Office Action mailed Jun. 4, 2008.
U.S. Appl. No. 10/777,792, Office Action mailed Nov. 18, 2008.
U.S. Appl. No. 10/828,548, Advisory Action mailed Jun. 8, 2007.
U.S. Appl. No. 10/923,471, Office Action mailed Dec. 29, 2006.
U.S. Appl. No. 10/923,471, Office Action mailed Apr. 24, 2008.
U.S. Appl. No. 10/923,474 Office Action mailed Aug. 4, 2006.
U.S. Appl. No. 10/923,474, Advisory Action mailed Feb. 22, 2007.
U.S. Appl. No. 11/058,757, Office Action mailed Aug. 11, 2006.
U.S. Appl. No. 11/058,757, Advisory Action mailed Mar. 5, 2007.
U.S. Appl. No. 09/724,273, Office Action mailed Oct. 16, 2003.
U.S. Appl. No. 09/724,273, Advisory Action mailed Mar. 18, 2004.
U.S. Appl. No. 09/724,273, Office Action mailed Dec. 28, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,288, Office Action mailed Sep. 9, 2003.
U.S. Appl. No. 09/724,288, Advisory Action mailed Jan. 6, 2004.
U.S. Appl. No. 09/724,288, Office Action mailed Jul. 12, 2005.
U.S. Appl. No. 09/724,288, Advisory Action mailed Mar. 3, 2006.
U.S. Appl. No. 10/777,792, Office Action mailed May 8, 2007.
U.S. Appl. No. 10/890,024, Office Action mailed Jun. 1, 2006.
U.S. Appl. No. 10/889,999, Office Action mailed Mar. 14, 2006.
U.S. Appl. No. 10/890,000, Office Action mailed Nov. 24, 2006.
U.S. Appl. No. 10/890,000, Advisory Action mailed Jan. 14, 2008.
U.S. Appl. No. 09/723,765, Office Action mailed Oct. 7, 2003.
U.S. Appl. No. 09/723,765, Advisory Action mailed Feb. 9, 2004.
U.S. Appl. No. 09/723,765, Advisory Action mailed May 4, 2005.
U.S. Appl. No. 09/204,838, Office Action mailed Sep. 27, 2001.
U.S. Appl. No. 09/724,567, Office Action mailed Jul. 23, 2003.
U.S. Appl. No. 09/724,575, Office Action mailed Jul. 25, 2003.
U.S. Appl. No. 09/724,575, Advisory Action mailed Feb. 12, 2004.
U.S. Appl. No. 09/724,575, Office Action mailed Oct. 12, 2006.
U.S. Appl. No. 09/724,953, Office Action mailed Jul. 25, 2003.
U.S. Appl. No. 11/274,493, Office Action mailed Nov. 2, 2007.
U.S. Appl. No. 10/625,854, Office Action mailed Aug. 23, 2006.
U.S. Appl. No. 10/625,854, Office Action mailed Nov. 7, 2007.
U.S. Appl. No. 10/625,854, Advisory Action mailed Jan. 8, 2008.
U.S. Appl. No. 11/108,102, Office Action mailed Sep. 6, 2006.
U.S. Appl. No. 11/245,916, Office Action mailed Jan. 12, 2007.
U.S. Appl. No. 11/245,916, Advisory Action mailed May 15, 2007.
U.S. Appl. No. 11/245,916, Advisory Action mailed Oct. 18, 2007.
U.S. Appl. No. 10/429,216, Office Action mailed Jan. 3, 2007.
U.S. Appl. No. 10/890,070, Office Action mailed Jun. 1, 2006.
U.S. Appl. No. 09/724,288, Notice of Allowance mailed Mar. 23, 2009.
U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 09/322,289, Office Action mailed Jun. 4, 2009.
U.S. Appl. No. 09/723,765, Office Action mailed Dec. 5, 2008.
U.S. Appl. No. 09/724,288, Office Action mailed Dec. 22, 2008.
U.S. Appl. No. 09/724,319 Advisory Action mailed Oct. 28, 2009.
U.S. Appl. No. 09/724,319 Office Action mailed Apr. 8, 2009.
U.S. Appl. No. 10/429,216, Office Action mailed Mar. 6, 2009.
U.S. Appl. No. 10/923,469. Advisory Action mailed Apr. 16, 2009.
U.S. Appl. No. 10/923,469. Office Action mailed Dec. 29, 2008.
U.S. Appl. No. 10/923,471, Office Action mailed Dec. 24, 2009.
U.S. Appl. No. 11/245,524, Office Action mailed Nov. 20, 2009.
U.S. Appl. No. 11/245,916, Advisory Action mailed Jun. 10, 2009.
U.S. Appl. No. 11/842,042, Office Action mailed Mar. 30, 2010.
U.S. Appl. No. 10/429,216, Office Action mailed Mar. 12, 2010.
U.S. Appl. No. 10/544,093, Office Action mailed Jan. 22, 2010.
U.S. Appl. No. 10/858,855 Office Action mailed Dec. 12, 2008.
U.S. Appl. No. 10/858,855 Office Action mailed Dec. 15, 2009.
U.S. Appl. No. 10/923,471, Office Action mailed Mar. 20, 2009.
U.S. Appl. No. 11/245,524, Office Action mailed Apr. 17, 2009.
U.S. Appl. No. 11/245,916, Office Action mailed Oct. 31, 2008.
U.S. Appl. No. 11/842,023, Office Action mailed Aug. 14, 2009.
U.S. Appl. No. 09/322,289, Examiner Interview Summary mailed Jan. 15, 2009.
U.S. Appl. No. 09/723,765, Examiner Interview Summary mailed Jan. 16, 2009.
U.S. Appl. No. 10/429,216, Examiner Interview Summary mailed Mar. 6, 2006.
U.S. Appl. No. 10/544,093, Office Action mailed Feb. 9, 2009.
U.S. Appl. No. 11/303,478, Office Action mailed Mar. 18, 2009.
U.S. Appl. No. 11/304,986, Office Action mailed Dec. 31, 2008.
U.S. Appl. No. 11/305,899 Office Action mailed Dec. 10, 2008.
U.S. Appl. No. 11/520,438, Office Action mailed Aug. 6, 2009.
U.S. Appl. No. 11/842,023, Office Action mailed Nov. 13, 2008.
U.S. Appl. No. 11/842,042, Office Action mailed Jun. 24, 2009.
U.S. Appl. No. 11/842,056, Office Action mailed May 6, 2009.
U.S. Appl. No. 11/842,085, Office Action mailed Sep. 30, 2009.
U.S. Appl. No. 12/037,045, Office Action mailed Apr. 28, 2010.
U.S. Appl. No. 12/253,929, Office Action mailed Apr. 28, 2010.
U.S. Appl. No. 12/336,340, Office Action mailed Mar. 4, 2010.
U.S. Appl. No. 11/516,724, Office Action mailed Jan. 27, 2009.
U.S. Appl. No. 11/520,438, Office Action mailed Apr. 2, 2009.
U.S. Appl. No. 11/707,639 Office Action mailed Apr. 3, 2009.
U.S. Appl. No. 11/842,085, Office Action mailed Apr. 14, 2009.
U.S. Appl. No. 11/842,113, Office Action mailed Dec. 17, 2009.
U.S. Appl. No. 11/842,120, Office Action mailed Apr. 14, 2009.
U.S. Appl. No. 12/106,206, Office Action mailed Feb. 5, 2010.
U.S. Appl. No. 12/328,740, Office Action mailed Oct. 9, 2009.
U.S. Appl. No. 12/253,929, Office Action mailed Jan. 25, 2010.
U.S. Appl. No. 60/999,423, Oct. 17, 2007, Black.
U.S. Appl. No. 11/894,789, Aug. 20, 2007, Basi.
U.S. Appl. No. 11/894,754, Aug. 20, 2007, Basi.
U.S. Appl. No. 11/894,714, Aug. 20, 2007, Basi.
U.S. Appl. No. 11/894,665, Aug. 20, 2007, Schenk.
U.S. Appl. No. 11/893,123, Aug. 20, 2007, Basi et al.
U.S. Appl. No. 11/893,110, Aug. 20, 2007, Basi et al.
U.S. Appl. No. 11/893,103, Aug. 20, 2007, Basi et al.
U.S. Appl. No. 11/893,094, Aug. 20, 2007, Basi et al.
U.S. Appl. No. 11/842,101, Aug. 20, 2007, Schenk.
U.S. Appl. No. 11/841,950, Aug. 20, 2007, Arumugham.

U.S. Appl. No. 11/841,897, Aug. 20, 2007, Arumugham.
U.S. Appl. No. 11/841,882, Aug. 20, 2007, Arumugham.
U.S. Appl. No. 11/841,857, Aug. 20, 2007, Warne et al.
U.S. Appl. No. 11/841,849, Aug. 20, 2007, Arumugham.
U.S. Appl. No. 11/841,794, Aug. 20, 2007, Warne et al.
U.S. Appl. No. 11/841,832, Aug. 20, 2007, Warne et al.
U.S. Appl. No. 60/793,014, Apr. 18, 2006.
U.S. Appl. No. 11/396,417, Mar. 30, 2006, Schenk.
U.S. Appl. No. 11/396,391, Mar. 30, 2006, Schenk.
U.S. Appl. No. 11/358,951, Feb. 22, 2006, Solomon et al.
U.S. Appl. No. 60/736,119, Nov. 10, 2005, Jacobson.
U.S. Appl. No. 60/736,045, Nov. 10, 2005, Johnson-Wood.
U.S. Appl. No. 60/735,687, Nov. 10, 2005, Jacobson.
U.S. Appl. No. 60/691,821, Jun. 17, 2005, Godavarti.
U.S. Appl. No. 09/980,568, Mar. 12, 2005, Hirtzer.
U.S. Appl. No. 60/648,639, Jan. 28, 2005, Luisi et al.
U.S. Appl. No. 60/648,631, Jan. 28, 2005, Luisi et al.
U.S. Appl. No. 60/637,253, Dec. 16, 2004, Jacobson.
U.S. Appl. No. 60/637,138, Dec. 16, 2004, Jacobson.
U.S. Appl. No. 60/636,842, Dec. 15, 2004, Jacobson.
U.S. Appl. No. 60/636,810, Dec. 15, 2004, Jacobson.
U.S. Appl. No. 60/636,776, Dec. 15, 2004, Basi.
U.S. Appl. No. 60/636,687, Dec. 15, 2004, Johnson-Wood.
U.S. Appl. No. 60/636,684, Dec. 15, 2004, Basi.
U.S. Appl. No. 60/622,525, Oct. 26, 2004, Pavliakova.
U.S. Appl. No. 60/616,474, Oct. 5, 2004, Sinacore.
U.S. Appl. No. 60/530,481, Dec. 17, 2003, Arumugham.
U.S. Appl. No. 60/530,480, Dec. 17, 2003, Arumugham.
U.S. Appl. No. 60/474,654, May 30, 2003, Basi.
U.S. Appl. No. 60/444,150, Feb. 1, 2003, Yednock.
U.S. Appl. No. 09/979,701, Mar. 13, 2002, Schenk.
U.S. Appl. No. 60/363,751, Mar. 12, 2002, Basi.
U.S. Appl. No. 60/254,465, Dec. 8, 2000, Holtzman et al.
U.S. Appl. No. 60/254,498, Dec. 8, 2000, Holtzman et al.
U.S. Appl. No. 60/251,892, Dec. 6, 2000, Basi et al.
U.S. Appl. No. 09/724,842, Nov. 28, 2000, Chalifour et al.
U.S. Appl. No. 09/724,929, Nov. 28, 2000, Weiner.
U.S. Appl. No. 09/724,921, Nov. 28, 2000, Weiner.
U.S. Appl. No. 09/724,575, Nov. 28, 2000, Schenk.
U.S. Appl. No. 09/724,291, Nov. 28, 2000, Schenk.
U.S. Appl. No. 09/724,273, Nov. 28, 2000, Schenk.
U.S. Appl. No. 09/723,544, Nov. 28, 2000, Schenk.
U.S. Appl. No. 09/724,495, Nov. 27, 2000, Schenk.
U.S. Appl. No. 09/724,319, Nov. 27, 2000, Schenk.
U.S. Appl. No. 09/723,766, Nov. 27, 2000, Hirtzer.
U.S. Appl. No. 09/723,760, Nov. 27, 2000, Schenk.
U.S. Appl. No. 09/723,725, Nov. 27, 2000, Hirtzer.
U.S. Appl. No. 09/723,713, Nov. 27, 2000, Schenk.
U.S. Appl. No. 09/585,656, Jun. 1, 2000, Hirtzer et al.
U.S. Appl. No. 09/580,019, May 26, 2000, Schenk.
U.S. Appl. No. 09/580,015, May 26, 2000, Schenk.
U.S. Appl. No. 09/579,690, May 26, 2000, Brayden.
U.S. Appl. No. 60/186,295, Mar. 1, 2000, Rasmussen et al.
U.S. Appl. No. 60/184,601, Feb. 24, 2000, Holtzman et al.
U.S. Appl. No. 09/497,553, Feb. 3, 2000, Schenk.
U.S. Appl. No. 60/169,687, Dec. 8, 1999, Chain.
U.S. Appl. No. 60/168,594, Nov. 29, 1999, Chalifour et al.
U.S. Appl. No. 09/441,140, Nov. 16, 1999, Solomon et al.
U.S. Appl. No. 60/139,408, Jun. 16, 1999, Raso.
U.S. Appl. No. 60/137,047, Jun. 1, 1999, Hirtzer.
U.S. Appl. No. 60/137,010, Jun. 1, 1999, Schenk.
U.S. Appl. No. 60/136,655, May 28, 1999, Brayden.
U.S. Appl. No. 09/322,289, May 28, 1999, Schenk.
U.S. Appl. No. 60/080,970, Jan. 11, 1999, Schenk.
U.S. Appl. No. 09/204,838, Dec. 3, 1998, Weiner.
U.S. Appl. No. 60/079,697, Mar. 27, 1998, Weiner et al.
U.S. Appl. No. 60/067,740, Dec. 2, 1997, Schenk.
U.S. Appl. No. 60/067,219, Dec. 3, 1997, Weiner et al.
U.S. Appl. No. 60/925,228, Apr, 18, 2007, Schroeter et al.
Agadjanyan et al., "Prototype Alzheimer's Disease Vaccine Using the Immunodominant B Cell Epitope From {beta}-Amyloid and Promiscuous T Cell Epitope Pan HLA DR-Binding Peptide," *J. Immunol.*, 174:1580-1586 (2005).

Aguzzi et al., "Prion research: the next frontiers," *Nature*, 389:795-798 (1997).
Aisen, P., "Inflammation and Alzheimer's Disease: Mechanisms and Therapeutic Strategies," *Gerontology*, 43:143-149 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "Inflammation and Alzheimer's disease," *Neurobiology of Aging*, 21:383-421 (2001).
Akiyama et al., "The amino-terminally truncated forms of amyloid β-protein in brain macrophages in the ischemic lesions of Alzheimer's disease patients," *Neuroscience Letters*, 219:115-118 (1996).
Alberts et al., eds. *Molecular Biology of the Cell, Third Edition*, chapter 23, pp. 1208-1209 (1994).
Alberts et al., eds. *Molecular Biology of the Cell, Third Edition*, chapter 23, pp. 1216-1218 (1994).
Alberts et al., *Molecular Biology of the Cell, 2nd Edition*, pp. 266-267, Garland Publishing Inc., New York (1989).
Allen et al, "Reversible posterior leukoencephalopathy syndrome after bevacizumab/FOLFIRI Regimen for Metastatic Colon Cancer," Arch. Neurol., 63(10): 1475-1478 (2006), abstract only.
American Type Culture Collection (ATCC) Search Results for "1KTR, 1ETZ, 1JRH", http://www.atcc.org/, pp. 1-3, Feb. 22, 2007.
Amit et al., "Three-Dimensional Structure of an Antigen-Antibody Complex at 2.8 Å Resolution," *Science*, 233:747-753 (1986).
Andersen et al., "Do nonsteroidal anti-inflammatory drugs decrease the risk for Alzheimer's disease?", *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Andrew et al., *Current Protocols in Immunology*, 2.7.1-2.9.8, John Wiley & Sons, Inc. (1997).
Ankarcrona et al., "Biomarkers for apoptosis in Alzheimer's disease," *Int. J. Geriatric Psychiatry*, 20:101-105 (2005).
Ard et al., "Scavenging of Alzheimer's Amyloid β-Protein by Microglia in Culture," *J. Neuroscience Research*, 43:190-202 (1996).
Arendiash et al., "Behavioral assessment of Alzheimer's transgenic mice following long-term Aβ vaccination: Task specificity and correlations between Aβ deposition and spatial memory" *DNA and Cell Biology*, 20(11):737-744 (2001).
Armour et al., "Recombinant human IgG molecules lacking Fcγ receptor I binding and monocyte triggering activites," *J. Immunol*, 29:2613-2624 (1999).
Askelof et al., "Protective immunogenicity of two synthetic peptides selected from the amino acid sequence of *Bordetella pertussis* toxin subunit S1," PNAS, 87:1347-1351 (1990).
Associated Press, "Immune cells may promote Alzheimer's, a study finds," *The Boston Globe* (Apr. 13, 1995).
Auclair et al., "Effect of Active Immunization Against Oestriadiol in Developing Ram Lambs on Plasma Gonadotrophin and Testosterone Concentrations, Time of Onset of Puberty and Testicular Blood Flow," *Journal of Reproduction and Fertility*, 104:7-16 (1995).
Auld et al., "Alzheimer's disease and the basal forebrain cholinergic system: relations to β-amyloid peptides, cognition, and treatment strategies," *Progress in Neurobiol.*, 68:209-245 (2002).
Avis, "Perenteral Preparations," *Remington's Pharmaceutical Sciences*, 17:1518-1519 (1985).
Bacskai et al., "Imaging of amyloid-Iβ deposits in brains of living mice permits direct observation of clearance of plaques with immunotherapy," *Nature Medicine*, 7(3):369-372 (2001).
Bacskai et al., "Non-Fc-mediated mechanisms are involved in clearance of amyloid-β in vivo by immunotherapy," *J. Neurosci.*, 22(18):7873-7878 (2002).
Balbach et al., "Amyloid fibril formation by Aβ$_{16-22}$, a seven-residue fragment of the Alzheimer's β-amyloid peptide, and structural characterization by solid state NMR," *Biochemistry*, 39:13748-13759 (2000).
Bales et al., "Administration of an Anti-Aβ Fab Fragment to APP$^{v717F}$ Transgenic Mice Reduces Neuritic Plague," Abstract P4-396, presented at Poster Session P4: Therapeutics and Therapeutic Strategies-Therapeutic Strategies, Amyloid-Based, *Neurogiology of Aging*, 25:S587 (2004).

Bales et al., "Cholinergic dysfunction in a mouse model of Alzheimer disease is reversed by an anti-Aβ antibody," *J. Clin. Invest.*, 116(3):825-832 (2006).

Bandlow et al., "Untersuchungen Zum Mechanismus Der Immunologischen Adjvanswirung des Vacciniavirus1,"*Archiv für due gesamte Virusfoschung*, 38:192-204 (1972), German article.

Bard et al., "Peripherally administered antibodies against amyloid β-peptide enter the central nervous system and reduce pathology in a mouse model of Alzheimer disease," *Nature Medicine*, 6(8):916-919 (2000).

Bard et al., "Epitope and isotype specificities of antibodies to β-amyloid peptide for protection against Alzheimer's disease-like neuropathology," *PNAS*, 100(4):2023-2028 (2003).

Barelli et al., "Characterization of New Polyclonal Antibodies Specific for 40 and 42 Amino Acid-Long Amyloid β Peptides: Their Use to Examine the Cell Biology of Presenilins and the Immunohistochemistry of Sporadic Alzheimer's Disease and Cerebral Amyloid Angiopathy Cases," Molecular Medicine, 3(10):695-707 (1997).

Barrow et al., "Solution Conformations and aggregational Properties of Synthetic Amyloid Beta-Peptides of Alzheimer's Disease. Analysis of Circular Dichroism Spectra " *J. Mol. Biol.*, 225(4):1075-1093 (1992).

Bauer et al., "Interleukin-6 and α-2-macroglobulin indicate an acute-phase state in Alzheimer's disease cortices," *FEBS Letters*, 285(1):111-114 (1991).

Beasley, "Alzheimer's traced to proteins caused by aging," Reuters, Apr. 20, 2001 7:56 PM ET.

Begley, "Delivery of Therapeutic Agents to the Central Nervous System: The Problems and the Possibilities," *Pharmacol. Therapy*, 104(1): 29-45 (Oct. 2004).

Bellotti et al., "Application of Monoclonal Anti-idiotypes in the Study of AL Amyloidosi: Therapeutic Implications," *Renal Failure*, 15(3):365-371 (1993). Abstract.

Bendig, "Humanization of Rodent Monoclonal Antibodies by CDR Grafting," *A Companion to Methods in Enzymology* 8:83-93 (1995).

Benjamini et al., from *IMMUNOLOGY A Short Course*, Second Edition, Chapter 4, Antibody Structure, pp. 49-65, 1991, published by Wiley-Liss, Inc., New York, New York.

Benjamini et al., from *IMMUNOLOGY A Short Course*, Second Edition, pp. 136-138, 143, 73-74, 372-373, and 400-401, 1991, published by Wiley-Liss, Inc., New York, New York.

Benkirane, et al, "Antigenicity and Immunogenicity of Modified Synthetic Peptides Containing D-Amino Acid Residues," *J. Biol. Chem.* 268(23):26279-26285 (1993).

Ben-Yedidia et al., "Design of peptide and polypeptide vaccines," *Current Opinion in Biotechnology*, 8:442-448 (1997).

Bercovici et al., "Chronic Intravenous Injections of Antigen Induce and Maintain Tolerance in T Cell Receptor-Transgenic Mice," *Eur. J. Immunol.* 29:345-354 (1999).

Biewenga et al., "Cleavage of Protein A-binding IgA1 with IgA1 Protease From Streptococcus Sanguls," *Immunol Commun.*, 12(5):491-500 (1983), abstract only.

Bickel et al., "Site Protected, Cationized Monoclonal Antibody Against Beta Amyloid as a Potential Diagnostic Imaging Technique for Alzheimer's Diseases " *Soc. for Neuroscience Abstracts*, 18:764 (1992).

Bickel et al., "Development and in Vitro Characterization of a Cationized Monoclonal Antibody against βA4 Protein: A Potential Probe for Alzheimer's Disease," *Bioconjugate Chem.*, 5:119-125 (1994).

Black et al., "A Single Ascending Dose Study of Bainezumab, A Humanized Monoclonal Antibody to Aβ, In AD," 9th *International Geneva/Springfield Symposium on Advances in Alzheimer Therapy*, 1 page (Apr. 20, 2006). Abstract only.

Bodmer et al., "Transforming Growth Factor-Beta Bound to Soluble Derivatives of the Beta Amyloid Precursor Protein of Alzheimer's Disease," Biochem. Biophys. Res. Comm. 171(2):890-897 (1990).

Blass, "Immunologic Treatment of Alzheimer's Disease," *New England J. Medicine*, 341(22):1694 (1999).

Bodmer et al., "Transforming Growth Factor-Beta Bound to Soluble Derivatives of the Beta Amyloid Precursor Protein of Alzheimer's Disease," Biochem. Biophys. Res. Comm. 171(2):890-897 (1990).

Borchelt et al., "Accelerated Amyloid Deposition in the Brains of Transgenic Mice Coexpressing Mutant Presenilin 1 and Amyloid Precursor Proteins," *Neuron*, 19:939-945 (1997).

Borenstein, S., "New Alzheimer's vaccine to be tested on people soon, Early experiments on mice halted condition; considered safe for humans," *Free Press*, Jul. 23, 2001.

Boris-Lawrie et al., "Recent advances in retrovirus vector technology," *Cur. Opin. Genetic Develop.*, 3:102-109 (1993).

Bork et al., "Go hunting in sequence databases but watch out for the traps," *Trends in Genetics*, 12(10):425-427 (1996).

Bork, P., "Powers and Pitfalls in Sequence Analysis: The 70% Hurdle," *Genome Research*, 10:398-400 (2000).

Borras-Cuesta et al., "Engineering of Immunogenic Peptides by Co-Linear Synthesis of Determinants Recognized by B and T Cells," Eur. J. Immunol., 17:1213-1215 (1987).

Brazil et al., "Effects of Incorporation of Immunoglobulin G and Complement Component C1q on Uptake and Degradation of Alzheimer's Disease Amyloid Fibrils by Microglia," *J. Biol. Chem.*, 275(22):16941-16947 (2000).

Brenner, S. E., "Errors in genome annotation," *Trends in Genetics*, 15(4):132-133 (1999).

Brice et al., "Absence of the amyloid precursor protein gene mutation (APP717 : Val->Ile) in 85 cases of early onset Alzheimer's disease," *J. Neurology, Neurosurg. Psychiatry*, 56:112-115 (1993).

Brinkman, "Splice Variants as Cancer Biomarkers," *Clinical Biochemisrty*, 37(7):584-594 (2004).

Britt et al., "Formulation of an immunogenic human cytomegalovirus vaccine: responses in mice," *J. Infect. Dis.*, 171:18-25 Abstract (1995).

Broadwell et al., "Serum proteins bypass the blood-brain fluid barriers for extracellular entry to the central nervous system," *Exp. Neurol.*, 120(2):245-263 (1993).

Brookmeyer et al., "Projections of Alzheimer's Disease in the United States and the Public Health Impact of Delaying Disease Onset,"*Am. J. Public Health*, 88:1337-1342 (1998).

Burdick et al., "Assembly and aggregartion properties of synthetic Alzheimer's A4/β amyloid peptide antigens," *J. Biol. Chem.*, 267:546-555 (1992).

Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).

Buttini et al., "β-Amyloid Immunotherapy Prevents Synaptic Degeneration in a Mouse Model of Alzheimer's Disease," *The Journal of Neuroscience*, 25(40):9096-9101 (2005).

Cameron, "Recent Advances in Transgenic Technology," *Molecular Biotechnology*, 7:253-265 (1997).

Caputo et al., "Therapeutic approaches targeted at the amyloid proteins in Alzheimer's disease," *Clin. Neuropharm.*, 15:414A-414B (1992).

Casadesus et al., "The Estrogen Myth: Potential Use of Gonadotropin-Releasing Hormone Agonists for the Treatment of Alzheimer's Disease," *Drugs R D*, 7(3):187-193 (2006).

Casey, S.O., "Posterior Reversible Encephalopathy Syndrome: Utility of Fluid-attenuated Inversion Recovery MR Imaging in the Detection of Cortical and Subcortical Lesions " *Amer J Neuroradiol*, 21:1199-1206 (2006).

Castillo et al., "Amylin/Islet Amyloid Polypeptide: Biochemistry, Physiology, Patho-Physiology," *Diabete & Metabolisme (Paris)*, 21:3-25 (1995).

Cassell et al., "Demography and Epidemiology of Age-Associated Neuronal Impairment," chapter 4, pp. 31-50 from *Funcitional Neurobiology of Aging*, Hof et al., eds., Academic Press (2001).

Casset et al., "A Peptide Mimetic of an Anti-CD4 Monoclonal Antibody by Rational Design," *Biochemical and Biophysical Research Commiunications*, 307:198-205 (2003).

Center for Biologics Evaluation and Research, U.S. Food and Drug Administration, Thimerosal in Vaccines (Mercury in Plasma-Derived Products), web site contents found at : http://www.fda.gov/cber/vaccine/thimerosal.htm, last updated May 16, 2002.

Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).
Chang et al., "Adjuvant activity of incomplete Freund's adjuvant," *Advanced Drug Delivery Reviews*, 32:173-186 (1998).
Chao et al., "Transforming Growth Factor-β Protects human Neurons Against β-AmyloidInduced Injury," *Soc. Neurosci. Abstracts*, 19:513-7 (1993).
Chapman, "Model behavior," *Nature*, 408:915-916 (2000).
Check, "Battle of the Mind," *Nature*, 422:370-372 (2003).
Check, "Nerve Inflamtion Halts Trail for Alzheimer's Drugs," Nature, 415:462 (2002).
Chemical Abstract database, Abstract of "Injection of Newborn Mice with Seven Chemical Adjuvants to Help Determine Their Safety in Use in Biologicals," Chemical Abstract database, 75:242 (1971).
Chimicon International, "Mouse Anti-Amyloid Beta Protein Monoclonal Antibody," Catalog # MAB1561 (2003-2005).
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease" *Nature*, 408(6815):975-979 (2000).
Chen et al., "An Antibody to β Amyloid Precursor Protein Inhibits Cell-substratum Adhesion in Many Mammalian Cell Types," *Neuroscience Letters*, 125:223-226 (1991).
Chen et al., "Selection and Analysis of an Optimized Anti-VEGF Antibody: Crystal Structure of an Affinity-matured Fab in Complex with Antigen," *J. Mol. Biol.*, 293:865-881 (1999).
Chishti et al., "Early-onset Amyloid Deposition and Cognitive Deficits in Transgenic Mice Expressing a Double Mutant Form of Amyloid Precursor Protein 695," *J. Biol.Chem.*, 276(24):21562-70 (2001).
Choi et al., "A Generic Intron Increases Gene Expression in Transgenic Mice," Molecular and Cellular Biology, 11(6):3070-3074 (1991).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biochemistry*, 42(44):12749-12760 (2003).
Chung et al., "Uptake, Degradation, and Release of Fibrillar and Soluble Forms of Alzheimer's Amyloid (β-Peptide by Microglial Cells," *J. Biol. Chem.*, 274(45):32301-32308 (1999).
Cirrito et al., "Amyloid β and Alzheimer disease therapeutics: the devil may be in the details," *J. Clin. Invest.*,112:321-323 (2000).
Citron et al., "Evidence that the 42- and 40- amino acid forms of amyloid-β protein are generated from the (β-amyloid precursor protein by different protease activities," *PNAS*, 93(23):13170-13175 (1996).
Citron, M., "Alzheimer's disease: treatments in discovery and development," *Nat. Neurosci.* 5:1055-1057 (2002).
Clark et al., *Chemical Immunology Antibody Engineering IgG Effector Mechanisms*, 65:88-110 (1997).
Clayton et al., "Synucleins in Synaptic Plasticity and Neurodegenerative Disorders," *J. Neurosci. Res.*, 58:120-129 (1999).
Co et al., "Chimeric and humanized antibodies with specificity for the CD33 antigen," *J. Immunol.*, 148:1149-1154 (1992).
Coico et al., *Immunology A Short Course*, Fifth Edition, pp. 18-24 (2003).
Colman, "Effects of Amino Acid Sequence Changes On Antibody-Antigen Interactions," *Research in Immunology*, 145:33-36 (1994).
Coloma et al., "Transport Across the Primate Blood-Brain Barrier of a Genetically Engineered Chimeric Monoclonal Antibody to the Human Insulin Receptor," *Pharm. Res.*, 17:266-274 (2000).
Colombian Patent Application No. 98071271, Technical Opinion of Jean Paul Vernot submitted on Jun. 22, 2005 as evidence with the brief amending the nullity action (with English translation) (drafted Nov. 2004).
Comery et al., "Passive Immunization Against β-Amyloid Leads to Acute Cognition Improvement," *Society for Neuroscience*, abstract, Washington DC, 11/12-16/05.

Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).
Corcoran et al., "Overexpression of hAPPswe Impairs Rewarded Alternation and Contextual Fear Conditioning in a Transgenic Mouse Model of Alzheimer's Disease," Learn Mem. 9(5):243-252:2000.
Cordell, B., "β-Amyloid formation as a potential therapeutic target for Alzheimer's disease," *Ann. Rev. Pharmacol. Toxicol.*, 34:69-89 (1994).
Corey-Bloom et al., "Clinical features distinguishing large cohorts with possible AD, probable AD, and mixed dementia," *J. Am. Geriatr. Soc.*, 41(1):31-37 Abstract (1993).
Costa et al., "Immunoassay for transthyretin variants associated with amyloid neuropathy," *Scand. J. Immunol.*, 38:177-182 (1993).
Cox et al., "Adjuvants—a classification and review of their modes of action," *Vaccine*, 15(3):248-256 (1997).
Cribbs et al, "All-D-Erantiomers of Beta-Amyloid Exhibit Similar Biological Properties to All-L-Beta-Amyloids," *J. Biol. Chem.*, 272:7431-7436 (1997).
Daly, et al., "Detection of the membrane-retained carboxy-terminal tail containing polypeptides of the amyloid precursor protein in tissue from Alzheimer's Disease brain," *Life Sci.*, 63:2121-2131 (1998).
Das et al., "Amyloid-β Immunization Effectively Reduces Amyloid Deposition in FcRy Knock-Out-Mice," *J. Neuroscience*, 23(24):8532-8538 (2003).
Das et al., "Reduced effectiveness of Aβ-42 immunization in APP transgenic mice with significant amyloid deposition," *Neurobiology of Aging*, 22:721-727 (2001).
Database Geneseq, "Nucleotide Sequence of a Variable Heavy Chain of IgG4," EBI Accession No. Gsn:ADZ51216 (2005).
Davis, S. S., "Nasal Vaccines," *Advanced Drug Delivery Reviews*, 51:21-42 (2001).
De Felice et al., "β-Amyloid production, aggregation, and clearance as targets for therapy in Alzheimer's disease," *Cell Mol. Neurobiol.*, 22(5/6):545-563 (2002).
De La Cruz et al, "Immumogenicity [sic] and Epitope Mapping of Foreign Sequences via Genetically Engineered Filamentous Phage," *J Biol Chem*, 263(9):4318-4322 (1988).
De Lustig et al., "Peripheral Markers and Diagnostic Criteria in Alzheimer's Disease: Critical Evaluations," *Rev. In Neurosciences*, 5:213-225 (1994).
Demattos et al., "Peripheral anti-Aβ antibody alters CNS and plasma clearance and decreases Aβ burden in a mouse model of Alzheimer's disease," *PNAS*, 98(15):8850-8855 (2001).
Demattos et al., "Peripheral Anti Aβ Antibody Alters CNS and Plasma Aβ Clearance and Decreases Brain Aβ Burden in a Mouse Model of Alzheimer's Disease," published online before print Jul. 3, 2001 at 10.1073/pnas.151261398; *PNAS*, 98(15):8850-8855 (2001).
Demattos et al., "Plaque-associated disruption of CSF and plasma amyloid-β (Aβ) equilibrium in a mouse model of Alzheimer's disease," *J. Neurochem.*, 81:229-236 (2002).
Demattos et al., "Brain to plasma amyloid-β efflux: a measure of brain amyoid burden in a mouse model of Alzheimer's disease," *Science*, 295(5563):2264-2267 (2002).
Dewitt et al., "Astrocytes regulate microglial phagocytosis of senile plaque cores of Alzheimer's disease," *Experimental Neurology*, 149:329-340 (1998).
Dialog/Derwent, Abstract of WPI Acc No: 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Derwent WPI database (1997).
Dialog/Derwent, Abstract of WPI Acc No: 1995-261292/199534: Novel monoclonal antibody against human high-affinity IgE receptor—and DNA fragment encoding the MAb, for the specific identification of human Fc-epsilon RI, Derwent WPI database (1995).
Dickey et al., "Duration and specificity of humoral immune responses in mice vaccinated with the Alzheimer's disease-associated β-amyloid 1-42 peptide," *DNA and Cell Biology*, 20(11):723-729 (2001).

Dickson et al., "Neuroimmunology of Alzheimer's disease: a conference report," *Neurobiology of Aging*, 13(6):793-798 (1992), abstract only.

Dictionary.com definition of "prophylactic", pp. 1-3 downloaded from internet Oct. 12, 2005.

Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).

Diomede et al., "Activation effects of a prion protein fragment [PrP-(106-126)] on human leucocytes," *Biochem. J.*, 320:563-570 (1996).

Disis et al., "Granulocyte-macrophage colony-stimulating factor: An effective adjuvant for protein and peptide-based vaccines," *Blood*, 88(1):202-210 (1996).

Dodart, "Immunotherapy for Alzheimer's disease: will vaccination work?," *Trends in Molecular Medicine*, 9(3):85-87 (2003).

Dodart et al., "Immunization reverses memory deficits without reducing brain Aβ burden in Alzheimer's disease model," *Nat. Neurosci.*, 5(5):452-457 (2002).

Dodel et al., "Immunotherapy for Alzheimer's disease," *Lancet Neurol.*, 2(4):215-220 (2003).

Doerks et al., "Protein annotation: detective work for function prediction" *Trends in Genetics*, 14(6):248-250 (1998).

Donnelly, "New Developments in Adjuvants," *Mechanism of Ageing and Development*, 93:171-177 (1997).

Dovey et al., "Functional gamma-secretase inhibitors reduce beta-amyloid peptide levels in brain," *J. Neurochem.*, 76(1):173-181 (2001).

Drew et al., "Vaccination by cholera toxin conjugated to a herpes simplex virus type 2 glycoprotein D peptide," *Journal of General Virology*, 73:2357-2366 (1992).

Du et al., "Reduced levels of amyloid beta-peptide antibody in Alzheimer disease," *Neurology*, 57(5):801-5 (2001).

Du et al., "$\alpha_2$-Macroglobulin as a β-Amyloid Peptide-Binding Plasma Protein," *J. Neurochemistry*, 69(1):299-305 (1997).

Duff et al., "Mouse model made," *Nature*, 373:476-477 (1995).

Duff et al., "Increased amyloid-β42(43) in brains of mice expressing mutant presenilin 1," *Nature*, 383(6602):710-713 (1996).

Dumery et al., "β-Amyloid protein aggregation: its implication in the physiopathology of Alzheimer's disease," *Pathol. Biol.*, 49:72-85 (2001).

Eck et al., *Goodman and Gilman's The pharmacological basis of therapeutics*, Chapter 5, pp. 77-101 (1996).

Ecuador Patent Application No. SP 98-2764, English translation of Expert Report submitted Apr. 19, 2007 in support of the Appeal filed on Jul. 29, 2005.

Ecuadorian Search Report of Jul. 2, 2009 for Ecuador Patent Application No. SP 03-4685.

El-Agnaf et al., "The influence of the central region containing residues 19-25 on the aggregation properties and secondary structure of Alzheimer's beta-amyloid peptide" *Eur. J. Biochem.*, 256(3):560-569 (1998).

Elan, "Elan and AHP Provide an Update on the Phase 2A Clinical Trial of AN-1792," Press Release. (Jan. 18, 2002).

Elan, "Elan and Wyeth Provide Update on Status of Alzheimer's Collaboration," Press Release (Mar. 1, 2002).

Elizan et al., "Antineurofilament antibodies in a postencephalitic and idiopathic Parkinson's disease," *J. Neurol. Sciences*, 59:341-347 (1983).

Eriksen et al., "NSAIDs and enantiomers of flurbiprofen target y-secretase and lower Aβ42 in vivo," *J. Clin. Invest.*, 112(3):440-449 (2003).

Esiri, "Is an effective immune intervention for Alzheimer's disease in prospect?" *Trends in Pharm. Sci.*, 22:2-3 (2001).

Esler et al., "Point substitution in the central hydrophobic cluster of a human β-amyloid congener disrupts peptide folding and abolishes plaque competence," *Biochemistry*, 35:13914-13921 (1996).

European Search Report of May 22, 2006 for European Application 06075704.4-2107.

European Search Report of May 22, 2006 for European Application 06075479.3-2107.

Extended European Search Report of Dec. 18, 2008 for European Application 05812436.6-1212.

European Search Report of Jan. 16, 2007 for European Application 04776252.1-2405.

European Examination Report of Sep. 23, 2008 for European Application 04776252.1-2405.

European Examination Report of Mar. 9, 2007 for European Application 01995364.5-1222.

European Examination Report of Sep. 26, 2007 for European Application 04720353.4-1222.

European Examination Report as part of Dec. 8, 2008 communication for European Application 04720353.4.

European Examination Report of Oct. 8, 2007 for European Application 01995364.5-1222.

European Examination Report of Nov. 20, 2008 for European Application 08011409.3.

Family and legal status of EP0613007, Inpadoc Search (2009).

Felsenstein et al., "Processing of the β-amyloid precursor protein carrying the familial, Dutch-type, and a novel recombinant C-terminal mutation," *Neuroscience Letters*, 152:185-189 (1993).

Felsenstein et al., "Transgenic Rat and In-Vitro Studies of B-Amyloid Precursor Protein Processing:" *Alzheimer's and Parkinson's Diseases*, Hanin et al. Ed., pp. 401-409, Plenum Press, New York, (1995).

Finch et al., "Evolutionary Perspectives on Amyloid and Inflammatory Features of Alzheimer Disease," *Neurobiology of Aging*, 17(5):809-815 (1996).

Findeis et al, "Modified peptide inhibitors of amyloid B-peptide polymerization," *Biochemistry*, 38:6791-6800 (1999).

Findeis, M. A., "Approaches to discovery and characterization of inhibitors of amyloid β-peptide polymerization," *Biochem. Biophys. Acta*, 1502(1):76-84 (2000).

Fisher et al., "Expression of the amyloid precursor protein gene in mouse oocytes and embryos," *PNAS*, 88:1779-1782 (1991).

Flanders et al., "Altered expression of transforming growth factor-β in Alzheimer's disease," *Neurology*, 45:1561-1569 (1995).

Flood et al., "An amyloid β-Protein fragment, A β 12-28J, equipotently impairs post-training memory processing when injected into different limbic system structures," *Brain Res*, 663(2):271-276 (1994).

Flood, et al, "Topography of a binding site for small amnestic peptides deduced from structure-activity studies: Relation to amnestic effect of amyloid B protein," *PNAS*, 91:380-384 (1994).

Fonseca et al., "The Presence of Isoaspartic Acid in β-Amyloid Plaques Indicates Plaque Age," *Experimental Neurology*, 157(2):277-288 (1999).

Foote et al., "Antibody Framework Residues Affecting the Conformation of the Hypervariable Loops," *J. Mol. Biol.*, 224:487-499 (1992).

Fox et al., "Presymptomatic cognitive deficits in individuals at risk of familial Alzheimer's disease," *Brain*, 121:1631-1639 (1998).

Fraglone et al., Familial cerebral amyloid angiopathy related to stroke and dementia. Amyloid 8(Suppl 1):36-42 (2001), abstract only.

Frautschy et al., "Effects of injected Alzheimer β-amyloid cores in rat brain," *PNAS* 88:8362-8366 (1991).

Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).

Frenkel et al., "Generation of auto-antibodies towards Alzheimer's disease vaccination," *Vaccine*, 19:2615-2619 (2001).

Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).

Frenkel et al., "Immunization against Alzheimer's β-amyloid plaques via EFRH phage administration," *PNAS*, 97:11455-11459 (2000).

Frenkel et al., "N-terminal EFRH sequence of Alzheimer's 6-amyloid peptide represents the epitope of its anti-aggregating antibodies," *J. of Neuroimmunology*, 88:85-90 (1998).

Frenkel, et al., "Modulation of Alzheimer's β-amyloid neurotoxicity by site-directed single chain antibody," *J. of Neuroimmunology*, 106:23-31 (2000).

Frenkel et al., "Reduction of β-amyloid plaques in brain of transgenic mouse model of Alzheimer's disease by EFRH-phage immunization," *Vaccine*, 21(11-12):1060-1065 (2003).

Frenkel et al., "Towards Alzheimer's β-amyloid vaccination," *Biologicals*, 29(3-4):243-247 (2001).

Friedland et al., "Development of an anti-Aβ monoclonal antibody for in vivo imaging of amyloid angiopathy in Alzheimer's disease," *Mol. Neurology*, 9:107-113 (1994).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York, 826:242-247 (1997).

Fukutani et al., "Cerebeller pathology in sporadic and familial Alzheimer's disease including APP 717 (Val->Ile) mutation cases: A morphometric investigation," *J. Neurologic Sci.*, 149:177-184 (1997).

Furlan et al., "Vaccination with amyloid-β peptide induces autoimmune encephalomyelitis in C57/BL6 mice," *Brain*, 126:285-291 (2003).

Games et al., "Alzheimer-type neuropathology in transgenic mice overexpressing V717F β-amyloid precursor protein," *Nature*, 373(6514):523-527 (1995).

Games et al., "Prevention and Reduction of AD-type Pathology in PDAPP Mice Immunized with $A\beta_{1-42}$," *Annals of the New York Academy of Science*, 920:274-284 (2000).

Gandy et al., "Amyloidogenesis in Alzheimer's disease: some possible therapeutic opportunities," *TiPS*, 13:108-113 (1992).

Gardella et al., "Intact Alzheimer amyloid precursor protein (APP) is present in platelet membranes and is encoded by platelet mRNA," *Biochem. Biophys. Res. Comm.*, 173:1292-1298 (1990).

Gaskin et al., "Human antibodies reactive with beta-amyloid protein in Alzheimer's disease," *J. Exp. Med.*, 177:1181-1186 (1993).

Gauthier et al., "Alzheimer's Disease: Current Knowledge, Management and Research," Can. Med. Assoc. J., 157:1047-1052 (Oct. 15, 1997).

Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).

Gelinas et al., "Immunotherapy for Alzheimer's disease," *PNAS*, 101(suppl. 2):14657-14662 (2004).

Genbank Accession No. AAA69734, Schroeder et al., "Immunoglobulin heavy chain [*Homo sapiens*]", Anti-DNA immunoglobulin light chain IgG [*Mus musculus*],Jul. 11, 1995.

Genbank Accession No. AAB35009.1, Wang et al., "Antiidiotypic Ig 1F7 Light Chain Variable Region [Human, 1F7 Hybridoma Cells, Peptide Partial, 120aa]," Oct. 28, 1995.

Genbank Accession No. AAB48800, "Anti-DNA immunoglobulin light chain IgG [*Mus musculus*]," Sep. 14, 2001.

Genbank Accession No. AAD00856.1, "Igm Heavy Chain Variable Region [*Homo Sapiens*]," Jul. 31, 2001.

Genbank Accession No. BAC01733, Akahori et al., "Immunoglobulin kappa light chain VLJ region [*Homo sapiens*]", Jul. 2, 2002.

Genbank Accession No. CAA46659, "IgE antibody light chain(VJ)," Jun. 15, 1993.

Genbank Accession No. X65775.1, "*M.musculus* DNA for IgE antibody light chain (VJ)," Jun. 15, 1993.

Genbank Accession No. AAD26773, "Immunoglobulin heavy chain VH3609-JH3 region [*Mus musculus*]," Apr. 22, 1999.

Geylis et al., "Immunotherapy of Alzheimer's disease 9AD): From murine models to anti-amyloid beta 9Ab) human monoclonal antibodies," *Autoimmunity Rev.*, 5:33-39 (2000).

Ghetie et al., "CD4 Peptide-Protein Conjugates, But Not Recombinant Human CD4, Bind to Recombinant gp120 From the Human Immunodeficiency Virus in the Presence of Serum From AIDS Patients.," Proc. Natl. Acad. Sci., 88:5690-5693 (1991).

Ghiso et al., "Epitope map of two polyclonal antibodies that recognize amyloid lesions in patients with Alzheimer's disease," *Biochem. J.*, 282 (Pt 2):517-522 (1992).

Gibson et al., "Abnormalities in Alzheimer's Disease Fibroblasts Bearing the APP670/671 Mutation," *Neurobiology of Aging*, 18(6):573-580 (1997).

Gilman, S. et al., "Clinical Effects of Aβ Immunization (AN1792) in Patients with AD in an Interrupted Trial," *Neurology*, 64(9):1553-1562 (2005).

Giulian et al., "Specific domains of β-amyloid from Alzheimer plaque elicit neuron killing in human microglia," *J Neurosci.*, 16(19):6021-6037 (1996).

Giulian, et al., "The HHQK Domain of b-Amyloid Provides a Structural Basis for the Immunopathology of Alzheimer's Disease," *J. Biol. Chem.*, 273:29719-29726 (1998).

Glenn et al., "Skin immunization made possible by cholera toxin," *Nature*, 391:851 (1998).

Glenner et al., "Alzheimer's Disease and Downs Syndrome: Sharing of A Unique Cerebrovascular Amyloid Fibril Protein," *Biochem. Biophys. Res. Comm.*, 122(3): 1131-1135 (1984).

Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).

Goate et al., "Segregation of a myloid mutation in the myloid precursor protein gene with familial Alzheimer's disease," *Nature*, 349:704-706 (1991).

Goldfarb et al., "The Transmissible Spongiform Encephalopathies," *Ann. Rev. Med.*, 46:57-56 (1995).

Golding et al., "Vaccine Strategies: Targeting Helper T Cell Responses " *Annals New York Academy of Sciences*, 31:126-137 (1995).

Goldsby et al., "Vaccines," Chapter 18 from *Immunology*, $4^{th}$ *Edition*, W.H. Freeman and Company, New York, pp. 449-465 (2000).

Goldsteins et al., "Exposure of cryptic epitopes on transthyretin only in amypoid and in amyloidogenic mutants," *PNAS*, 96:3108-3113 (1999).

Gong et al., "Alzheimer's disease-affected brain: presence of oligomeric Aβ ligands (ADDLs) suggests a molecular basis for reversible memory loss," *PNAS*, 100(18):10417-10422 (2003).

Gonzales-Fernandez et al., "Low antigen dose favors selection of somatic mutants with hallmarks of antibody affinity maturation," *Immunology*, 93:149-153 (1998).

Gorevic et al., "Ten to fourteen residue peptides of Alzheimer's disease protein are sufficient for Amyloid fibril formation and its characteristic X ray diffraction pattern" *Biochem. And Biophy. Res. Commun.*, 147(2):854-862 (1987).

Gortner, *Outlines of Biochemistry*, pp. 322-323, John Wiley & Sons, Inc., New York (1949).

Gozes et al., "Neuroprotective strategy for Alzheimer disease: Intranasal administration of a fatty neuropeptide," *PNAS*, 93:427-432 (1996).

Gravina et al., "Amyloid β Protein (Aβ) in Alzheimer's Disease," *J. Biol. Chem.*, 270(13):7013-7016 (1995).

Greenberg et al., "Alzheimer disease's double-edged vaccine," *Nat. Med.*, 9(4):389-390 (2003).

Gross et al., "Microvascular specializations promoting rapid interstitial solute dispersion in nucleus tractus solitarius," *Am J Physiol Regul Inteor Comp Physiol*, 259:R1131-R1138 (1990).

Grubeck-Loebenstein, et al., "Immunization with β-amyloid: could T-cell activation have a harmful effect?", *TINS*, 23:114 (2000).

Gupta et al., "Adjuvants for human vaccines—current status, problems, and future prospects," *Vaccine*, 13(14):1263-1275 (1995).

Gupta et al., "Differences in the immunogenicity of native and formalized cross reacting material (CRM197) of diphtheria toxin in mice and guinea pigs and their implications on the development and control of diphtheria vaccine based on CRMs," *Vaccine*, 15(12/13): 1341-1343 (1997).

Haass et al. "Amyloid beta-peptide is produced by cultured cells during normal metabolism," *Nature*, 359(6393):322-325 (1992).

Haass et al., "Protofibrils, the unifying toxic molecule of neurodegenerative disorders?," *Nature Neuroscience*, 4(9):859-860 (2001).

Haass, C., "New hope for Alzheimer disease vaccine," *Nat Med.*, 8(11):1195-1196 (2002).

Haga et al., "Synthetic Alzheimer Amyloid β/A4 peptides enhance production of complement C3 component by cultured microglial cells," *Brain Research*, 601:88-94 (1993).

Hamilton, "Molecular Engineering: Applications to the Clinical Laboratory," Clin. Chem. 39(9):1988-1997 (1993).

Hanan and Solomon, "Inhibitory effect of monoclonal antibodies on Alzheimer's β-amyloid peptide aggregation," *Int. J. Exp. Clin. Invest.*, 3:130-133 (1996).

Hanes et al., "New advances in microsphere-based single-dose vaccines," *Advanced Drug Delivery Reviews*, 28: 97-119 (1997).

Hara et al., "Development of a safe oral Aβ vaccine using recombinant adeno-associated virus vector for Alzheimer's disease," *J. Alzheimer's Disease*, 6:483-488 (2004).

Hardy, "Amyloid, the presenilins and Alzheimer's disease," *TINS*, 20(4): 154-159 (1997).

Hardy, John, "New Insights into the Genetics of Alzheimer's Disease," *Annals of Med.*, 28:255-258 (1996).

Harigaya, et al., "Modified myloid 13 protein ending at 42 or 40 with different solubility accumulates in the brain of Alzheimer's disease," *Biochem. Biophys. Res. Comm.*, 211:1015-1022 (1995).

Harlow et al., eds., *Antibodies: A Laboratory Manual*, pp. 71-82 (1988).

Harlow et al., eds., *Antibodies: A Laboratory Manual*, p. 98 (1988).

Harlow et al., eds., *Antibodies: A Laboratory Manual*, pp. 139-195 (1988).

Harrington et al., "Characterization of an epitope specific to the neuron-specific isoform of human enolase recognized by a monoclonal antibody raised against a synthetic peptide corresponding to the C-terminus of β / A4-protein," *Biochimica Biophysica Acta*, 1158:120-128 (1993).

Hazama, et al., "Intranasal Immunization Against Herpes Simplex Virus Infection by Using a Recombinant Glycoprotein D Fused With Immunomodulating Proteins, the B Subunit of Escherichia Coli Heat-Labile Enterotoxin and Interleukin-2," *Immunology*, 78:643-649 (1993).

He et al., "Humanization and pharmacokinetics of a monoclonal antibody with specificity for both E- and P- selectin," *J. Immunol*, 160:1029-1035 (1998).

Helmuth, "Further Progress on a β-Amyloid Vaccine," *Science*, 289:375 (2000).

Hellman et al., "Allergy Vaccines—A Review of Developments," *Clin. Immunother.*, 6(2):130-142 (Aug. 1996).

Herlyn et al., "Monoclonal antibodies in cell-mediated cytotoxicity against human melanoma and colorectal carcinoma*," *Eur. J. Immunol.*, 9:657-659 (1979).

Hermanson et al., "Amino Acids as Spacers," *Immobilized Affinity Ligand Techniques*, section 3.1.1.5:150-152 (1992).

Hezareh et al., "Effector Function Activities of a Panel of Mutants of a Broadly Neutralizing Antibody against Human Immunodeficiency Virus Type 1," *Journal of Virology*, 24(75):12161-12168 (2001).

Hilbich et al., "Aggregation and secondary structure of synthetic amylold βA4 peptides of Alzheimer's disease," *J. Mol. Biol.*, 218:149-163 (1991).

Hilbich et al., "Substitutions of hydrophobic amino acid reduce the amyloidogenicity of Alzheimer's disease βA4 peptides" *J. Mol. Biol.*, 228:460-473 (1992).

Hilbich et al., "Human and rodent sequence analogs of Alzheimer's myloid βA4 share similar properties and can be solubilized in buffers of pH 7.4," *Eur. J. Biochem.*, 201:61-69 (1991).

Hillen-Maske et al., "Konichalcit", *Rompp Chemie Lexilkon*, 9th edition, p. 2322 (1990).

Hirschfield et al., "Amylodiosis: new strategies for treatment " *Int. J. Biochem. & Cell Biol.*, 35:1608-1613 (2003).

Hock et al., "Antibodies against β-Amyloid Slow Cognitive Decline in Alzheimer's Disease," *Neuron*, 38:542-554 (2003).

Hock et al., "Generation of antibodies specific for β-amyloid by vaccination of patients with Alzheimer disease," *Nat. Med.*, 8(11):1270-1275 (2002).

Hogarth, Fc Receptors Are Major Mediators of Antibody Based Inflammation in Autoimmunity, *Current Opinion in Immunology*, 14:798-802 (2002).

Holmes et al., "Long-term Effects of Aβ$_{42}$ Immunisation in Alzheimer's Disease: Follow-up of a Randomised, Placebo-controlled Phase I Trial, " *Lancet*, 372: 216-223 (2008).

Holtzman et al., "Aβ immunization and anti-Aβ antibodies: potential therapies for the prevention and treatment of Alzheimer's disease," *Advanced Drug Delivery Reviews*, 54:1603-1613 (2002).

Hopp et al., "Prediction of protein antigenic determiniants from amino acid sequences," Proc. Natl. Acad. Sci. USA 78:3824-3828 (1981).

Hsiao et al., "Correlative Memory Deficits, Aβ Elevation, and Amyloid Plaques in Transgenic Mice," *Science*, 274: 99-102 (1996).

Huang et al., "Amyloid β-Peptide Possesses a Transforming Growth Factor-β-Activity," *The Journal of Biological Chemistry*, 273(42):27640-27644 (Oct. 16, 1998).

Huberman et al., "Correlation of cytokine secretion by mononuclear cells of Alzheimer's patients and their disease stage," *J. Neuroimmunology*, 52:147-152 (1994).

Hudson et al., "Antibody as a Probe," *Practical Immunology*, Chapter 2, pp. 34-85 (1989).

Human Immunology & Cancer Program brochure, from The University of Tennessee Medical Center/ Graduate School of Medicine, Knoxville, Tennessee.

Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6): 726-732 (1995).

Hyman et al., "Molecular Epidemiology of Alzheimer's Disease," *N. E. J. Medicine*, 333(19):1283-1284 (1995).

Hyslop et al., " Will Anti-amyloid Therapies Work for Alzheimer's Disease?," *Lancet*, 372:180-182 (2008).

Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).

Idusogie et al., "Mapping of the C1q Binding Site on Rituxan, a Chimeric Antibody with a Human IgG1 Fc," *J. Immunology*, 164:4178-4184 (2000).

Ikeda, et al., "Immunogold labeling of cerebrovascular and neuritic plaque Amyloid fibrils in Alzheimer's disease with an anti-β protein monoclonal antibody," *Lab. Invest.*, 57:446-449 (1987).

Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).

Irizarry et al., "Alzheimer disease therapeutics," *J. Neuropathol. Exp. Neurol.*, 60(10):923-928 (2001).

Itagaki et al., "Relationship of microglia and astrocytes to myloid deposits of Alzheimer's disease," *J. Neuroimmunology*, 24:173-182 (1989).

Iwatsubo et al., "Visualization of Aβ42(43) and Aβ40 in Senile Plaques with End-Specific Aβ Monoclonals: Evidence That an Initially Deposited Species Is Aβ 42(43)," *Neuron*, 13:45-53 (1994).

Jahrling et al., "Opsonization of Alphaviruses in Hamsters," *J. Medical Virology*, 12:1-16 (1983).

Jakes et al., "Characterisation of an Antibody Relevant to the Neuropathology of Alzheimer Disease," *Alzheimer Disease and Associated Disorders*, 9(1):47-51 (1995).

Janeway et al., *Immunobiology*, 3rd edition, pp. 8:18-8:19 (1997).

Janeway et al., *Immunobiology*, 3rd edition, pp. 2:7, 2:9, 2:12, 8:16-8:17, 12:43 (1997).

Jansen et al., "Immunotoxins: Hybrid Molecules Combining High Specificity and Potent Cytotoxicity," *Immun. Rev.*, 62: 185-216 (1982).

Jansen et al., "Use of Highly Encapsulated Streptococcus pneumoniae Strains in a Flow-Cytometric Assay for Assessment of the Phagocytic Capacity of Serotype-Specified Antibodies," *Clinical & Diagnostic Lab. Immunol.*, 5(5):703-710 (1998).

Janus et al., "A beta peptide immunization reduces behavioural impairment and plaques in a model of Alzheimer's disease," *Nature*, 408(6815):979-982 (2000).

Janus et al., "Transgenic mouse models of Alzheimer's Disease," *Physiol. Behav.*, 73(5):873-886 (2001).

Jarrett et al., "The Carboxy Terminus of the β Amyloid Protein is Critical for the Seeding of Amyloid Formation: Implications for the Pathogenesis of Alzheimer's Disease," *Biochemistry*, 32:4693-4697 (Nov. 5, 1993).

Jen, et al., "Preparation and purification of antisera against different regions or isoforms of b-amyloid precursor protein," *Brain Research Protocols*, 2:23-30 (1997).

Jennings, "Review of Selected Adjuvants Used in Antibody Production," *ILAR Journal*, 37(3) (1995).
Joachim et al., "Antibodies to Non-beta Regions of the Beta-amyloid Precursor Protein Detect a Subset of Senile Plaques," *Am. J. of Pathology*, 138:373-384 (1991).
Jobling et al., "Analysis of structure and function of the B subunit of cholera toxin by the use of site-directed mutagenesis," *Molecular Microbiology*, 5(7):1755-1767 (1991).
Johnson-Wood et al., "Amyloid precursor protein processing and $A\beta_{42}$ deposition in a transgenic mouse model of Alzheimer disease," *PNAS*, 94(4):1550-1555 (Feb. 18, 1997).
Johnstone et al., Nuclear and Cytoplasmic Localization of the β-Amyloid Peptide (1-43) in Transfected 293 Cells, *Biochem. Biophys. Res. Comm.*, 220:710-718 (1996).
Jorbeck et al., "Artificial Salmonella Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).
Jung et al., "Alzheimer's Beta-amyloid Precursor Protein Is Expressed on the Surface of Immediately Ex Vivo Brain Cells: a Flow Cytometric Study," *J. Neurosci. Res.*, 46(3):336-348 (1996).
Kajkowski et al., "β-Amyloid Peptide-induced Apoptosis Regulated by a Novel Protein Containing a G Protein Activation Module," *J. Biol. Chem.*, 276(22):18748-18756 (2001).
Kalaria, R. N., "Serum Amyloid P and related molecules associated with the acute-phase response in Alzheimer's disease," *Res. Immunology*, 143:637-641 (1992).
Kalback et al., "APP Transgenic Mice Tg2576 Accumulate Aβ Peptides That Are Distinct from the Chemically Modified and Insoluble Peptides Deposited in Alzheimer's Disease Senile Plaques," *Biochemistry*, 41:922-928 (2002).
Kallberg et al., "Prediction of Amyloid Fibril-Forming Proteins," *The Journal of Biological Chemistry*, 276(16):12945-12950 (Apr. 20, 2001).
Kardana et al., "Serum HCG β-Core Fragment is Masked by Associated Macromolecules," *Journal of Clinical Endocrinology and Metabolism*, 71(5):1393-1395.
Kascsak et al., "Mouse Polyclonal and Monoclonal Antibody to Scrapie-Associated Fibril Proteins," *J. Virology*, 61(12):3688-3693 (1987).
Katzav-Gozansky et al., "Effect of monoclonal antibodies in preventing carboxypeptidase A aggregation," *Biotechnol. Appl. Biochem.*, 23:227-230 (1996).
Kawabata et al., "Amyloid plaques, neurofibrillary tangles and neuronal loss in brains of transgenic mice overexpressing a C-terminal fragment of human myloid precursor protein," *Nature*, 354:476-478 (1991).
Kayed et al., "Conformational Transitions of Islet Amyloid Polypeptide (IAPP) in Amyloid Formation *In Vitro*," *J. Mol. Biol.*, 287:781-796 (1999).
Kelly, J. W., "Alternative conformations of amyloidogenic proteins govern their behavior," *Current Opinion in Structural Biology*, 6:11-17 (1996).
Kettleborough et al., "Humanization of a mouse monoclonal antibody by CDR-grafting: the importance of framework residues on loop conformation," *Protein Engineering*, 4(7):773-783 (1991).
Khan et al., "Immunopotentiation and Delivery Systems for Antigens for Single-Step Immunization: Recent Trends and Progress," *Pharmaceutical Research*, 11(1):2-11 (1994).
Khatoon et al., "Levels of normal and abnormally phosphorylated tau in different cellular and regional compartments of Alzheimer's disease and control brains," *FEBS Letters*, 351:80-84 (1994).
Kida, et al., "Early Amyloid-β deposits show different immunoreactivity to the amino- and carboxy-terminal regions of b-peptide in Alzheimer's disease and Down's syndrome brain," *Neuroscience Letters*, 193:105-108 (1995).
Kimchi et al., "Analysis of cerebral myloid angiopathy in a transgenic mouse model of Alzheimer disease using in vivo multiphoton microscopy," *J. Neuropath Exp. Neurol.*, 60(3):274-279 (2001).
Klein et al., "Targeting small Aβ oligomers: the solution to an Alzheimer's disease conundrum?," *Trends in Neurosciences*, 24(4):219-224 (2001).

Klyubin et al., "Anti-Aβ Antibodies Prevent Block of Long-Term Potentiation in the CA1 Area of Rat Hippocampus *In Vivo* by naturally Produced Aβ Oligomers," *Neurobiology of Aging*, 25:S224-S225, abstract P2-004, pp. S224-S225 (2004).
Kofler et al., "Mechanism of Allergic Cross-Reactions-III. cDNA Cloning and Variable-Region Sequence Analysis of Two IgE Antibodies Specific for Trinitrophenyl " *Mol. Immunology*, 29(2):161-166 (1992).
Kofler et al., "Immunoglobulin $_k$ Light Chain Variable Region Gene Complex Organization and Immunoglobulin Genes Encoding Anti-DNA Autoantibodies in Lupus Mice," *J. Clin. Invest.*, 82:852-860 (1988).
Koller et al., "Active Immunization of Mice with a Aβ-Hsp70 Vaccine," *Neurodegenerative Disases*, 1:20-28 (2004).
Konig et al., "Development and Characterization of a Monoclonal Antibody 369.2B Specific for the Carboxyl-Terminus of the βA4 Peptide," *Annals of NY Acad. Sci.*, 777:344-355 (1996).
Kotilinek et al., "Reversible memory loss in a mouse transgenic model of Alzheimer's disease," *J. Neurosci.*, 22(15):6331-6335 (2002).
Koudinov et al., "The soluble form of Alzheimer's myloid beta protein is complexed to high density lipoprotein 3 and very high density lipoprotein in normal human plasma," *Biochem. & Biophys. Res. Comm*, 205:1164-1171 (1994).
Kovács et al., "Mutations of the Prion Protein Gene Phenotypic Spectrum," *J. Neurol.*, 249:1567-1582 (2002).
Krishnan et al., "Correlation Between the Amino Acid Position of Arginine in VH-CDR3 and Specificity for Native DNA Among Autoimmune Antibodies[1,2]," *J. Immunol.*, 157(6):2430-2439 (1996).
Kuby, J., eds., p. 123 from *Immunology, Third Edition*, W.H. Freeman & co., (1997).
Kuby, J., eds., pp. 108-109, 131-132 from *Immunology, Third Edition*, W.H. Freeman & co., (1997).
Kuo et al., "High levels of circulating Abeta42 are sequestered by plasma proteins in Alzheimer's disease," *Biochem. Biophys. Res. Comm.*, 257(3):787-791 (1999).
Kuo et al., "Water-soluble Aβ (N-40, N-42) Oligomers in Normal and Alzheimer Disease Brains," *J. Biol. Chem.*, 271(8):4077-4081 (1996).
Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).
Kurashima et al., "Production of Monoclonal Antibody against Amyloid Fibril Protein and Its Immunohistochemical Application," *Appl. Pathol.*, 3(1-2):39-54 (1985).
LaDu et al., "Isoform-specific Binding of Apolipoprotein E to β-Amyloid," *J. Biol. Chem.*, 269(38):23403-23406 (1994).
Lambert et al., "Diffusible, nonfibrillar ligands derived from Aβ1-42 are potent central nervous system neurotoxins," *PNAS*, 95:6448-6453 (1998).
Lambert et al., "Vaccination with soluble Aβ oligomers generates toxicity-neutralizing antibodies," *J. Neurochem.*, 79:595-605 (2001).
Lampert-Etchells et al., "Regional Localization of Cells Containing Complement C1q and C4 mRNAs in the Frontal Cortex During Alzheimer's Disease," *Neurodegeneration*, 2:111-121 (1993).
Landolfi et al., "The Integrity of the Ball-and Socket Joint Between V and C Domains Is Essential for Complete Activity of a Humanized Antibody," *J. Immunology*, 166(3):1748-1754 (2001).
Langer, "New Methods of Drug Delivery," *Science*, 249:1527-1532 (1990).
Lannfelt et al., "Alzheimer's disease: molecular genetics and transgenic animal models," *Behavioural Brain Res.*, 57:207-213 (1993).
Lansbury, Peter T., "Inhibition of myloid formation: a strategy to delay the onset of Alzheimer's disease," *Curr. Ops. In Chemical Biology*, 1:260-267 (1997).
Lavie et al., "EFRH-Phage Immunization of Alzheimer's Disease Animal Model Improves Behavioral Performance in Morris Water Maze Trials," *J. Molecular Neuroscience*, 24:105-113 (2004).
Lee et al., "Aβ immunization: Moving Aβ peptide from brain to blood," *PNAS*, 98(16):8931-8932 (2001).

Lemere et al., "Mucosal Administration of Aβ Peptide Decreases Cerebral Amyloid Burden in Pd-App Transgenic Mice," *Society for Neuroscience Abstracts*, 25(part )I, Abstract 519.6, 29$^{th}$ Annual Meeting, (Oct. 23-28, 1999).

Lemere, et al., "Nasal Aβ treatment induces anti-Aβ antibody production and decreases cerebral myloid burden in PD-APP mice," *Annals of the NY Acad. Sci.*, 920:328-331 (2000).

Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).

Leverone et al., "Aβ1-15 is less immunogenic than Aβ1-40/42 for intranasal immunization of wild-type mice but may be effective for 'boosting'," *Vaccine*, 21:2197-2206 (2003).

Levitt, M., "Molecular dynamics of native protein," *J. Mol . Biol.*, 168:595-620 (1983).

Levey, A. I., "Immunization for Alzheimer's disease: A shot in the arm or a whiff?," *Ann. Neurology*, 48(4):553-555 (2000).

Li et al., "Thermal Stabilization of Carboxypeptidase A as a Function of PH and Ionic Milieu," *Biochem. Mol. Biol. Int.*, 43(3):601-611 (1997).

Licastro et al., "Is immunotherapy an effective treatment for Alzheimer's disease?," *Immunity & Aging*, 1:1-2 (2004).

Linke, "Monoclonal antibodies against myloid fibril protein AA. Production, specificity, and use for immunohistochemical localization and classification of AA-type amyloidosis," *J. Histochemistry and Cytochemistry*, 32(3):322-328 (1982).

Liu et al., "Amyloid β peptide alters intracellular vesicle trafficking and cholesterol homeostasis," *Proc. Natl. Acad. Sci.*, 95:13266-13271 (1998).

Livingston et al., "The Hepatitis B Virus-Specific CTL Responses Induced in Humans by Lipopeptide Vaccination Are Comparable to Those Elicited by Acute Viral Infection," *J. Immunol.*, 159:1383-1392 (1997).

Lo et al., "High level expression and secretion of Fc-X fusion proteins in mammalian cells," *Protein Engineering*, 11(6):495-500 (1998).

Lopez et al., "Serum auto-antibodies in Alzheimer's disease," *Acta. Neurol. Scand.*, 84:441-444 (1991).

Lue et al., "Soluble β-amyloid Peptide Concentration as a Predictor of Synaptic Change in Alzheimer's Disease," *Am. J. Pathol.*, 155:853-562 (1999).

MacCallum et al., Antibody-antigen Interactions: *Contact Analysis and Binding Site Topography*, 262:732-745 (1996).

Maggio et al., "Brain Amyloid—A Physicochemical Perspective," *Brain Pathology*, 6:147-162 (1996).

Majocha et al., "Development of a Monoclonal Antibody Specific for β/A4 Amyloid in Alzheimer's Disease Brain for Application to In Vitro Imaging of Amyloid Angiopathy " *The J. of Nuclear Med.*, 33:2184-2189 (1992).

Mak, et al., "Polyclonals to b-amyloid (1-42) identify most plaque and vascular deposits in Alzheimer cortex, but not striatum," *Brain Research*, 667:138-142 (1994).

Mamikonyan et al., "Anti-Aβ$_{1-11}$ Antibody Binds to Different β-Amyloid Species, Inhibits Fibril Formation, and Disaggregates Preformed Fibrils but Not the Most Toxic Oligomers," *J Biol Chem*, 282(31) 22376-22386 (2007).

Mandel et al., "Clinical trials in neurological disorders using AAV vectors: promises and challenges," *Curr. Opin. Mol. Ther.*, 6(5):482-490 (2004).

Mann, et al., "Amyloid β protein (Aβ) deposition in chromosome 14-linked Alzheimer's disease: Predominance of Aβ$_{42(43)}$," *Annals of Neurology*, 40:149-156 (1996).

Mann et al., "Atypical Amyloid (Abeta) Deposition in the cerebellum in Alzheimer's Disease: An Immunohistochemical Study Using End-Specific Abeta Monoclonal Antibodies " *ACTA Neuropathologica*, 91:647-653 (1996).

Mann et al., "Predominant deposition of myloid-beta 42(43) in plaques in cases of Alzheimer's disease and hereditary cerebral hemorrhage associated with mutatuibs in the myloid precursor protirn gene," The *American Journal of Pathology APR*, 4(148): 1257-1266 (1996).

Mann, et al., "The extent of myloid deposition in brain in patients with Down's syndrome does not depend upon the apolipoprotein E genotype," *Neuroscience Letters*, 196:105-108 (1995).

Manning et al., "Genetic Immunization with Adeno-Associated Virus Vectors Expressing Herpes Simplex Virus Type 2 Glycoproteins B and D," *Journal of Virology*, 71(10):7960-7962 (1997).

Manoj et al., "Approaches to Enhance the Efficacy of DNA Vaccines," *Critical Rev. Clin. Lab. Sci.*, 41(1):1-39 (2004).

Marhaug et al., "Monoclonal hybridoma antibodies to human myloid related protein SAA," *Clin. Exp. Immunol.*, 50(2):390-396 (1982).

Marotta et al., "Overexpression of myloid precursor protein A4 (β-amyloid) immunoreactivity in genetically transformed cells: Implications for a cellular model of Alzheimer amyloidosis," *PNAS*, 86:337-341 (1989).

Marshall, E., "Gene Therapy's Growing Pains," *Science*, 269:1050-1055 (1995).

Masliah et al., "Amyloid Protien Precursor Stimulates Excitatory Amino Acid Transport," *The Journal of Biological Chemisrty*, 273(20):12548-12554 (1998).

Masliah et al., "β-Amyloid peptides enhance a-synuclein accumulation and neuronal deficits in a transgenic mouse model linking Alzheimer's disease and Parkinson's disease," *PNAS*, 98(21):12245-12250 (2001).

Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1996).

Masters et al., "Amyloid Plaque core protein in Alzheimer Disease and Down Syndrome," *PNAS*, 82:4245-4249 (1985).

Mattson, "Cellular actions of beta-amyloid precursor protein and its soluble and fibrillogenic derivatives," *Physiol Rev.*, 77(4):1081-132 (1997).

Mattson et al., "Good and bad myloid antibodies," *Science*, 301(5641):1845-1849 (2003).

Maury et al., "Immunohistochemical Localization of Amyloid in Finnish Hereditary Amyloidosis with Antibodies to Gelsolin Peptides," *Laboratory Investigation*, 64(3):400-404 (1991).

Mavragani et al., "A Case of Reversible Posterior Leucoencephalopathy Syndrome After Rityximab Infusion," *Rheumatology*, 43(11) 1450-1451 (2006).

McGee et al., "The encapsulation of a model protein in poly (D, L lactide-co-glycolide) microparticles of various sizes: an evaluation of process reproducibility," *J. Micro. Encap.*, 14(2):197-210 (1997).

McGeer, et al., "Immunohistochemical localization of beta-amyloid precursor protein sequences in Alzheimer and normal brain tissue by light and electron microscopy " *J. of Neuroscience Res.*, 31:428-442 (1992).

McLaurin et al., "Therapeutically effective antibodies against Amyloid- β peptide target Amyloid- β residues and 4-10 and inhibit cytotoxicity and fibrillogenesis," *Nat Med.*, 8(11):1263-1269 (2002).

McLean et al., "Soluble pool of Aβ myloid as a determinant of severity of neurodegeneration in Alzheimer's disease," *Amer. Neurological Assoc*, 46:860-866 (1999).

McNeal et al., "Stimulation of local immunity and protection in mice by intramuscular immunization with triple- or double-layered rotavirus particles and QS-21," *Virology*, 243:158-166 (1998).

Meda et al., "Activation of microglial cells by β-amyloid protein and interferon-y," *Nature*, 374:647-650 (1995).

Mena, et al., "Monitoring pathological assembly of tau and β-amyloid proteins in Alzheimer's disease," *Acta Neuropathol.*, 89:50-56 (1995).

Merluzzi, et al., "Humanized antibodies as potential drugs for therapeutic use " *Adv Clin Path.*, 4(2):77-85 (2000).

Merriam-Webster online medical dictionary, entry for "cure", accessed Sep. 5, 2006.

Miller et al., "Antigen-driven Bystander Suppression after Oral Administration of Antigens," *J. Exp. Med.*, 174:791-798 (1991).

Misra et al., "Drug Delivery to the Central Nervous System: A review," *J. Pharm Pharm Sci.*, 6(2):252-273 (May 2003), Abstract.

Mitchell et al, " Prevention of Intracerebral Hemorrhage," *Current Drug Targets*, 8(7):832-838 (2007).

Monsonego et al., "Immune hyporesponsiveness to myloid β-peptide in myloid precursor protein transgenic mice: Implications for the pathogenesis and treatment of Alzheimer's disease," *Pnas*, 98(18):10273-10278 (2001).

Monsonego et al., "Increased T cell reactivity to myloid β protein in older humans and patients with Alzheimer's disease," *J. Clin. Invest.*, 112(3):415-422 (2003).

Monsonego et al., "Immunotherapeutic approaches to Alzheimer's disease," *Science*, 302(5646):834-838 (2003).

Morgan, et al., "A beta peptide vaccination prevents memory loss in an animal model of Alzheimer's disease," *Nature*, 408(6815):982-985 (2000).

Morgan et al., "The N-terminal end of the $C_H2$ domain of chimeric human IgG1 anti-HLA-DR is necessary for C1q, FcyRII and FcyRII binding," *Immunology*, 86:319-324 (1995).

Mori et al., "Mass Spectrometry of Purified Amyloid β Protein in Alzheimer's Disease," *J. Biol. Chem.*, 267(24):17082-17088 (1992).

Morris, et al., "The Consortium to Establish a registry for Alzheimer's Disease (CERAD)," *Neurology*, 39:1159-1165 (1989).

Munch et al., "Potentional neurotoxic inflammatory response to Aβ vaccination in humans," *J. Neural Transm.*, 109:1081-1087 (2002).

Munson eds., *Principals of Pharmacology: Basic Concepts & Clinical Applications*, pp. 47-48, Chapman & Hall, New York, New York (1995).

Murphy et al., "Development of a Monoclonal Antibody Specific for the COOH-Terminal of β-Amyloid 1-42 and Its Immunohistochemical Reactivity in Alzheimer's Disease and Related Disorders," *Am. J. Pathology*, 144(5):1082-1088 (1994).

Mutschler et al., "*Arzneimittel-Wirkungen, Lehrbuch der Pharmakologie and Taxiklogie,*" Wissenschftliche Verlagsgesellschaft mbH Stuttgart, 6*th* edition, pp. 651-656 (1991), (German Article).

Mutschler et al., *Drug Actions: Basic Principles and Therapeutic Aspects* pp. 7, 11-12, Medpharm Scientific Publishers, Stuttgart, Germany (1995).

Myers et. al., "Targeting Immune Effector Molecules to Human Tumor Cells Through Genetic Delivery of 5T4-Specific SCFVFusion Protiens," Cancer Gene Therapy, 9(11):884-896 (2002).

Nakamura et al., "Histopathological studies on senile plaques and cerebral myloid angiopathy in aged cynomologus monkeys," *Exp. Anim.*, 43:711-718 (1995).

Nakamura, et al., "Carboxyl end-specific monoclonal antibodies to myloid β protein (Aβ) subtypes (Aβ40 and Aβ42(43) differentiate Ab in senile plaques and myloid angiopathy in brains of aged cynomolgus monkeys," *Neuroscience Letters*, 201:151-154 (1995).

Nakayama et al., "Histopathological studies of senile plaques and cerebral amyloidosis in cynomolgus monkeys," *J. of Med. Primatoloqy* 27:244-252 (1998).

Nalbantoglu, J., "Beta-amyloid protein in Alzheimer's disease," *Can. J. Neurol. Sci.*, 18(3 suppl.):424-427 (1991), abstract only.

Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.

Naslund et al., "Correlation between elevated levels of myloid β peptide in the brain and cognitive decline," *J. Am. Med. Assoc.*, 283:1571 (2000).

Nathanson et al., "Bovine Spongiform Encephalopathy (BSE): Causes and Consequences of a Common Source Epidemic," *Am. J. Epidemiol.*, 145(11):959-969 (1997).

New York Times National, "Anti-Inflammatory Drugs May Impede Alzheimer's," (Feb. 20, 1994).

Newcombe et al., "Solubility characteristics of isolated myloid fibrils," *Biochim. Biophys. Acta*, 104:480-486 (1965).

Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).

Nicoll et al., "Neuropathology of human Alzheimer's disease after immunization with myloid-β peptide: a case report," *Nature Medicine*, 9(4):448-452 (2003).

Niemann, "Transgenic farm animals get off the ground;" *Transgenic Research*, 7:73-75 (1998).

Novartis, "Novartis MF59™—Adjuvanted Influenza Vaccine (Fluad®) Significantly Reduces Hospitalization in Elderly," Novartis Press Release, Oct. 19 2007.

Novotny et al., "Structural invariants of antigen binding: Comparison of immunoglobulin $V_L.V_H$ and $V_L.V_L$ domain dimmers," *PNAS*, 82:4592-4596 (1985).

Okie, S., "Promising Vaccine Targets Ravager of Minds," *Washington Post*, p. A01, May 8, 2001.

Okura et al., "Nonviral Aβ DNA vaccine therapy against Alzheimer's disease: Long-term effect and safety," *PNAS*, 103(25):9619-9624 (2006).

Orkin et al., *Report and Recommendations of the Panel to Assess the NIh Investment in Research on Gene Therapy*, Dec. 7, 1995.

Orlandi et al., "Cloning immunoglobulin variable domains for expression by the polymerase chain reaction," *PNAS*, 86:3833-3837 (1989).

Padlan et al., Structure of an Antibody-Antigen Complex: Crystal Structure of the HyHEL-10 Fab-lysozyme Complex, Immunology, 86:5938-5942 (1989).

Paganetti et al., "Amyloid precursor protein truncated at any of the γ-secretase sites is not cleaved to β-amyloid," *J. Neurosci. Res.*, 46(3):283-293 (1996).

Palha et al., "Antibody recognition of amyloidogenic transthyretin variants in serum of patients with familial amyloidiotic polyneuropathy, " *J. Mol. Med.*, 78:703-707 (2001).

Pallitto et al., "Recognition sequence design for peptidyl modulators of β-amyloid aggregation and toxicity," *Biochemistry*, 38(12):3570-3578 (1999).

Pan et al., "Antibodies to β-Amyloid Decrease the Blood-to-Brain Transfer of β-Amyloid Peptide," *Exp. Biol. Med.*, 227(8):609-615 (2002).

Pangalos et al., "Disease Modifiying Strategies for the Treatment of Alzheimer's Disease Targeted at Modulating Levels of β-amyloid Peptide," Biochemical Socity Transactions, 33(4):553-558 (2005).

Panka et al., "Variable region framework differences result in decreased or increased affinity of variant anti-digoxin antibodies," *PNAS*, 85:3080-3084 (1998).

Pardridge et al., "Chimeric peptides as a vehicle for peptide pharmaceutical delivery through the blood-brain barrier," *Biochem. Biophys. Res. Comm.*, 146:307-313 (1987).

Pardridge et al., "The Blood-Brain Barrier: Bottleneck in Brain Drug Development," *J. Am. Soc. Exp. Neurotherapeutics*, 2:3-14 (2005).

Paresce et al., "Microglial cells influence aggregates of the Alzheimer's disease myloid beta-protein via a scavenger receptor," *Neuron*, 17:553-565 (Sep. 1996).

Parnetti et al., "Cognitive Enhancement Therapy for Alzheimer's Disease, The Way Forward," *Drugs*, 53(5):752-768 (1997).

Pascalis et al., "Grafting of "Abbreviated" Complementarity-Determining Containing Specifictiy-Determining Residues Essential for Ligand Contact to Engineer a Less Immunogenic Humanized Monoclonal Antibody," *The Journanal Immunology*, 169:3076-3084 (2002).

Paul et al., "Transdermal immunization with large proteins by means of ultradeformable drug carriers," *Eur. J. Immunol.*, 25: 3521-3524 (1995).

Paul, W. E., eds., *Fundamental Immunology*, Third Edition, pp. 292-295, Raven Press, New York (1993).

PCT International Preliminary Examination Report of Feb. 9, 2004 for application PCT/US01/46587.

PCT Written Opinion of Dec. 14, 2004 for application PCT/US04/02856.

PCT International Preliminary Report on Patentability (Chapter I) of Sep. 16, 2005 with Written Opinion of May 9, 2005 for application PCT/US04/007503.

PCT International Preliminary Report on Patentability (Chapter II) of Dec. 21, 2006 for application PCT/US2006/002837.

PCT International Preliminary Report on Patentability (Chapter I) of Jul. 31, 2007 with Written Opinion for application PCT/US2006/004741.

PCT International Preliminary Report on Patentability (Chapter I) of Oct. 20, 2009 with Written Opinion of Oct. 3, 2008 for application PCT/US2008/060926.

PCT Written Opinion of Dec. 22, 2008 for application PCT/US2008/80370.

PCT Written Opinion of Aug. 11, 2006 for application PCT/US2006/002837.

PCT Search Report of Jan. 22, 2009 for application PCT/US2008/80370.
PCT Search Report of Oct. 9, 2008 for application PCT/US2008/060926.
PCT Search Report of Aug. 11, 2006 for application PCT/US2006/002837.
PCT Search Report of Aug. 8, 2006 for application PCT/US2005/045515.
PCT International Preliminary Report on Patentability (Chapter II) of Apr. 27, 2006 for application PCT/US04/007503.
PCT Search Report of Apr. 6, 2006 and Written Opinion of Apr. 8, 2006 for application PCT/US04/44093.
PCT Search Report of Oct. 1, 2007 and Written Opinion of Oct. 1, 2007 for application PCT/US07/09499.
PCT International Preliminary Report on Patentability (Chapter I) of Feb. 2, 2010 for application PCT/US07/09499.
Peeters et al., "Comparison of four bifunctional reagents for coupling peptides to proteins and the effect of the three moieties on the immunogenicity of the conjugates," *J. Immunological Methods*, 120:133-143 (1989).
Perez et al., "The β-Amyloid Precursor Protein of Alzheimer's Disease Enhances Neuron Viability and Modulates Neuronal Polarity," *J. Neurosci.*, 17(24):9407-9414 (1997).
Persson et al., "IgG subclass-associated affinity differences of specific antibodies in humans," *J. Immunology*, 140(11):3875-3879 (1988), abstract only.
Perutz et al., "Amyloid fibers are water-filed nanotubes," *PNAS*, 99(8):5591-5595 (2002).
Peterson, et al., "Recombinant Antibodies: Alternative Strategies for Developing and Manipulating Murine-Derived Monoclonal Antibodies," *Laboratory Animal Science*, 46(1):8-14 (1996).
Pfeifer et al., "Cerebral hemorrhage after passive anti-Aβ immunotherapy," *Science*, 298(5597):1379 (2002).
Phelps et al., "Development and Characterization of Monoclonal Antibodies Specific for Amylin," *Hybridoma*, 15(5):379-386 (1996).
Philippe, et al. "Generation of a monoclonal antibody to the carboxy-terminal domain of tau by immunization with the amino-terminal domain of the myloid precursor protein " *J. of Neuroscience Res.*, 46:709-719 (1996).
Piera et al., "Cytokines as adjuvants: effects on the immunogenicity of NeuAc alpha 2-GaINAc alpha-O-Ser/Thr (sialyl-Tn)," *Int. J. Cancer*, 55(1):148-152 (1993).
Pluckthun, A., "Mono- and Bivalent Antibody Fragments Produced in *Escherichia coli*: Engineering, Folding and Antigen Binding," *Immunological Reviews*, 130:151-188 (1992).
PNAS Information for Authors (revised Jan. 1997), Retrieved Apr. 21, 2008 from http://web.archive.org/web/19970610092808/www.pnas.org/iforc.shtml.
Poduslo et al., "Permeability of proteins at the blood-brain barrier in the normal adult mouse and double transgenic mouse model of Alzheimer's disease," *Neurobiol. Dis.*, 8(4):555-567 (2001).
Prada et al., "Antibody-Mediated Clearance of Amyloid-β Peptide From Cerebral Amyloid Angiopathy Revealed by quantitative in Vivo Imaging," Journal of Neuroscience, 27(8):1973-1980 (2007).
Press Release, "Alzheimer's vaccine developer awarded Potamkin Prize," American Academy of Neurology, May 7, 2001.
Prieels et al., "Synergistic adjuvants for vaccines," *Chemical Abstracts*, 120(8):652, col. 1, abstract 86406t (1994).
Probert et al., "Spontaneous inflammatory demyelinating disease in transgenic mice showing central nervous system-specific expression of tunmor necrosis factor α," *PNAS*, 92:11294-11298 (1995).
Prusiner et al., "Ablation of the prion protein (PrP) gene in mice prevents scrapie and facilitates production of anti-PrP antibodies," *PNAS*, 90:10608-10612 (1993).
Putative CDR determination for SEQ Id Nos: 2 and 4 (pp. 1-2), Jun. 10, 2004.
Qu et al., "A$β_{42}$ gene Vaccine Prevents A$β_{42}$ deposition in brain of Double Trangenic Mice," *J. Neurological Sciences*, 260:204-213 (2007).
Qu et al., "A$β_{42}$ gene vaccination reduces brain myloid plaque burden in transgenic mice," *J. Neurological Sciences*, 244:151-158 (2006).
Queen et al., "A humanized antibody that binds to the interleukin 2 receptor," *PNAS*, 86:10029-10033 (1989).

Quon et al., "Formation of β-Amyloid protein deposits in brains of transgenic mice," *Nature*, 352:239-241 (1991).
Racke et al., "Exacerbation of Cerebral Amyloid Angiopathy-Assoiciated Microhemorrhage in Amyloid Precursor Protein Trasngenic Mice by Immunotherapy Is Dependent on Antibody Recognition of Deposited Forms of myloid β," *J. Neurosci.*, 25(3):629-636 (2005).
Ragusi et al., "Redistribution of Imipramine from Regions of the Brain Under the Influence of Circulating Specific Antibodies," *J. Neurochem.*, 70(5):2099-2105 (1998).
Rammensee, H.G., "Chemistry of peptides associated with MHC class I and class II molecules," *Current Opinion in Immunology*, 7:85-96 (1995).
Raso, "Immunotherapy of Alzheimer's Disease," *Immunotherapy Weekly*, Abstract (Apr. 2, 1998).
Raso, V.A., Grant application # 1 R43 AGI 5746-01 (non-redacted version), "Immunotherapy of Alzheimer's Disease".
Raso, V.A., Grant application # 1 R43 AGI 5746-01 (redacted version), "Immunotherapy of Alzheimer's Disease".
Research Corporation Technology News, "THP and SangStat Partner to Develop Humanized Polyclonal Antibody Drugs," Nov. 11, 2002.
"Researchers Develop Blood Test to Diagnose Alzheimer's- Type Changes in Mice," downloaded from www.businesswire.com on Dec. 15, 2004.
Riechmann et al., "Reshaping Human Antibodies for Therapy," Nature, 332:323-327 (1988).
Robbins et al., "The Intronic Region of an Imcompletely Spliced gp100 Gene Transcript Encodes an Epitope Recognized by Melanoma-Reactive Tumor-Infiltrarting Lymphocytes," Journal of Immunology, 159(1):303-308 (1997).
Rodriguez et al., "Enfermedad de Azlheimer. Situacion Actual y Estrategias Terapeuticas" (Alzheimer Disease: present situation and therapeutic strategies) *Rev Cubana Med* [online], 38(2):134-142 (1999).
Rogers et al., "Complement activation by β-amyloid in Alzheimer Disease," *PNAS*, 89:1-5 (1992).
Rolph et al., "Recombinant viruses as vaccines and immunological tools," *Immunity to Infection*, 9:517-521 (1997).
Rosenberg, R. N., "The Potamkin Prize for Pick's, Alzheimer's Disease and Related Disorders," pp. 1-5.
Roses, A.D., "Apoplipoprotein E alleles as risk factors in Alzheimer's disease," *Annu. Rev. Med.*, 47:387-400 (1996).
Rossor et al., "Alzheimer's Disease Families with Amyloid Precursor Protein Mutations," *Annals of New York Academy of Sciences*, 695:198-202 (1993).
Rudikoff et al., "Single amino acid substitution altering antigen-binding specificity," *PNAS*, 79:1979-1983 (1982).
Rudinger, "Characteristics of the Amino Acids as Components of a Peptide Hormone Sequence," in *Peptide Hormones*, J.A. Parson, ed. University Park Press, Baltimore, pp. 1-7 (1976).
Saido et al., "Amino-and-Carboxyl-Terminal Heterogeneity of β-Amyloid Peptides Deposited in Human Brain," Neuroscience Letters, 215:173-176 (Aug. 8, 1996).
Saido et al., "Autolytic Transition of μ-Calpain Upon Activation as Resolved by Antibodies Distinguishing Between the Pre- and Post-Autolysis Forms," J. Biochem., 111:81-86 (1992).
Saido et al., "Spatial Resolution of Fodrin Proteolysis in Postischemic Brain," *J. Biol. Chem.*, 268(33):25239-25243 (1993).
Saido et al., "Spatial Resolution of the Primary β-Amyloidogenic Process Induced in Postischemic Hippocampus," *J. Biol. Chem.*, 269(21):15253-15257 (1994).
Saito et al., "Vector-mediated delivery of $^{125}$I-labeled β-amyloid peptide Ab$^{1-40}$ through the blood-brain barrier and binding to Alzheimer disease myloid of the Aβ$^{1-40}$ vector complex," *PNAS*, 92:10227-10231 (1995).
Saitoh, N. et al., "Immunological analysis of Alzheimer's disease using anti- β-protein monoclonal antibodies," *Sapporo Med. J.*, 60:309-320 (1991).
Saldanha et al., "A single backmutation in the human kIV framework of a previously unsuccessfully humanized antibody restores the binding activity and increases the secretion in cos cells," *Molecular Immunology*, 36:709-719 (1999).

Sasaki et al., "Human choroid plexus is an uniquely involved area of the brain in amyloidosis: a histochemical, immunohistochemical and ultrastructural study," *Brain Res.*, 755:193-201 (1997).

Schenk et al., "Immunization with myloid-β attenuates Alzheimer-disease-like pathology in the PDAPP mouse," *Nature*, 400:173-177 (1999).

Schenk et al., "Therapeutic Approaches Related to Amyloid-β Peptide and Alzheimer's Disease," *J. Med. Chem.*, 38(21):4141-4154 (1995).

Schenk et al., "β-peptide immunization," *Arch. Neurol.*, 57:934-936 (2000).

Schenk et al., "Immunotherapy with beta-amyloid for Alzheimer's disease: a new frontier," *DNA Cell Biol.*, 20(11):679-81 (2001).

Schenk, D., "Amyloid-β immunotherapy for Alzheimer's disease: the end of the beginning," *Nature Reviews*, 3:824-828 (2002).

Schenk et al., "Current progress in beta-amyloid immunotherapy " *Curr. Opin. Immunology*, 16(5):599-606 (2004).

Schmid, R. E., "Study suggest Alzheimer vaccine fix," from www.msnbc.com/news, pp. 1-5 (2002).

Schmidt et al., "Monoclonal Antibodies to a 100-kd protein reveal abundant A beta-negative plaques throughout gray matter of Alzheimer's disease brains," *The American Journal of Pathology*, 1(151):69-80 (1997).

Schmitt et al., "Interactions of the myloid r β myloid fragment$_{(25-35)}$ with peripheral blood dendritic cells," *Mechanisms of Ageing and Development*, 94:223-232 (1997).

Schroeder et al., "Preferential Utilization of Conserved Immunoglobulin Heavy Chain Variable Gene Segments During Human Fetal Life," *Immunology*, 87:6146-6150 (1990).

Schwarzman et al., "Transthyretin sequesters myloid β protein and prevents myloid formation," *PNAS*, 91:8368-8372 (1994).

Seabrook et al., "Species-specific Immune response to Immunization with Human Versus rodent Abeta Peptide," Neuobiology of Aging, 25(9) 1141-1151 (2004).

Seidl et al., "Predominant $V_H$ genes expressed in innate antibodies are associated with distinctive antigen-binding sites," *PNAS*, 96:2262-2267 (1999).

Sela et al, "Different roles of D-amino acids in immune phenomena," *FASEB J*, 11(6):449-456 (1999).

Selkoe, "Alzheimer's Disease: A Central Role for Amyloid," *J. Neuropathol. Exp. Neurol.*, 53(5): 438-447 (1994).

Selkoe, "Physiological production of the β-amyloid protein and the mechanism of Alzheimer's disease," *Trends in Neurosciences*, 16(10): 403-409 (1993).

Selkoe, "The cell biology of beta-amyloid precursor protein and presenilin in Alzheimer's disease " *Trends Cell Biol.*, 8(11):447-53 (1998).

Selkoe, D.J., "Imaging Alzheimer's Amyloid," *Nat. Biotech.*, 18:823-824 (2000).

Selkoe, Dennis J., "Alzheimer's Disease: Genotypes, Phenotype, and Treatments," *Science*, 275:630-631 (1997).

Selkoe, Dennis J., "Amyloid Protein and Alzheimer's Disease . . . ," *Scientific American*, pp. 68-78 (1991).

Selkoe, Dennis J., "In the Beginning . . . ," *Nature*, 354:432-433 (1991).

Selkoe, Dennis J., "The Molecular pathology of Alzheimer's Disease," *Neuron*, 6:487-498 (1991).

Selkoe, D. J., "Alzheimer's disease is a synaptic failure," *Science*, 298(5594):789-791 (2002).

Sergeant et al., "Truncated beta-amyloid peptide species in pre-clinical Alzheimer's disease as new targets for the vaccination approach," *J. Neurochem.*, 85(6):1581-1591 (2003).

Seubert et al., "Isolation and quantification of soluble Alzheimer's β-peptide from biological fluids," *Nature*, 359: 325-327 (1992).

Seubert et al., "Antibody Capture of Soluble Aβ does not Reduce Cortical Aβ Amyloidosis in the PDAPP Mouse," *Neurodegenerative Diseases*, 5:65-71 (2008).

Shepherd et al., "The design of the humanized antibody," Monocolonal Antibodies: A Pratical Approcach 58-66 (2000).

Sheehan et al., "The Utilization of Individual $V_H$ Exons in the Primary Repertoire of Adult BALB/c Mice'," *The Journal of Immunology*, 151(10):5364-5375 (Nov. 15, 1993).

Shinkai et al., "Amyloid β-Proteins 1-40 and 1-42(43) in the Soluble Fraction of Extra- and Intracranial Blood Vessels," *Ann. Neurol.*, 38:421-428 (1995).

Shiosaka, S., "Attempts to make models for Alzheimer's disease," *Neuroscience Res.*, 13:237-255 (1992).

Sidhu, "Page display in pharmaceutical biotechnology," *Current Opinoin in Biotechnology*, 11:610-616 (2000).

Sigmund, "Viewpoint: Are Studies in Genetically Altered Mice Out of Control "*Arterioscler Thromb Vasc Biol.*, 20:1425-1429 (2000).

Signet Laboratories, Inc., Product data sheet for mouse monoclonal clone 6E10, revised Jul. 13, 2005.

Sigurdsson et al., "A safer vaccine for Alzheimer's disease?," *Neurobiology of Aging*, 23:1001-1008 (2002).

Sigurdsson et al., "Anti-prion antibodies for prophylaxis following prion exposure in mice," *Neurosciences Letters*, 336:185-187 (2003).

Sigurdsson et al., "Immunization Delays the Onset of Prion Disease in Mice " *American Journal of Pathology*, 161:13-17 (2002).

Sigurdsson, et al., "In vivo reversal of Amyloid-beta lesions in rat brain " *J Neuropathol Exp Neurol.*, 59(1):11-17 (2000).

Sigurdsson et al., "Immunization with a Nontoxic/Nonfibrillar Amyloid-β Homologous Peptide Reduces Alzheimer's Disease-Associated Pathology in Trasngenic Mice " *Am. J. Pathology*, 159(2):439-447 (2001).

Simmons, L., "Secondary structure of myloid β peptide correlates with neurotoxic activity *in vitro*," *Molecular Pharmacology*, 45:373-379 (1994).

Singh, K. S., "Neuroautoimmunity: Pathogenic Implications for Alzheimer's Disease," *Gerontology*, 43:79-94 (1997).

Singh, V. K., "Studies of neuroimmune markers in Alzheimer's disease," *Mol. Neurobiology*, 9(1-3):73-81 (1994), abstract only.

Sinha, et al., "Recent advances in the understanding of the processing of APP to beta myloid peptide," *Ann N Y Acad Sci.*, 920:206-8 (2000).

SIPE, "Amyloidosis," *Annu. Rev. Biochem.*, 61:947-975 (1992).

Skolnick and Fetrow, "From genes to protein structure and function: novel applications of computational approaches in the genomic era," *Trends in Biotech*, 18(1):34-39 (2000).

Small et al., "Alzheimer's disease and Abeta toxicity: from top to bottom " *Nat Rev Neurosci.*, 2(8):595-598 (2001).

Small et al., "Cerebral metabolic and cognitive decline in persons at genetic risk for Alzheimer's disease," *PNAS*, 97(11):6037-6042 (2000).

Small, "The Role of the Amyloid Protien Precursors (APP) in Alzheimer's Disease: Does the Normal Function of APP Explain the Topography of Neurodegeneration?," *Neurochemical Research*, 23(5):795-806 (1997).

Smith et al., "Phage Display," *Chemical Reviews, American Chemical Society*, 97(2):391-410 (1997).

Smith et al., "The challenges of genome sequence annotation or 'The devil is in the details,'" *Nature Biotechnology*, 15:1222-1223 (1997).

Smits et al., "Prion Protein and Scrapie Susceptibility," *Vet. Quart.*, 19(3):101-105 (1997).

Solomon and et al., "Modulation of the Catalytic Pathway of Carboxypeptidase A by Conjugation with Polyvinyl Alcohols," *Adv. Mol. Cell Biology*, 15A:33-45 (1996).

Solomon et al., "Activity of monoclonal antibodies in prevention of in vitro aggregation of their antigens," *Immunotechnology*, 2(4):305 (1996).

Solomon et al., "Disaggregation of Alzheimer β-amyloid by site-directed mAb," *PNAS*, 94:4109-4112 (1997).

Solomon et al., "Monoclonal antibodies inhibit in vitro fibrillar aggregation of the Alzheimer β-amyloid peptide," *PNAS*, 93:452-455 (1996).

Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).

Solomon, A., "Pro-Rx (Protein Therapeutics)," University of Tennessee Medical Center.

Solomon, B., "New Approach Towards Fast Induction of Anti β-Amyloid Peptide Immune Response," Department of Molecular Microbiology & Biotechnology, Tel-Aviv University, Ramat Aviv, Tel-Aviv, Israel.

Solomon, B., "Immunological approaches as therapy for Alzheimer's disease" *Expert Opin. Biol. Ther.*, 2(8):907-917 (2002).

Solomon, B., "Generation and brain delivery of anti-aggregating antibodies against β-amyloid plaques using phage display technology," *J. Neural Transm. Suppl.*, 62:321-325 (2002).

Solomon, B., "Immunotherapeutic strategies for prevention and treatment of Alzheimer's disease," *DNA and Cell Biology*, 20(11):697-703 (2001).

Solomon et al., "Fast induction of anti-β-amyloid peptide immune response" *Research and Practice in Alzheimer's Disease*, 6:260-264 (2002).

Soto et al., "Beta sheet breaker peptides inhibit fibrillogenesis in a rat brain model of amyloidosis: implications for Alzheimer's therapy," *Nature Medicine.*, 4(7):822-826 (1998).

Soto et al., "The a-helical to β-strand transition in the amino-terminal fragment of the Amyloid β-peptide modulates Amyloid formation," *J. Biol. Chem*, 270(7):3063-3067 (1995).

Soto et al., "The conformation of Alzheimer's beta peptide determines the rate of myloid formation and its resistance to proteolysis," *Biochem. J.*, 314:701-707 (1996).

Souder et al., "Overview of Alzheimer's disease," *Nurs. Clin. N. Am.*, 39:545-559 (2004).

Southwick et al., "Assessment of Amyloid β protein in Cerebrospinal fluid as an Aid in the Diagnosis of Alzheimer's Disease," *J. Neurochemistry*, 66:259-265 (1996).

Spellerberg et al., "DNA Vaccines Against Lymphoma," Journal of Immunology, 159:1885-1892 (1997).

Sood et al., "Synthetic Peptides: A Modern Approach to Vaccination," *Indian Journal of Experimental Biology*, 34:849-861 (1998).

Spooner et al., "The generation and characterization of potentially therapeutic Aβ antibodies in mice: differences according to strain and immunization protocol," *Vaccine*, 21:290-297 (2002).

St. George-Hyslop et al., "Antibody clears senile plaques," *Nature*, 40:116-117 (1999).

Staunton et al., "Primary structures of ICAM-1 demonstrates interaction between members of the immunoglobulin and intergrin supergene families," *Cell* 52(6):925-33 (1988), abstract only.

*Stedman's Medical Dictionary*, 27th Edition, "Vaccine," p. 1922, lines 1-3 (2000).

Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).

Stern et al., "Antibodies to the β-amyloid peptide cross-react with conformational epitopes in human fibrinogen subunits from peripheral blood," *FEBS Letters*, 264(1):43-47 (1990).

Stoute et al., "A Preliminary Evaluation of a Recombinant Circumsporozoite Protein Vaccine Against *Plasmodium Falciparum Malaria*", *N. Engl. J. Med.*, 336(2):86-91 (1997).

Strbak et al., "Passive Immunization and Hypothalamic Peptide Secretion", *Neuroendocrinology*, 58:210-217 (1993).

Studnicka et al., "Human-engineered monocilnal antibodies retain full specific binding activity by preserving non-CDR complemenatary-modullating resudes," *Protien Eng.*, 7(6):805-814 (1994), Abstract only.

Sturchler-Pierrat et al., "Two myloid precursor protein transgenic mouse models with Alzheimer disease-like pathology," *PNAS*, 94:13287-13292 (1997).

Su et al., "Intravascular infusions of soluble β-amyloid compromise the blood-brain barrier, activate CNS Glial cells and induce peripheral hemorrhage," *Brain Research*, 818:105-107 (1999).

Suo et al., "Soluble Alzhelmers β-amyloid constricts the cerebral vasculature in vivo" *Neuroscience Letters*, 257:77-80 (1998).

Supplementary Partial European Search Report of Apr. 10, 2007 for European Application 04720353.4-1222.

Szendrei, et al., "The effects of aspartic acid-bond isomerization on in vitro properties of the myloid β-peptide as modeled with N-terminal decapeptide fragments " *Int. J. Peptide Protein Res.*, 47:289-296 (1996).

Tabaton et al., "Soluble myloid β-protein is a marker of Alzheimer myloid in brain but not in cerebrospinal fluid," *Biochem. And Biophys. Res. Comm.*, 200(3):1598-1603 (1994).

Tahtinen et al., "Minimal Size of HIV-1 NEF Antigenic Epitopes Reconzied by Human Sera," Int. Conf. AIDS Jun. 16-21 1991, Published Jun. 1991, abstract No. W.A. 1334.

Tal et al., "Complete Freund's Adjuvant Immunization Prolongs Survival in Experimental Prion Disease in Mice," *Journal of Neuroscience Research*, 71:286-290 (2003).

Tamaoka et al., "Antibodies to myloid beta protein (A beta) crossreact with glyceraldehyde-3-phosphate dehydrogenase (GAPDH)," *Neurobiology of Aging*, 3(17):405-414 (1996).

Tan et al., "Amyloidosis," *Histopathology*, 25:403-414 (1994).

Tanaka et al., "NC-1900, an active fragment analog of arginine vasopressin, improves learning and memory deficits induced by beta-amyloid protein in rats," *European J. Pharmacology*, 352:135-142 (1998).

Tang et al., "Genetic immunization is a siple method for eliciting an immune response," *Nature*, 356:152-154 (1992).

Teller et al., "Presence of soluble myloid β-peptide precedes myloid plaque formation in Down's syndrome" *Nature Medicine*, 2(1):93-95 (1996).

Tennent et al., "Serum myloid P component prevents proteolysis of the myloid fibrils of Alzheimer's disease and systemic amyloidosis," *PNAS*, 92:4299-4303 (1995).

Thorsett, E.D. et al., "Therapeutic approaches to Alzheimer's disease," *Curr. Op. in Chem. Biology*, 4:377-382 (2000).

Tjernberg et al., "A molecular model for Alzheimer myloid β-peptide fibril formation," *J. Biol. Chem.*, 274(18):12619-12625 (1999).

Tjernberg et al., "Arrest of β-amyloid fibril formation by a pentapeptide ligand," *J. Biol. Chem.*, 271:8545-8548 (1996).

Tjernberg, et al, "Controlling myloid beta-peptide fibril formation with protease-stable ligands," *J. Biol Chem.*, 272(19):12601-12605 (1997).

Town et al., "Characterization of murine immunoglobulin G antibodies against human Amyloid-$\beta_{1-42}$" *Neurosci. Lett*, 307:101-104 (2001).

Trang et al., "Pharmacokinetics of a Mouse/Human Chimeric Monoclonal Antibody (C-17-1A) in Metastatic Adencarcinoma Patients," Pharmaceutical Research 7(6):587-592 (1990).

Travis, J., "A Vaccine for Alzheimer's Disease?®," *Science News Online*, 156(2) pp. 1-3 downloaded from internet (1999).

Travis, J., "Saving the Mind Faces High Hurdles," *Science*, 309:731-734 (2005).

Trieb et al., "Is Alzheimer beta myloid precursor protein (APP) an autoantigen? Peptides corresponding to parts of the APP sequence stimulate T lymphocytes in normals, but not in patients with Alzheimer's disease," *Immunobiology*, 191(2-3):114-115 Abstract C.37, (1994).

Trieb et al., "APP Peptides Stimulate Lymphocyte Proliferation in Normals, But Not in Patients With Alzheimer's Disease," *Neurobiology of Aging*, 17(4):541-547 (1996).

Tsuzuki et al., "Amyloid β protein in rat soleus in choroquine-induced myopthy using end-specific antibodies for Aβ40 and Aβ42: immunohistochemical evidence for myloid β protein," *Neuroscience Letters*, 2002:77-80 (1995).

Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).

UniProtKB/Swiss-Prot entry P18525, pp. 1-3 downloaded from http://www.expasy.org/cgi-bin/niceprot.pl/printable?ac=P18525 on Feb. 8, 1997, "HV54_Mouse" (Nov. 1, 1990).

Urmoneit et al., "Cerebrovascular Smooth Muscle Cells Internalize Alzheimer Amyloid Beta Protein via a Lipoprotein Pathway: Implications for Cerebral Amyloid Angiopathy," *Laboratory Investigation*, 77(2):157-166 (1997).

U.S. Appl. No. 09/316,387, Office Action mailed Sep. 10, 2007.

U.S. Appl. No. 09/316,387, Response to Jun. 20, 2005 Office Action filed Dec. 20, 2005.

U.S. Appl. No. 09/316,387, Declaration of Solomon, Hrncic, and Wall under 37 C.F.R. § 1.131 filed Mar. 6, 2006.

U.S. Appl. No. 09/316,387, Office Action mailed Jun. 20, 2005.

Vajdos et al., "Comprehensive Functional Maps of the Antigen-binging site of an Anti_ErbB2 Antibody Obtained with Shotgun Scanning Mutagenesis," *J. Mol. Biol.*, 320:415-428 (2002).

Valleix et al., "Hereditary renal amyloidosis caused by a new variant lysozyme W64R in a French family," *Kidney International*, 61:907-912 (2002).

Van Den Dobbelsteen et al., "Characteristics of Immune Responses to Native and Protein Conjugated Pneumococcal Polysaccharide Type 14," *Scand. J. Immunol.*, 41:273-280 (1995).

Van Gool et al., "Concentrations of myloid-β protein in cerebrospinal fluid increase with age in patients free from neurodegenerative disease," *Neuroscience Letters*, 172:122-124 (1994).

Van Leuven, F., "Single and multiple transgenic mice as models for Alzheimer's disease," *Progress in Neurobiology*, 61:305-312 (2000).

Van Regenmortel et al, "D-peptides as immunogens and diagnostic reagents " *Curr. Opin. Biotechnol.*, 9(4):377-382 (1998).

Vanderstichele et al., "Standardization of Measurement of B-amyloid(1-42) in Cerebrospinal Fluid and Plasma:," *Int. J. Exp. Clin. Invest.*, 7(4):245-258 (2000).

Vehmas et al., "Beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).

Velazquez et al., "Aspartate residue 7 in Amyloid β-protein is critical for classical complement pathway activation: Implications for Alzheimer's disease pathogenesis," *Nature Medicine*, 3(1):77-79 (1997).

Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).

Verma et al., "Gene therapy—promises, problems and prospects," *Nature*, 389:239-242 (1997).

Vershigora A. E. *Obshchaya Immynologiya*, pp. 35, 229-231 and 152-153 (1990).

Vickers, J. C., "A Vaccine Against Alzheimer's Disease," *Drugs Aging*, 19(7):487-494 (2002).

Vidanovic et al., "Effects of nonionic surfactants on the physical stability of immunoglobulin G in aqueous solution during mechanical agitation," *DIE PHARMAZIE*, 58(6):399-404 (2003).

Walker et al., "Labeling of Cerebral Amyloid *in Vivo* with a Monoclonal Antibody," *J. Neuropath. Exp. Neurology*, 53(4):377-383 (1994).

Walsh et al., "Naturally secreted oligomers of Amyloid β protein potently inhibit hippocampal long-term potentiation in vivo," *Nature*, 416(6880):535-539 (2002).

Wang et al., "The levels of soluble versus insoluble brain Aβ distinguish Alzheimer's disease from normal and pathologic aging," *Experimental Neurology*, 158:328-337 (1999).

Wang et al., "Soluble oligomers of β Amyloid (1-42) inhibit long-term potentiation but not long-term depression in rate dentate gyrus," *Brain Research*, 924:133-140 (2002).

Wang, W., "Instability, stabilization, and formulation of liquid protein pharmaceuticals," *Int. J. Pharmaceutics*, 185(2):129-188 (1999).

Ward et al., "Spontaneous Deletions in IG Heavy Chain Genes Flaking Seuences Influence Splice Site Selection Nucleic Acids Research," 19(23): 6475-6480 (1991).

Washington University in St. Louis School of Medicine, "Study gives Clues to Working of Anti-Alzheimer Antibody," downloaded from www.medicine.wustl.edu/~wumpa/news on Dec. 15, 2004.

*Webster's New World Dictionary*, p. 1387, therapeutic (1988).

*Webster's New World Dictionary of American English*, Third College Edition, p. 1078 (1988).

Weiner et al., "Nasal administration of myloid-β peptide decreases cerebral myloid burden in a mouse model of Alzheimer's disease," *Annals of Neurology*, 48:567-579 (2000).

Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).

Weiner, H. L., "Oral tolerance: immune mechanisms and treatment of autoimmune diseases," *Immunology Today*, 18:335-343 (1997).

Weinreb et al., "NACP, A Protein Implicated in Alzheimer's Disease and Learning, Is Natively Unfolded," *Biochemistry*, 35(43)13709-13715 (1996).

Weissmann et al., "Bovine spongiform encephalopathy and early onset variant Creutzfeldt-Jakob disease," *Curr. Opin. Neurobiol.*, 7:695-700 (1997).

Weldon et al., "Neurotoxicity of Aβ Peptide: Confocal Imaging of Cellular Changes Induced by—Amyloid in Rat CNS *In Vivo*," *Society for Neuroscicence Abstracts*, 22(Part 1) (1996).

Welling et al., "Choice of Peptide and Peptide Length for the Generation of Antibodies Reactive With the Intact Protein," *FEBS Letters*, 182(1):81-84 (Mar. 1985).

Wells, J. A., "Additivity of Mutational Effects in Proteins," *Biochemistry*, 29(37):8509-8517 (1990).

Wen, G.Y., "Alzheimer's Disease and Risk Factors," *J. Food Drug Analysis*, 6(2):465-476 (1998).

Wengenack et al., "Targeting Alzheimer amyloid plaques in vivo," *Nature Biotech.*, 18:868-872 (2000).

White et al., "Immunotherapy as a therapeutic treatment for neurodegenerative disorders," *J. Neurochem.*, 87(4):801-808 (2003).

Wikipedia entry for Antibody, retrieved Apr. 27, 2009 from http://en.wikipedia.org/wiki/Antibody.

Wikipedia definition of "epitope" printed from internet on Apr. 26, 2006.

Wikipedia definition of "antigen" printed from internet on Apr. 26, 2006.

Wikipedia definition of "route of administration including parenteral" printed from internet on Apr. 26, 2006.

Wilson et al., "Phage display: applications, innovations, and issues in phage and host biology," *Can. J. Microbiol*, 44:313-329 (1998).

Winblad et al., "Hints of a therapeutic Vaccine for Alzheimer's?" *Neuron*, 38:517-519 (2003).

Winter et al., "Humanized antibodies" *Immunology Today*, 14(6):243-246 (1996).

Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56 (1969).

Wisniewski et al., "Alzheimer's disease and soluble A beta," *Neurobiol. Aging*, 15(2):143-52 (1994).

Wisniewski et al., "Therapeutics in Alzheimer's and Prion Diseases," *Biochemical Society Transactions*, 30(4):574-587 (2002).

Whitcomb et al., "Characterization of saturable binding sites for circulating pancreatic polypeptide in rat brain," *Am J Pysiol Gastrointest Liver Physiol*, 259:G687-G691 (1990).

Wong et al., "Neuritic Plaques and Cerebrovascular Amyloid in Alzheimer Disease are Antigenically Related," *PNAS*, 82:8729-8732 (1985).

Wood et al., "Amyloid precursor protein processing and Aβ42 deposition in a transgenic mouse model of Alzheimer disease," *PNAS*, 94:1550-1555 (1997).

Wood et al., "Prolines and amyloidogenicily in fragments of the Alzheimer's peptide β/A4" *Biochemistry*, 34:724-730 (1995).

Wu et al., "Humanization of a Murine Monoclonal Antibody by Simultaneous Optimization of Framework and CDR Residues," *J. Mol. Biol.*, 294:151-162 (1999).

Wu et al., "Expression of immunogenic epitopes of hepatitis B surface antigen with hybrid flagellin proteins by a vaccine strain of *Salmonella*," *PNAS*, 86:4726-4730 (1989).

Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).

Wu et al., "An Analysis of the Sequences of the Variable Regions of Bence Jones Proteins and Myeloma Light Chains and their Implications for Antibody Complementarity*" *J. Exp. Med.*, 132:211-250 (1970).

Wyeth, Annual Review 2005: Creating Value . . . Advancing Health (Feb. 27, 2006).

Xiang et al., "Manipulation of the immune response to a plasmid-encoded viral antigen by coinoculation with plasmids expressing cytokines," *Immunity*, 2(2):129-135 Abstract (1995).

Xu et al., "Increased incidence of anti-β-amyloid autoantibodies secreted by Epstein-Barr virus transformed B cell lines from patients with Alzheimer's disease " *Mechanisms of Ageing and Development*, 94:213-222 (1997).

Yamada et al., "Generation and Characterization of Rat Monoclonal Antibodies Against Human Serum Amyloid A," *Scand. J. Immunol.*, 46(2):175-179 (1997).

Yamaguchi et al., Diffuse plaques associated with astroglial amyloid β protein, possibly showing a disappearing stage of senile plaques, *Acta Neuropathol.*, 95:217-222 (1998).

Yanagisawa K et al., "Amyloid BETA-protein (Alpha-Beta) associated with lipid molecules: immunoreactivity distinct from that of soluble Alpha-Beta," FEBS Letters, 1(420): 43-46 (1997).

Yang et al., "Effects of Racemization on the Aggregational Properties of the Amyloid β-Peptide in Alzheimer's Disease," abstract # 255 from American Chemical Society 214th National Meeting (1997).

Yang et al., "Monoclonal Antibody to the C-terminus of Beta-Amyloid," Neuroreport, 16(5):2117-2120 (1994).

Yankner et al., "Neurotrophic and Neurotoxic effects of Amyloid β Protein: Reversal by Tachykinin Neuropeptides," *Science*, 250:279-282 (1990).

Younkin, "Amyloid β vaccination: reduced plaques and improved cognition," *Nature Medicine*, 7:18-19 (2001).

Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therapeutic Strategies-Therapeutic Strategies, Amyloid-Based, also *Neurobiology of Aging*, 25(Suppl. 2): p. S593 (Jul. 2004).

Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).

Zhang et al., "A novel recombinant adeno-associated virus vaccine reduces behavioral impairment and β-amyloid plaques in a mouse model of Alzheimer's disease," *Neurobiology of Disease*, 14:365-379 (2003).

Zlokovic et al., "Clearance of amyloid β-peptide from brain: transport or metabolism?," *Nature Medicine*, 6(7):718-719 (2000).

Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.

U.S. Appl. No. 09/724,319, Office Action mailed Dec. 21, 2010.
U.S. Appl. No. 10/544,093, Office Action Mailed Oct. 13, 2010.
Aquila Press Release, PR Newswire. May 6, 1997.
Aylward et al., "Cerebellar Volume in Adults With Down Syndrome," *Arch Neurol.*, 4(2):209-212 (1997), Abstract only.
Bach et al., "Vaccination with AB-Displaying Virus-Like Particles Reduces Soluble and Insoluble Cerebral AB and Lowers Plaque Burden in APP Transgenic Mice," J. Immunol., 2009, 182 7613-7624.
Boraschi et al., "Interleukin-1 and Interleukin-1 Fragments a Vaccine Adjuvants", Methods, 1999, 19, pp. 108-113.
Constantino, Expert opinion Sep. 17, 2010.
Cribbs et al., "Adjuvant-dependant modulation of th1 and th2 responses to immunization with B-amyloid", International Immunology, 2003, vol. 15, No. 4, pp. 505-514.
Do et al., "Reprogramming Somatic Gene Activity by Fusion With Pluripotent Cells" *Stem Cell Reviews.*, 2:257-267 (2006).
Greenberg et al. "Amyloid Angiopathy-Related Vascular Congnitive Impairment" Stoke., 35:2616-2619 (2004).

Hartwig, "Immune ageing and Alzheimer's disease," *NeuroReport*, 6:1274-1276 (1995).

Holm et al., "Functional Mapping and Single Chain Construction of the Anti-Cytokeratin 8 Monoclonal Antibody TS1," *Mol. Immunol.*, 44(6):1075-1084 (Feb. 2007).

Kim et al., "In Vivo Engineering of a Cellular Immune Response by Coadministration of IL-12 Expression Vector with a DNA Immunogen," *J. Immunol.*, 158:816-826 (1997).

Kinnecom et al., "Course of Cerebral Amyloid Angiopathy? Related Inflation," *Neurology*, 68(17):1411-1416 (2007).

Kofke et al., "Remifentanil-Induced Cerebral Blood Flow Effects in Normal Humans: Dose and ApoE genotype," *Neurosurg Anesthes Neurosci.*, 105(1):167-175 (2007).

Lemere, "Developing novel immunogens for a safe and effective Alzheimer's disease vaccine" Prog Brain Res. 2009; 175: 83 1-13.

Movsesyan et al., "Reducing AD-Lide Pathology in 3xTg-AD Mouse Model by DNA epitope Vaccine—A Novel Immunotherapeutic Strategy", PloS ONE, 2008, vol. 3, issue 5, e2124 1-13.

PCT Search Report of Mar. 25, 2009 for application PCT/US2008/80382.

PCT Written Opinion of Mar. 8, 2009 for application PCT/US2008/80382.

Ramshaw et al., "DNA vaccines for the treatment of autoimmune disease," *Immunology and Cell Biology* 75:409-413 (1997).

Tam, "Synthetic peptide vaccine design: synthesis and properties of a high-density multiple antigenic peptide system", Proc. Natl. Acad. Sci., 1988, vol. 85, pp. 5409-5413.

Viswanathan et al., "Cerebral Microhemorrhage", *Stroke.*, 37:550-555 (2006).

Wang et al, "Site-specific UBITh amyloid-α vaccine for immunotherapy of Alzheimer's disease" *Vaccine* 25 (2007) 3041-3052.

Wehner, Declaration May 21, 2007.
U.S. Appl. No. 11/842,116, Office Action mailed Mar. 31, 2010.
U.S. Appl. No. 09/322,289, Notice of Allowance mailed Nov. 15, 2010.
U.S. Appl. No. 10/858,855, Notice of Allowance mailed Jul. 12, 2010.
U.S. Appl. No. 11/842,023, Notice of Allowance mailed Oct. 6, 2010.
U.S. Appl. No. 12/181,238, Notice of Allowance mailed Mar. 5, 2010.
U.S. Appl. No. 09/723,765, BPAI Decision on Request for Re-hearing mailed Oct. 16, 2007.
U.S. Appl. No. 09/723,765, BPAI Order Returning Appeal to Examiner mailed Jun. 27, 2006.
U.S. Appl. No. 09/723,765, Examiners Answer mailed Jan. 25, 2006.
U.S. Appl. No. 09/723,765, Reply Brief Noted mailed Jun. 16, 2006.
U.S. Appl. No. 10/777,792, BPAI Decision mailed Aug. 30, 2010.
U.S. Appl. No. 10/777,792, Decision on Request for Reconsideration mailed Nov. 30, 2010.
U.S. Appl. No. 10/777,792, Examiners Answer mailed Oct. 27, 2009.
U.S. Appl. No. 10/777,792, Reply Brief Noted mailed Jan. 11, 2010.
U.S. Appl. No. 10/923,469, BPAI Decision mailed Feb. 22, 2011.
U.S. Appl. No. 10/923,469, Reply Brief Noted mailed Mar. 9, 2010.
U.S. Appl. No. 10/429,216, Office Action mailed Sep. 15, 2010.
U.S. Appl. No. 11/245,524, Office Action mailed Dec. 10, 2010.
U.S. Appl. No. 11/245,916, Office Action mailed May 18, 2010.
U.S. Appl. No. 11/245,916, Office Action mailed Dec. 14, 2011.
U.S. Appl. No. 111/842,113, Office Action mailed Aug. 24, 2010.

\* cited by examiner

SEQUENCE LISTING

<160> NUMBER OF SEQ ID NOS: 53

<210> SEQ ID NO 1
<211> LENGTH: 112
<212> TYPE: PRT
<213> ORGANISM: Artificial
<220> FEATURE:
<223> OTHER INFORMATION: Synthetic Humanized 3D6 Light Chain Variable
      Region (version 1)

<400> SEQUENCE: 1

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

<210> SEQ ID NO 2
<211> LENGTH: 119
<212> TYPE: PRT
<213> ORGANISM: Artificial
<220> FEATURE:
<223> OTHER INFORMATION: Synthetic Humanized 3D6 Heavy Chain Variable
      Region (version 1)

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 3
<211> LENGTH: 112
<212> TYPE: PRT
<213> ORGANISM: Artificial
<220> FEATURE:
<223> OTHER INFORMATION: Synthetic Humanized 3D6 Light Chain Variable
      Region (version 2)

-continued

<400> SEQUENCE: 3

```
Tyr Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110
```

<210> SEQ ID NO 4
<211> LENGTH: 119
<212> TYPE: PRT
<213> ORGANISM: Artificial
<220> FEATURE:
<223> OTHER INFORMATION: Synthetic Humanized 3D6 Heavy Chain Variable
      Region (version 2)

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115
```

<210> SEQ ID NO 5
<211> LENGTH: 219
<212> TYPE: PRT
<213> ORGANISM: Artificial
<220> FEATURE:
<223> OTHER INFORMATION: Synthetic Humanized 3D6 Light Chain

<400> SEQUENCE: 5

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Phe Pro Arg Thr Phe Gly Gly Gly Thr Lys Val Glu Ile Lys
           100                 105                 110

Arg Thr Val Ala Ala Pro Ser Val Phe Ile Phe Pro Pro Ser Asp Glu
       115                 120                 125

Gln Leu Lys Ser Gly Thr Ala Ser Val Val Cys Leu Leu Asn Asn Phe
   130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
           180                 185                 190

Lys His Lys Val Tyr Ala Cys Glu Val Thr His Gln Gly Leu Ser Ser
       195                 200                 205

Pro Val Thr Lys Ser Phe Asn Arg Gly Glu Cys
   210                 215

<210> SEQ ID NO 6
<211> LENGTH: 449
<212> TYPE: PRT
<213> ORGANISM: Artificial
<220> FEATURE:
<223> OTHER INFORMATION: Synthetic Humanized 3D6 Heavy Chain

<400> SEQUENCE: 6

Gln Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg Tyr Asp His Tyr Ser Gly Ser Ser Asp Tyr Trp Gly Gln Gly
           100                 105                 110

Thr Leu Val Thr Val Ser Ser Ala Ser Thr Lys Gly Pro Ser Val Phe
       115                 120                 125

Pro Leu Ala Pro Ser Ser Lys Ser Thr Ser Gly Gly Thr Ala Ala Leu
   130                 135                 140

Gly Cys Leu Val Lys Asp Tyr Phe Pro Gln Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
           180                 185                 190

Ser Ser Leu Gly Thr Gln Thr Tyr Ile Cys Asn Val Asn His Lys Pro
       195                 200                 205

Ser Asn Thr Lys Val Asp Lys Lys Val Glu Pro Lys Ser Cys Asp Lys

```
              210                 215                 220
Thr His Thr Cys Pro Pro Cys Pro Ala Pro Gln Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 7
<211> LENGTH: 112
<212> TYPE: PRT
<213> ORGANISM: Artificial
<220> FEATURE:
<223> OTHER INFORMATION: Synthetic Humanized 12A11 Light Chain

<400> SEQUENCE: 7

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Ser His Val Pro Leu Thr Phe Gly Gln Gly Thr Lys Leu Glu Ile Lys
                100                 105                 110

<210> SEQ ID NO 8
<211> LENGTH: 120
```

```
<212> TYPE: PRT
<213> ORGANISM: Artificial
<220> FEATURE:
<223> OTHER INFORMATION: Synthetic Humanized 12A11 Heavy Chain
      (version 1)

<400> SEQUENCE: 8
```

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

```
<210> SEQ ID NO 9
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 2)

<400> SEQUENCE: 9
```

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

```
<210> SEQ ID NO 10
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 2.1)

<400> SEQUENCE: 10
```

Gln Val Gln Leu Val Glu Ser Gly Gly Gly Val Val Gln Pro Gly Arg
1               5                   10                  15

```
Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
 50                  55                  60

Leu Lys Ser Arg Phe Thr Ile Ser Lys Asp Asn Ser Lys Asn Thr Leu
 65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 11
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 3)

<400> SEQUENCE: 11

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
 50                  55                  60

Leu Lys Ser Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 12
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 4.1)

<400> SEQUENCE: 12

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
 50                  55                  60
```

```
Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 13
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 4.2)

<400> SEQUENCE: 13

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
             35                  40                  45

Trp Val Ala His Ile Trp Trp Asp Asp Lys Tyr Tyr Asn Pro Ser
     50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 14
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 4.3)

<400> SEQUENCE: 14

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
             35                  40                  45

Trp Leu Ala His Ile Trp Trp Asp Asp Lys Tyr Tyr Asn Pro Ser
     50                  55                  60

Leu Lys Ser Arg Phe Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
```

<210> SEQ ID NO 15
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 4.4)

<400> SEQUENCE: 15

Gln Val Gln Leu Val Glu Ser Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 16
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 5.1)

<400> SEQUENCE: 16

Gln Val Gln Leu Val Glu Ser Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 17
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 5.2)

-continued

```
<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 18
<211> LENGTH: 121
<212> TYPE: PRT
<213> ORGANISM: Artificial
<220> FEATURE:
<223> OTHER INFORMATION: Synthetic Humanized 12A11 Heavy Chain
      (version 5.3)

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 19
<211> LENGTH: 121
<212> TYPE: PRT
<213> ORGANISM: Artificial
<220> FEATURE:
<223> OTHER INFORMATION: Synthetic Humanized 12A11 Heavy Chain
      (version 5.4)

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
```

```
                35                  40                  45
Trp Val Ala His Ile Trp Trp Asp Asp Lys Tyr Tyr Asn Pro Ser
 50                  55                  60
Leu Lys Ser Arg Phe Thr Ile Ser Lys Asp Thr Ser Lys Asn Thr Val
65                  70                  75                  80
Tyr Leu Gln Met Asn Ser Leu Arg Ala Glu Asp Thr Ala Val Tyr Tyr
                85                  90                  95
Cys Ala Arg Arg Thr Thr Thr Ala Asp Tyr Phe Ala Tyr Trp Gly Gln
            100                 105                 110
Gly Thr Thr Val Thr Val Ser Ser Val
            115                 120
```

<210> SEQ ID NO 20
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 5.5)

<400> SEQUENCE: 20

```
Gln Val Gln Leu Val Glu Ser Gly Gly Gly Val Val Gln Pro Gly Arg
 1               5                  10                  15
Ser Leu Arg Leu Ser Cys Ala Phe Ser Gly Phe Ser Leu Ser Thr Ser
                20                  25                  30
Gly Met Ser Val Gly Trp Ile Arg Gln Ala Pro Gly Lys Gly Leu Glu
                35                  40                  45
Trp Val Ala His Ile Trp Trp Asp Asp Lys Tyr Tyr Asn Pro Ser
 50                  55                  60
Leu Lys Ser Arg Leu Thr Ile Ser Lys Asp Thr Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Arg Arg Thr Thr Thr Ala Asp Tyr Phe Ala Tyr Trp Gly Gln
            100                 105                 110
Gly Thr Thr Val Thr Val Ser Ser
            115                 120
```

<210> SEQ ID NO 21
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 5.6)

<400> SEQUENCE: 21

```
Gln Val Gln Leu Val Glu Ser Gly Gly Gly Val Val Gln Pro Gly Arg
 1               5                  10                  15
Ser Leu Arg Leu Ser Cys Ala Phe Ser Gly Phe Ser Leu Ser Thr Ser
                20                  25                  30
Gly Met Ser Val Gly Trp Ile Arg Gln Ala Pro Gly Lys Gly Leu Glu
                35                  40                  45
Trp Leu Ala His Ile Trp Trp Asp Asp Lys Tyr Tyr Asn Pro Ser
 50                  55                  60
Leu Lys Ser Arg Phe Thr Ile Ser Lys Asp Thr Ser Lys Asn Thr Leu
65                  70                  75                  80
Tyr Leu Gln Met Asn Ser Leu Arg Ala Glu Asp Thr Ala Val Tyr Tyr
                85                  90                  95
```

-continued

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 22
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 6.1)

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 23
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 6.2)

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 24
<211> LENGTH: 120

-continued

```
<212> TYPE: PRT
<213> ORGANISM: Artificial
<220> FEATURE:
<223> OTHER INFORMATION: Synthetic Humanized 12A11 Heavy Chain
      (version 6.3)

<400> SEQUENCE: 24
```

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

```
<210> SEQ ID NO 25
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 6.4)

<400> SEQUENCE: 25
```

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

```
<210> SEQ ID NO 26
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 7)

<400> SEQUENCE: 26
```

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Val Arg Gln Ala Pro Gly Lys Gly Leu Glu
            35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 27
<211> LENGTH: 120
<212> TYPE: PRT
<213> ORGANISM: Artificial
<220> FEATURE:
<223> OTHER INFORMATION: Synthetic Humanized 12A11 Heavy Chain
      (version 8)

<400> SEQUENCE: 27

Gln Val Gln Leu Val Glu Ser Gly Gly Gly Val Val Gln Pro Gly Arg
 1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Asn Ser Lys Asn Thr Val
 65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 28
<211> LENGTH: 43
<212> TYPE: PRT
<213> ORGANISM: Homo sapiens

<400> SEQUENCE: 28

Asp Ala Glu Phe Arg His Asp Ser Gly Tyr Glu Val His His Gln Lys
 1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 29
<211> LENGTH: 16
<212> TYPE: PRT
<213> ORGANISM: Plasmodium sp.

<400> SEQUENCE: 29

Glu Lys Lys Ile Ala Lys Met Glu Lys Ala Ser Ser Val Phe Asn Val
1               5                   10                  15

<210> SEQ ID NO 30
<211> LENGTH: 10
<212> TYPE: PRT
<213> ORGANISM: Hepatitis B virus

<400> SEQUENCE: 30

Phe Phe Leu Leu Thr Arg Ile Leu Thr Ile
1               5                   10

<210> SEQ ID NO 31
<211> LENGTH: 19
<212> TYPE: PRT
<213> ORGANISM: Homo sapiens

<400> SEQUENCE: 31

Asp Gln Ser Ile Gly Asp Leu Ile Ala Glu Ala Met Asp Lys Val Gly
1               5                   10                  15

Asn Glu Gly

<210> SEQ ID NO 32
<211> LENGTH: 14
<212> TYPE: PRT
<213> ORGANISM: Mycobacterium bovis

<400> SEQUENCE: 32

Gln Val His Phe Gln Pro Leu Pro Pro Ala Val Val Lys Leu
1               5                   10

<210> SEQ ID NO 33
<211> LENGTH: 15
<212> TYPE: PRT
<213> ORGANISM: Clostridium tetani

<400> SEQUENCE: 33

Gln Tyr Ile Lys Ala Asn Ser Lys Phe Ile Gly Ile Thr Glu Leu
1               5                   10                  15

<210> SEQ ID NO 34
<211> LENGTH: 21
<212> TYPE: PRT
<213> ORGANISM: Clostridium tetani

<400> SEQUENCE: 34

Phe Asn Asn Phe Thr Val Ser Phe Trp Leu Arg Val Pro Lys Val Ser
1               5                   10                  15

Ala Ser His Leu Glu
            20

<210> SEQ ID NO 35
<211> LENGTH: 16
<212> TYPE: PRT
<213> ORGANISM: Human immunodeficiency virus

<400> SEQUENCE: 35

Lys Gln Ile Ile Asn Met Trp Gln Glu Val Gly Lys Ala Met Tyr Ala
1               5                   10                  15

<210> SEQ ID NO 36
<211> LENGTH: 22
<212> TYPE: PRT

```
<213> ORGANISM: Artificial
<220> FEATURE:
<223> OTHER INFORMATION: Synthetic fusion protein (AB1-7 - Tetanus
      toxoid 830-844)

<400> SEQUENCE: 36

Asp Ala Glu Phe Arg His Asp Gln Tyr Ile Lys Ala Asn Ser Lys Ph

<223> OTHER INFORMATION: Xaa = cyclohexylalanine, tyrosine or
      phenylalanine

<400> SEQUENCE: 40

Asp Ala Glu Phe Arg His Asp Ala Glu Phe Arg His Asp Ala
1               5                   10                  15

Glu Phe Arg His Asp Ala Lys Xaa Val Ala Ala Trp Thr Leu Lys Ala
                20                  25                  30

Ala Ala

<210> SEQ ID NO 41
<211> LENGTH: 34
<212> TYPE: PRT
<213> ORGANISM: Artificial
<220> FEATURE:
<223> OTHER INFORMATION: Synthetic fusion protein
<220> FEATURE:
<221> NAME/KEY: MISC_FEATURE
<222> LOCATION: (3)..(3)
<223> OTHER INFORMATION: Xaa = cyclohexylalanine, tyrosine or
      phenylalanine

<400> SEQUENCE: 41

Ala Lys Xaa Val Ala Ala Trp Thr Leu Lys Ala Ala Asp Ala Glu
1               5                   10                  15

Phe Arg His Asp Asp Ala Glu Phe Arg His Asp Ala Glu Phe Arg
                20                  25                  30

His Asp

<210> SEQ ID NO 42
<211> LENGTH: 20
<212> TYPE: PRT
<213> ORGANISM: Artificial
<220> FEATURE:
<223> OTHER INFORMATION: Synthetic fusion protein
<220> FEATURE:
<221> NAME/KEY: MISC_FEATURE
<222> LOCATION: (10)..(10)
<223> OTHER INFORMATION: Xaa = cyclohexylalanine, tyrosine or
      phenylalanine

<400> SEQUENCE: 42

Asp Ala Glu Phe Arg His Asp Ala Lys Xaa Val Ala Ala Trp Thr Leu
1               5                   10                  15

Lys Ala Ala Ala
            20

<210> SEQ ID NO 43
<211> LENGTH: 24
<212> TYPE: PRT
<213> ORGANISM: Artificial
<220> FEATURE:
<223> OTHER INFORMATION: Synthetic fusion protein

<400> SEQUENCE: 43

Asp Ala Glu Phe Arg His Asp Ile Ser Gln Ala Val His Ala Ala His
1               5                   10                  15

Ala Glu Ile Asn Glu Ala Gly Arg
            20

<210> SEQ ID NO 44
<211> LENGTH: 24
<212> TYPE: PRT
<213> ORGANISM: Artificial
<220> FEATURE:
<223> OTHER INFORMATION: Synthetic fusion protein

```
-continued

<400> SEQUENCE: 44

Phe Arg His Asp Ser Gly Tyr Ile Ser Gln Ala Val His Ala Ala His
1               5                   10                  15

Ala Glu Ile Asn Glu Ala Gly Arg
            20

<210> SEQ ID NO 45
<211> LENGTH: 24
<212> TYPE: PRT
<213> ORGANISM: Artificial
<220> FEATURE:
<223> OTHER INFORMATION: Synthetic fusion protein

<400> SEQUENCE: 45

Glu Phe Arg His Asp Ser Gly Ile Ser Gln Ala Val His Ala Ala His
1               5                   10                  15

Ala Glu Ile Asn Glu Ala Gly Arg
            20

<210> SEQ ID NO 46
<211> LENGTH: 34
<212> TYPE: PRT
<213> ORGANISM: Artificial
<220> FEATURE:
<223> OTHER INFORMATION: Synthetic fusion protein

<400> SEQUENCE: 46

Pro Lys Tyr Val Lys Gln Asn Thr Leu Lys Leu Ala Thr Asp Ala Glu
1               5                   10                  15

Phe Arg His Asp Asp Ala Glu Phe Arg His Asp Asp Ala Glu Phe Arg
            20                  25                  30

His Asp

<210> SEQ ID NO 47
<211> LENGTH: 27
<212> TYPE: PRT
<213> ORGANISM: Artificial
<220> FEATURE:
<223> OTHER INFORMATION: Synthetic fusion protein

<400> SEQUENCE: 47

Asp Ala Glu Phe Arg His Asp Pro Lys Tyr Val Lys Gln Asn Thr Leu
1               5                   10                  15

Lys Leu Ala Thr Asp Ala Glu Phe Arg His Asp
            20                  25

<210> SEQ ID NO 48
<211> LENGTH: 34
<212> TYPE: PRT
<213> ORGANISM: Artificial
<220> FEATURE:
<223> OTHER INFORMATION: Synthetic fusion protein

<400> SEQUENCE: 48

Asp Ala Glu Phe Arg His Asp Asp Ala Glu Phe Arg His Asp Asp Ala
1               5                   10                  15

Glu Phe Arg His Asp Pro Lys Tyr Val Lys Gln Asn Thr Leu Lys Leu
            20                  25                  30

Ala Thr

<210> SEQ ID NO 49
<211> LENGTH: 27
```

```
<212> TYPE: PRT
<213> ORGANISM: Artificial
<220> FEATURE:
<223> OTHER INFORMATION: Synthetic fusion protein

<400> SEQUENCE: 49

Asp Ala Glu Phe Arg His Asp Ala Glu Phe Arg His Asp Pro Lys
1               5                   10                  15

Tyr Val Lys Gln Asn Thr Leu Lys Leu Ala Thr
            20                  25

<210> SEQ ID NO 50
<211> LENGTH: 79
<212> TYPE: PRT
<213> ORGANISM: Artificial
<220> FEATURE:
<223> OTHER INFORMATION: Synthetic fusion protein

<400> SEQUENCE: 50

Asp Ala Glu Phe Arg His Asp Pro Lys Tyr Val Lys Gln Asn Thr Leu
1               5                   10                  15

Lys Leu Ala Thr Glu Lys Lys Ile Ala Lys Met Glu Lys Ala Ser Ser
                20                  25                  30

Val Phe Asn Val Gln Tyr Ile Lys Ala Asn Ser Lys Phe Ile Gly Ile
35                  40                  45

Thr Glu Leu Phe Asn Asn Phe Thr Val Ser Phe Trp Leu Arg Val Pro
50                  55                  60

Lys Val Ser Ala Ser His Leu Glu Asp Ala Glu Phe Arg His Asp
65                  70                  75

<210> SEQ ID NO 51
<211> LENGTH: 56
<212> TYPE: PRT
<213> ORGANISM: Artificial
<220> FEATURE:
<223> OTHER INFORMATION: Synthetic fusion protein

<400> SEQUENCE: 51

Asp Ala Glu Phe Arg His Asp Ala Glu Phe Arg His Asp Ala
1               5                   10                  15

Glu Phe Arg His Asp Gln Tyr Ile Lys Ala Asn Ser Lys Phe Ile Gly
                20                  25                  30

Ile Thr Glu Leu Asn Asn Phe Thr Val Ser Phe Trp Leu Arg Val Pro
        35                  40                  45

Lys Val Ser Ala Ser His Leu Glu
    50                  55

<210> SEQ ID NO 52
<211> LENGTH: 44
<212> TYPE: PRT
<213> ORGANISM: Artificial
<220> FEATURE:
<223> OTHER INFORMATION: Synthetic fusion protein

<400> SEQUENCE: 52

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
                20                  25                  30

Leu Arg Val Pro Lys Val Ser Ala Ser His Leu Glu
            35                  40
```

-continued

```
<210> SEQ ID NO 53
<211> LENGTH: 51
<212> TYPE: PRT
<213> ORGANISM: Artificial
<220> FEATURE:
<223> OTHER INFORMATION: Synthetic fusion protein

<400> SEQUENCE: 53

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu Asp Ala Glu Phe
        35                  40                  45

Arg His Asp
    50
```

TREATMENT OF CEREBRAL AMYLOID ANGIOPATHY

CROSS-REFERENCE TO RELATED APPLICATIONS

This application is a continuation-in-part of U.S. application Ser. No. 12/106,206 filed Apr. 18, 2008, which claims benefit under 35 U.S.C. §119(e) of U.S. Provisional Patent Application Ser. No. 60/925,228, filed Apr. 18, 2007, each of which is incorporated herein by reference in its entirety for all purposes.

REFERENCE TO A "SEQUENCE LISTING" A TABLE, OR A COMPUTER PROGRAM LISTING

The Sequence Listing written in file SEQLIST15270C000320US.txt is 45,052 bytes, and was created on Sep. 18, 2008, for application Ser. No. 12/181,238, Schroeter et al, entitled "PREVENTION AND TREATMENT OF CEREBRAL AMYLOID ANGIOPATHY". The information contained in this file is hereby incorporated by reference.

BACKGROUND OF THE INVENTION

Over expression of mutant human amyloid precursor protein (APP) in various transgenic mice leads to several Alzheimer's disease (AD)-type lesions [for reviews see D. Games et al., *J Alzheimers Dis* 9, 133-49 (2006); J. Gotz et al., *Mol Psychiatry* 9, 664-83 (2004). These include the development of parenchymal amyloid-beta (A$\beta$) plaques, neuritic pathology, synaptic loss, and gliosis. A number of reports have shown that active (see D. Schenk et al., *Nature* 400, 173-7 (1999); D. L. Dickstein et al., *Faseb J* 20, 426-33 (2006)) and passive (see F. Bard et al., *Nat Med* 6, 916-9 (2000); M. Buttini et al., *J Neurosci* 25, 9096-101 (2005); D. M. Wilcock et al, *J Neuroinflammation* 1, 24 (2004)) A$\beta$ immunotherapeutic approaches are effective in reducing or eliminating these pathologies in preclinical studies (see R. P. Brendza & D. M. Holzman, *Alzheimer Dis Assoc Disord* 20, 118-23 (2006); C. A. Lernere et al., *Rejuvenation Res* 9, 77-84 (2006)). In addition, many studies have shown improvement in various cognitive tests (see D. M. Wilcock et al, supra; C. Janus et al., *Nature* 408, 979-82 (2000); D. Morgan et al., *Nature* 408, 982-5 (2000)). These findings are supported by mounting correlative findings from both memory testing and neuropathological examination of brains of patients who were enrolled in clinical trials of A$\beta$ immunotherapy (AN1792), see J. A. Nicoll et al., *Nat Med* 9, 448-52 (2003); I. Ferrer et al., *Brain Pathol* 14, 11-20 (2004); S. Gilman et al., *Neurology* 64, 1553-62 (2005).

Recently another common aspect of AD pathology, vascular A$\beta$ (VA$\beta$), has been the subject of scrutiny in preclinical APP transgenic animal studies. In particular, it has been reported that passive immunization has been associated with an increase in VA$\beta$ and microhemorrhage (see D. M. Wilcock et al, supra; M. M. Racke et al., *J Neurosci* 25, 629-36 (2005)). However, predictive clinical implications remain unclear, especially in light of favorable behavioral outcomes in some of these same studies (see D. M. Wilcock et al, supra), the lack of ultrastructural differences in vascular morphology of hemosiderin-positive vessels in untreated and treated transgenic mice (see G. J. Burbach et al., *Neurobiol Aging* 28, 202-12 (2007)) and, notably, the lack of evidence for significant bleeding or stroke-related consequences in ongoing clinical trials. In addition, little is known about the degree to which VA$\beta$ is ultimately affected by A$\beta$ immunotherapeutic approaches; for example, whether outcome measures in chronic treatment paradigms might differ from more acute studies. For instance, it is unknown whether reported increases in VA$\beta$ represent a transient phenomenon associated with A$\beta$ clearance, while longer treatment might actually prevent or reverse vascular amyloid. Finally, VA$\beta$ effects in transgenic mice may also vary according to the APP mutation employed, since the relative degree of A$\beta$40 versus A$\beta$42 production likely influences both the aggregation properties of A$\beta$ as well as the binding efficiency of certain antibodies, particularly those with C-terminal epitopes.

BRIEF SUMMARY OF THE INVENTION

The invention provides methods of therapeutically treating CAA. The methods comprise administering to a patient having or suspected of having CAA an effective regime of an agent. In some methods the agent is an antibody that is specific for the N-terminus of A$\beta$ and thereby treating the patient. Optionally, the agent is an antibody that binds within residues 1-5 of A$\beta$. Optionally, the antibody is a humanized, human, or chimeric antibody. Optionally, the humanized antibody is 3D6. Optionally, the 3D6 humanized antibody is bapineuzumab. Optionally, the humanized antibody is 12A11.

In some methods, the agent is a fragment of A$\beta$. Optionally, the fragment begins at residue 1 of A$\beta$ and ends at one of residues 5-10 of A$\beta$. Optionally, the fragment is A$\beta$ 1-7. Optionally, the A$\beta$ fragment is administered with a pharmaceutically acceptable adjuvant. Optionally, the A$\beta$ fragment is linked to a carrier that helps the fragment induce antibodies to the fragment. Optionally, the carrier is linked to the C-terminus of the A$\beta$ fragment.

Some methods of the invention further comprise determining that a patient has CAA, wherein the determining step occurs before the administration step. In some methods, the determining step determines that a patient is suffering from a clinical symptom of CAA.

In some methods of therapeutically treating CAA the patient lacks plaques characteristic of Alzheimer's disease in the brain. Optionally, the patient lacks plaques characteristic of Alzheimer's disease in the brain and the patient lacks symptoms of Alzheimer's disease. In some methods of therapeutically treating CAA, the patient has had a heart attack or stroke.

Optionally, the methods comprise administering a dosage of the antibody is between about 0.01 to about 5 mg/kg. Optionally, the methods comprise administering a dosage of the antibody between about 0.1 to about 5 mg/kg. Optionally, the methods comprise administering a dosage of about 0.5 mg/kg. Optionally, the methods comprise administering a dosage of about 1.5 mg/kg. Optionally, the methods comprise administering a dosage between about 0.5 to about 3 mg/kg. Optionally, the methods comprise administering a dosage between about 0.5 to about 1.5 mg/kg. Optionally, the methods comprise administering an antibody on multiple occasions. Optionally, the antibody is administered is weekly to quarterly. Optionally, the antibody is administered every 13 weeks. Optionally, the antibody is administered intravenously or subcutaneously.

Optionally, the antibody is administered in a regime sufficient to maintain an average serum concentration of the antibody in the patient in a range of 1-15 µg antibody/ml serum and thereby treating the patient. Optionally, the average serum concentration is within a range of 1-10 µg antibody/ml serum. Optionally, the average serum concentration is within a range of 1-5 µg antibody/ml serum. Optionally, the average serum concentration is within a range of 2-4 µg antibody/ml serum. Optionally, the antibody is administered in a regime sufficient to maintain average serum concentration of the antibody is maintained for at least one year. Optionally, the average serum concentration of the antibody is maintained for at least six months In some methods where agent is an antibody, optionally, further comprise measuring the concentration of antibody in the serum and adjusting the regime if the measured concentration falls outside the range. In some methods where agent is an antibody, optionally, further comprise measuring the concentration of antibody in the serum and adjusting the regime if the measured concentration falls outside the range.

Optionally, the antibody is administered intravenously in a regime sufficient to maintain an average serum concentration of the antibody in the patient in a range of 1-15 µg antibody/ml serum and thereby treating the patient. Optionally, a dose of 0.5-1.0 mg/kg is administered intravenously monthly. Optionally, a dose of 0.1-1.0 mg/kg is administered intravenously monthly.

Optionally, the antibody is administered subcutaneously. Optionally, the antibody is administered subcutaneously at a frequency between weekly and monthly. Optionally, the antibody is administered subcutaneously weekly or biweekly. Optionally, the antibody is administered subcutaneously at a dose of between about 0.01 to about 0.35 mg/kg. Optionally, the antibody is administered subcutaneously at a dose of between about 0.05 to about 0.25 mg/kg. Optionally, the antibody is administered subcutaneously at a dose of between about 0.015 to about 0.2 mg/kg weekly to biweekly. Optionally, the antibody is administered subcutaneously at a dose of between about 0.05 to about 0.15 mg/kg weekly to biweekly. Optionally, the antibody is administered subcutaneously at a dose of between about 0.05 to about 0.07 mg/kg weekly. Optionally, the antibody is administered subcutaneously at a dose of 0.06 mg/kg weekly. Optionally, the antibody is administered subcutaneously at a dose of between about 0.1 to about 0.15 mg/kg biweekly.

Optionally, the antibody is administered subcutaneously at a dose of between about 0.01 to about 0.6 mg/kg and a frequency of between weekly and monthly. Optionally, the antibody is administered subcutaneously at a dose of between about 0.05 to about 0.25 mg/kg. Optionally, the antibody is administered subcutaneously at a dose of between about 0.015 to about 0.2 mg/kg weekly to biweekly. Optionally, the antibody is administered subcutaneously at a dose of between about 0.05 to about 0.15 mg/kg weekly to biweekly. Optionally, the antibody is administered subcutaneously at a dose of between about 0.05 and about 0.07 mg/kg weekly. Optionally, the antibody is administered subcutaneously at a dose of 0.06 mg/kg weekly. Optionally, the antibody is administered subcutaneously at a dose of between about 0.1 to about 0.15 mg/kg biweekly. Optionally, the antibody is administered subcutaneously at a dose of between about 0.1 to about 0.3 mg/kg monthly. Optionally, the antibody is administered at a dose of 0.2 mg/kg monthly.

Some methods of the invention further comprise monitoring for changes in signs or symptoms of CAA responsive to the administrating step. Some methods of the invention further comprise administering a second agent effective to treat CAA.

The invention provides methods of effecting prophylaxis against CAA. The methods comprise administering to a patient susceptible to CAA an effective regime of an agent. The agent is antibody that is specific for the N-terminus of Aβ or the agent induces such an antibody after administration to the patient and thereby effecting prophylaxis of the patient.

The invention provides for the use of an agent, wherein the agent is an antibody that is specific for the N-terminus of Aβ or induces such an antibody after administration to the patient, in the treatment or prophylaxis of Alzheimer's disease.

The invention provides methods of reducing vascular amyloid in a patient. The methods comprise administering an antibody that is specific for the N-terminus of Aβ in a treatment regime associated with efficacious vascular amyloid removal and reduced incidence of cerebral microhemorrhage. Some methods further comprise monitoring the patient for cerebral microhemorrhage by MRI. Some methods further comprise monitoring the patient for vascular amyloid removal by PET scan. Optionally, in some methods the treatment regime is a chronic treatment regime. Optionally, in some methods the treatment regime comprises an antibody dosage between 0.01 and 5 mg/kg body weight of the patient and administered weekly to quarterly. Optionally, in some methods the dosage of the antibody is 0.1 to 5 mg/kg. Optionally, in some methods the dosage is about 0.5 mg/kg. Optionally, in some methods the dosage is about 1.5 mg/kg. Optionally, in some methods the dosage is between about 0.5 to about 3 mg/kg. Optionally, in some methods the dosage is between about 0.5 to about 1.5 mg/kg. Optionally, in some methods the dosage is administered every 13 weeks. Optionally, in some methods the antibody is administered intravenously or subcutaneously. Optionally, the agent is an antibody that binds within residues 1-5 of Aβ. Optionally, the antibody is a humanized, human, or chimeric antibody. Optionally, the humanized antibody is 3D6. Optionally, the 3D6 humanized antibody is bapineuzumab. Optionally, the humanized antibody is 12A11.

The invention provides methods of treating Alzheimer's disease. The methods comprise administering an antibody that is specific for the N-terminus of Aβ at a dose that reduces or inhibits development of vascular amyloidogenic pathology, minimizes microhemorrhage, and or reduces or inhibits development of Aβ plaques. Optionally, in some methods the antibody binds within residues 1-5 of Aβ. Optionally, the antibody is a humanized, human, or chimeric antibody. Optionally, the humanized antibody is 3D6. Optionally, the 3D6 humanized antibody is bapineuzumab. Optionally, the humanized antibody is 12A11.

The invention provides methods of treating Alzheimer's disease that comprise administering an antibody that is specific for the N-terminus of Aβ at a dose that reduces or inhibits development of vascular amyloidogenic pathology, minimizes microhemorrhage, and or reduces or inhibits development of neuritic pathology. Optionally, in some methods the antibody binds within residues 1-5 of Aβ. Optionally, the antibody is a humanized, human, or chimeric antibody. Optionally, the humanized antibody is 3D6. Optionally, the 3D6 humanized antibody is bapineuzumab. Optionally, the humanized antibody is 12A11.

The invention provides methods for treating Alzheimer's disease that comprise administering an antibody that is specific for the N-terminus of Aβ at a dose that reduces or inhibits vascular amyloidogenic pathology, minimizes microhemorrhage, and or improves patient's cognitive function. Optionally, in some methods the antibody binds within residues 1-5 of Aβ. Optionally, the antibody is a humanized, human, or chimeric antibody. Optionally, the humanized antibody is 3D6. Optionally, the 3D6 humanized antibody is bapineuzumab. Optionally, the humanized antibody is 12A11.

Optionally, some methods of treating Alzheimer's disease the reduction or inhibition of vascular amyloidogenic pathology is a prevention of accumulation of vascular Aβ or clearance of vascular Aβ.

The invention further provides diagnostic kits suitable for use in the above methods. Such a kit comprises an antibody that specifically binds to an epitope with residues 1-10 of Aβ. Some kits bear a label describing use of the antibody for in vivo diagnosis or monitoring of Alzheimer's disease The invention further provides kits for treatment of CAA suitable for use in the above methods. Such a kit comprises a glass vial containing a formulation. Some kits of the invention comprise a glass vial containing a formulation comprising about 0.5 to 3 mg/kg of a humanized anti-Aβ antibody. Some kits of the invention comprise a glass vial containing a formulation comprising: i. between about 10 mg to about 250 mg of a humanized anti-Aβ antibody, ii. about 4% mannitol or about 150 mM NaCl, iii. about 5 mM to about 10 mM histidine, and iv. about 10 mM methionine. Some kits contain instructions to monitor a patient to whom the formulation is administered for CAA. Optionally, the instructions comprise: i. monitoring the patient for cerebral microhemorrhage by MRI, or ii. monitoring the patient for vascular amyloid removal by PET scan.

The invention further provides kits for treatment of Alzheimer's disease suitable for use in the above methods. Such a comprises a glass vial containing a formulation comprising: i. between about 10 mg to about 250 mg of a humanized anti-Aβ antibody, ii. about 4% mannitol or about 150 mM NaCl, iii. about 5 mM to about 10 mM histidine, and iv. about 10 mM methionine. Some kits contain instructions to monitor a patient to whom the formulation is administered for Alzheimer's disease. Optionally, the instructions comprise: i. monitoring the patient for cerebral microhemorrhage by MRI, or ii. monitoring the patient for vascular amyloid removal by PET scan.

The invention further provides kits for treatment of CAA and Alzheimer's disease suitable for use in the above methods. Such a kit comprises a glass vial containing a formulation comprising: i. between about 10 mg to about 250 mg of a humanized anti-Aβ antibody, ii. about 4% mannitol or about 150 mM NaCl, iii. about 5 mM to about 10 mM histidine, and iv. about 10 mM methionine. Some kits contain instructions to monitor a patient to whom the formulation is administered for CAA and Alzheimer's disease. Optionally, the instructions comprise: i. monitoring the patient for cerebral microhemorrhage by MRI, or ii. monitoring the patient for vascular amyloid removal by PET scan.

Optionally, the antibody is administered at a dose of between about 0.05 to about 0.5 mg/kg. Optionally, the antibody is administered at a dose of between about 1 to about 40 mg and a frequency of between weekly and monthly. Optionally, the antibody is administered at a dose of between about 5 to about 25 mg and a frequency of between weekly and monthly. Optionally, the antibody is administered at a dose of between about 2.5 to about 15 mg and a frequency of between weekly and monthly.

Optionally, the antibody is administered at a dose of between about 1 to about 12 mg weekly to biweekly. Optionally, the antibody is administered at a dose of between about 2.5 to about 10 mg weekly to biweekly. Optionally, the antibody is administered at a dose of between about 2.5 to about 5 mg weekly. Optionally, the antibody is administered at a dose of between about 4 to about 5 mg weekly. Optionally, the antibody is administered at a dose of between about 7 to about 10 mg biweekly.

The invention provides methods for restoring cerebral vascular phenotype in a patient suffering from vascular Aβ deposits. The methods comprise administering an antibody that is specific for Aβ. Optionally, the antibody is specific for the N-terminus of Aβ. Optionally, the antibody binds within residues 1-5 of Aβ. Optionally, the antibody is a humanized, human, or chimeric antibody. Optionally, the antibody is humanized 3D6 or humanized 12A11. Optionally, the humanized 3D6 antibody is bapineuzumab.

Some methods of the invention further comprise comprising monitoring cerebral vascular phenotype of the patient. In some methods monitoring comprises quantification of vascular elements along the vessel perimeter. Optionally, the monitoring comprises quantification of vascular elements selected from the group consisting of vessel layer thickness, vessel size, luminal perimeter, intensity, and the relative position of vessel elements.

The invention provides methods of restoring cerebral vascular meningeal vessel phenotype from structural damage from amyloid induced structural changes. The methods comprise monitoring for amyloid induced structural changes involving degeneration and hyperplasia/hypertrophy of smooth muscle cells and extracellular matrix in the vessel walls, and administering an antibody that is specific for Aβ. The methods comprise administering an antibody that is specific for Aβ. Optionally, the antibody is specific for the N-terminus of Aβ. Optionally, the antibody binds within residues 1-5 of Aβ. Optionally, the antibody is a humanized, human, or chimeric antibody. Optionally, the antibody is humanized 3D6 or humanized 12A11. Optionally, the humanized 3D6 antibody is bapineuzumab.

BRIEF DESCRIPTION OF THE DRAWINGS

FIG. 7a shows the regions where a vessel is sectioned. FIG. 7b shows a vessel plot for wild type mice. FIG. 7c shows a vessel plot for untreated PDAP mice. FIG. 7d shows smooth muscle thickness (μm) for vessel sements of untreated PDAPP mice, treated PDAPP mice, and wild type mice.

DEFINITIONS

Figure 1:
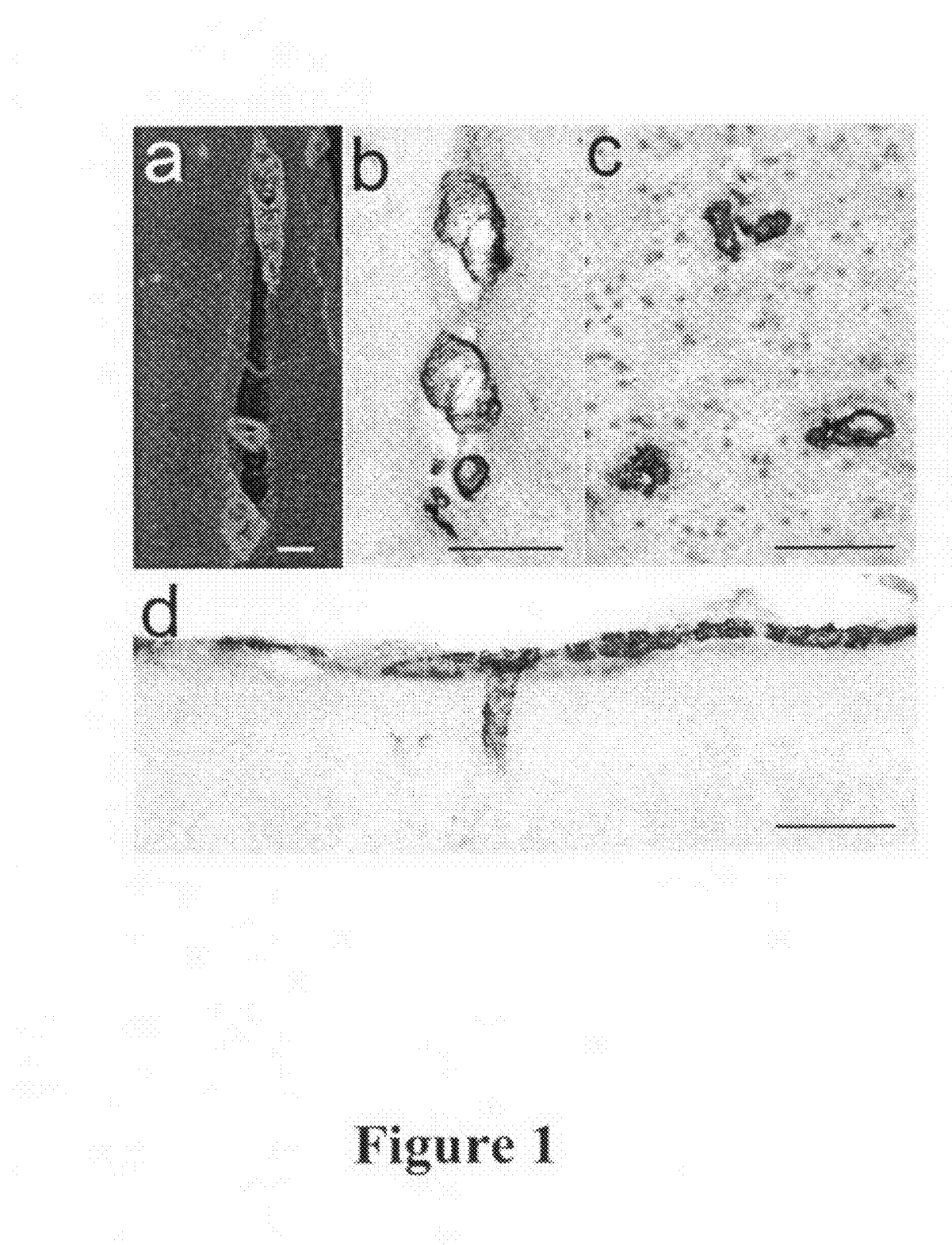
FIG. 1a shows thioflavin S staining.
FIG. 1b shows 3D6 immunolabeling of Aβ in brain midline vessels of 18-month-old PDAPP mice.
FIG. 1c shows human AD tissue.
FIG. 1d shows leptomeningeal and superficial parenchymal vessels in the PDAPP mouse with VAβ immunolabeled by 3D6. Scale bars=100 μm.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (NCBI) website. Typically, default program parameters can be used to perform the sequence comparison, although customized parameters can also be used. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89, 10915 (1989)).

For purposes of classifying amino acids substitutions as conservative or non-conservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminants. This means that an agent is typically at least about 50% w/w (weight/weight) purity, as well as being substantially free from interfering proteins and contaminants. Sometimes the agents are at least about 80% w/w and, more preferably at least about 90 or about 95% w/w purity. However, using conventional protein purification techniques, homogeneous peptides of at least about 99% w/w can be obtained.

The phrase that a molecule "specifically binds" or "specifically immunoreactive" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$ $M^{-1}$, or $10^{10}$ $M^{-1}$. Affinities greater than $10^8$ $M^{-1}$ are preferred.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

$APP^{695}$, $APP^{751}$, and $APP^{770}$ refer, respectively, to the 695, 751, and 770 amino acid residue long polypeptides encoded by the human APP gene. See Kang et al., *Nature* 325, 773 (1987); Ponte et al., *Nature* 331, 525 (1988); and Kitaguchi et al., *Nature* 331, 530 (1988). Amino acids within the human amyloid precursor protein (APP) are assigned numbers according to the sequence of the APP770 isoform.

Terms such as Aβ39, Aβ40, Aβ41, Aβ42 and Aβ43 refer to an Aβ peptide containing amino acid residues 1-39, 1-40, 1-41, 1-42 and 1-43. The sequences of these peptides and their relationship to the APP precursor are illustrated by FIG. 1 of Hardy et al., TINS 20, 155-158 (1997). For example, Aβ42 has the sequence:

DAEFRHDSGYEVHHQKLVFFAEDVGSNK-GAIIGLMVGGVVIAT (SEQ ID NO:28)

Aβ41, Aβ40 and Aβ39 differ from Aβ42 by the omission of Ala, Ala-Ile, and Ala-Ile-Val respectively from the C-terminal end. Aβ43 differs from Aβ42 by the presence of a Thr residue at the C-terminus.

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110-19 (1994)), by antigen-dependent killing (cytotoxic T lymphocyte assay, Tigges et al., *J. Immunol.* 156, 3901-3910) or by cytokine secretion.

The term "immunological" or "immune" response is the development of a humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays (see Burke, supra; Tigges, supra). The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "all-D" refers to peptides having ≧75%, ≧80%, ≧85%, ≧90%, ≧95%, or 100% D-configuration amino acids.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

Some variation of disclosed ranges and is permissible as for example due to errors in measurement. Such variation is designated by the term "about" in reference to ranges or doses.

The term "patient" includes human and other mammalian subjects that receive either prophylactic or therapeutic treatment.

Competition between antibodies is determined by an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, *Antibodies, A Laboratory Manual*, Cold Spring Harbor Press (1988)); solid phase direct label RIA using 1-125 label (see Morel et al., *Molec. Immunol.* 25(1):7-15 (1988)); solid phase direct biotin-avidin EIA (Cheung et al., *Virology* 176: 546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

The term "symptom" or "clinical symptom" refers to a subjective evidence of a disease, such as altered gait, as perceived by the patient. A "sign" refers to objective evidence of a disease as observed by a physician.

Compositions or methods "comprising" one or more recited elements may include other elements not specifically recited.

DETAILED DESCRIPTION OF THE INVENTION

I. General

The invention provides methods of effecting prophylaxis and treatment of cerebral amyloid angiopathy (CAA), a disease characterized by presence of vascular deposits of Aβ peptide. These vascular deposits are distinct from the parenchymal deposits that are the hallmark of Alzheimer's disease. Most Alzheimer's patients are affected by at least mild CAA. However, CAA can also occur independent of symptoms and/or characteristic pathology of Alzheimer's disease. CAA is also associated with symptoms not generally associated with Alzheimer's disease, such as strokes. The invention provides methods of effecting prophylaxis or treating CAA whether it occurs alone or concurrently with Alzheimer's disease. In patients having concurrent Alzheimer's disease and CAA, the methods can treat both diseases simultaneously. In patients having neither disease, the methods can effect prophylaxis against both diseases. In patients having CAA but not Alzheimer's disease, the methods can treat CAA and effect prophylaxis of Alzheimer's disease. The invention provides methods to restore cerebral vascular phenotype in patient suffering from vascular Aβ deposits. The invention provides methods of monitoring cerebral vascular phenotype. The invention provides methods of restoring cerebral vascular meningeal vessel phenotype from structural damage from amyloid induced structural changes.

The methods involve active or passive immunotherapy. In passive immunotherapy, an antibody binding to an epitope within residues 1-10 of Aβ is administered. In active immunotherapy, an agent is administered, such as an Aβ fragment that can induce such an antibody. In other methods of passive immunotherapy, an antibody that is specific for Aβ is administered. In other methods of active immunotherapy, an agent is administered, such as an Aβ fragment that can induce such an antibody. Although an understanding of mechanism is not essential for practice of the invention, it is believed that the antibodies bind to vascular deposits of Aβ and thereby promotes clearing of the deposits.

II. Agents

The present methods employ an agent that either is an antibody to the N-terminus of Aβ (passive administration) or is capable of inducing such an antibody on administration to a patient. Such agents have been previously described in the scientific and patent literature in connection with immunotherapy of Alzheimer's disease (see WO 98/25386 and WO 00/72880).

A. Active Immunotherapy

Aβ, also known as β-amyloid peptide, or A4 peptide (see U.S. Pat. No. 4,666,829; Glenner & Wong, *Biochem. Biophys. Res. Commun.* 120, 1131 (1984)), is a peptide of 39-43 amino acids, which is the principal component of characteristic plaques of Alzheimer's disease. Aβ is generated by processing of a larger protein APP by two enzymes, termed β and γ secretases (see Hardy, *TINS* 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD by interacting with the cleavage reactions by which Aβ is formed so as to increase the amount of the 42/43 amino acid form of Aβ generated.

Aβ has the unusual property that it can fix and activate both classic and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 fold increase in activation of these cells. This mechanism causes Aβ to generate an immune response in excess of that of other antigens.

Preferred agents for active administration are fragments beginning at residue 1 of Aβ and ending between one of residues 5-10. Such fragments when linked to an appropriate carrier are capable or inducing antibodies that specifically bind to the N-terminus of Aβ. Such fragments are lacking naturally occurring self T-cell epitopes that have been associated with undesired side effects in clinical trials of intact Aβ. Preferred immunogenic fragments include Aβ1-5, 1-6, and 1-7, 1-10, 3-7, 1-3, and 1-4. The designation Aβ1-5 for example, indicates a fragment including residues 1-5 of Aβ and lacking other residues of Aβ.

Aβ-derived diffusible ligands (ADDLs), ADDL-surrogates, ADDL-binding molecules can also be used for active immunotherapy. See e.g., WO 2004/031400, incorporated by reference in its entirety for all purposes.

Optionally, fragments of Aβ are conjugated to carrier to help induce antibodies to the fragment. Some agents for inducing an immune response contain the appropriate epitope for inducing an immune response against amyloid but are too small to be immunogenic. In this situation, a peptide immunogen can be linked to a suitable carrier molecule to form a conjugate which helps elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (for example, CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine (Pam$_3$Cys), mannan (a manose polymer), or glucan (a beta 1→2 polymer)), cytokines (e.g., IL-1, IL-1 alpha and beta peptides, IL-2, gamma-INF, IL-10, GM-CSF), and chemokines (e.g., MIP1alpha and beta, and RANTES). Immunogenic agents can also be linked to peptides that enhance transport across tissues, as described in O'Mahony, WO 97/17613 and WO 97/17614. Immunogens may be linked to the carries with or with out spacer amino acids (e.g., gly-gly).

Some conjugates can be formed by linking agents of the invention to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), hepatitis B surface antigen, pertussis, toxoid, measles virus F protein, *Chlamydia trachomitis* major outer membrane protein, diphtheria toxoid, *Plasmodium falciparum* circumsporozite T, *Plasmodium falciparum* CS antigen, *Schistosoma mansoni* triose phosphate isomersae, *Escherichia coli* TraT, and influenza virus hemagluttinin (HA). The immunogenic peptides of the invention can also be conjugated to the T-cell epitopes described in Sinigaglia F. et al., *Nature*, 336: 778-780 (1988); Chicz R. M. et al., *J. Exp. Med.*, 178:27-47 (1993); Hammer J. et al., *Cell* 74:197-203 (1993); Falk K. et al., *Immunogenetics*, 39:230-242 (1994); WO 98/23635; and, Southwood S. et al. *J. Immunology*, 160:3363-3373 (1998)

(each of which is incorporated herein by reference for all purposes). Further examples include:

| | |
|---|---|
| Influenza hemaglutinin: | HA$_{307-319}$ |
| Malaria CS: T3 epitope | EKKIAKMEKASSVFNV (SEQ ID NO: 29) |
| Hepatitis B surface antigen: HBsAg$_{19-28}$ | FFLLTRILTI (SEQ ID NO: 30) |
| Heat shock protein 65: hsp65$_{153-171}$ | DQSIGDLIAEAMDKVGNEG (SEQ ID NO: 31) |
| Bacille Calmette-Guerin: | QVHFQPLPPAVVKL (SEQ ID NO: 32) |
| Tetanus toxoid: TT$_{830-844}$ | QYIKANSKFIGITEL (SEQ ID NO: 33) |
| Tetanus toxoid: TT$_{947-967}$ | FNNFTVSFWLRVPKVSASHLE (SEQ ID NO: 34) |
| HIV gp120 T1: | KQIINMWQEVGKAMYA (SEQ ID NO: 35) |

HIV gp120 T1: KQIINMWQEVGKAMYA (SEQ ID NO:35)

Some examples of conjugates include:

AN90549 (Aβ1-7-Tetanus toxoid 830-844 in a MAP4 configuration):

(SEQ ID NO: 36)
DAEFRHD-QYIKANSKFIGITEL

AN90550 (Aβ 1-7-Tetanus toxoid 947-967 in a MAP4 configuration):

(SEQ ID NO: 37)
DAEFRHD-FNNFTVSFWLRVPKVSASHLE

AN90542 (Aβ 1-7-Tetanus toxoid 830-844+947-967 in a linear configuration):

(SEQ ID NO: 38)
DAEFRHD-QYIKANSKFIGITELFNNFTVSFWLRVPKVSASHLE

PADRE peptide (all in linear configurations), wherein X is preferably cyclohexylalanine, tyrosine or phenylalanine, with cyclohexylalanine being most preferred:

AN90562 (PADRE-Aβ1-7):

(SEQ ID NO: 39)
AKXVAAWTLAAA-DAEFRHD

AN90543 (3 PADRE-Aβ1-7):

(SEQ ID NO: 40)
DAEFRHD-DAEFRHD-DAEFRHD-AKXVAAWTLKAAA

Other examples of fusion proteins (immunogenic epitope of Aβ bolded) include:

AKXVAAWTLKAAA-DAEFRHD-DAEFRHD-DAEFRHD
(SEQ ID NO: 41)

DAEFRHD-AKXVAAWTLKAAA
(SEQ ID NO: 42)

DAEFRHD-ISQAVHAAHAEINEAGR
(SEQ ID NO: 43)

FRHDSGY-ISQAVHAAHAEINEAGR
(SEQ ID NO: 44)

EFRHDSG-ISQAVHAAHAEINEAGR
(SEQ ID NO: 45)

PKYVKQNTLKLAT-DAEFRHD-DAEFRHD-DAEFRHD
(SEQ ID NO: 46)

DAEFRHD-PKYVKQNTLKLAT-DAEFRHD
(SEQ ID NO: 47)

DAEFRHD-DAEFRHD-DAEFRHD-PKYVKQNTLKLAT
(SEQ ID NO: 48)

DAEFRHD-DAEFRHD-PKYVKQNTLKLAT
(SEQ ID NO: 49)

DAEFRHD-PKYVKQNTLKLAT-EKKIAKMEKASSVFNV-QYIKANSKFIGITEL-FNNFTVSFWLRVPKVSASHLE-DAEFRHD
(SEQ ID NO: 50)

DAEFRHD-DAEFRHD-DAEFRHD-QYIKANSKFIGITELNNFTVSFWLRVPKVSASHLE
(SEQ ID NO: 51)

DAEFRHD-QYIKANSKFIGITELCFNNFTVSFWLRVPKVSASHLE
(SEQ ID NO: 52)

DAEFRHD-QYIKANSKFIGITELCFNNFTVSFWLRVPKVSASHLE-DAEFRHD (SEQ ID NO: 53)

DAEFRHD-QYIKANSKFIGITEL (SEQ ID NO: 35) on a 2 branched resin.

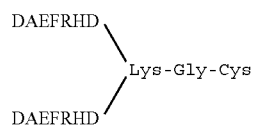

Fragments of Aβ such as Aβ1-6 are conjugated to carriers, such as virus-like-particles (VLPs) and subunits of VLPs, to help induce antibodies to the fragment. See e.g., WO 2004/016282 and US 20040141984, each of which is incorporated by reference in its entirety for all purposes.

B. Passive Immunotherapy

Passive immunotherapy is effected using an antibody that is specific for the N-terminus Aβ. An "N-terminal epitope", is an epitope or antigenic determinant located within or including the N-terminus of the Aβ peptide. Exemplary N-terminal epitopes include residues within amino acids 1-10 or 1-12 of Aβ, preferably from residues 1-3, 1-4, 1-5, 1-6, 1-7, 2-6, 2-7, 3-6, or 3-7 of Aβ. Other exemplary N-terminal epitopes start at residues 1-3 and end at residues 7-11 of Aβ. Additional exemplary N-terminal epitopes include residues 2-4, 2-5, 2-6, 2-7 or 2-8 of Aβ, residues 3-5, 3-6, 3-7, 3-8 or 3-9 of Aβ, or residues 4-7, 4-8, 4-9 or 4-10 of Aβ.

When an antibody is said to bind to an epitope within specified residues, such as Aβ3-7, what is meant is that the antibody specifically binds to a polypeptide containing the specified residues (i.e., Aβ3-7 in this an example). Such an antibody does not necessarily contact every residue within Aβ3-7. Nor does every single amino acid substitution or deletion within Aβ3-7 necessarily significantly affect binding affinity. In various embodiments, an Aβ antibody is end-specific. As used herein, the term "end-specific" refers to an antibody that specifically binds to the N-terminal or C-terminal residues of an Aβ peptide but that does not recognize the same residues when present in a longer Aβ species comprising the residues or in APP. Preferred antibodies have human IgG1 isotype.

Preferred anti Aβ antibodies for passive immunotherapy include a humanized anti-Aβ antibody, for example, a humanized 3D6 antibody, a humanized 12B4 antibody, or a humanized 12A11 antibody.

Antibodies for passive immunotherapy may be provided by a variety of techniques including those described in US 20040038304, US 20070020685, US 20060257396, US 20060160184, US 20060134098, US 20050255552, US 20050008625, US 20040132066, US 20040038317, US 20030198971, and US 20030157579 all of which are incorporated by reference in their entirety herein for all purposes.

Antibodies i. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology*, Ch. 7 (W. Paul, ed., Raven Press, N.Y., 2nd ed. 1989), incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991); Chothia & Lesk, *J. Mol. Biol.* 196:901-917 (1987); or Chothia et al., *Nature* 342:878-883 (1989).

ii. Production of Nonhuman Antibodies

The production of non-human monoclonal antibodies, e.g., murine, guinea pig, primate, rabbit or rat, can be accomplished by, for example, immunizing the animal with Aβ. A longer polypeptide comprising Aβ or an immunogenic fragment of Aβ or anti-idiotypic antibodies to an antibody to Aβ can also be used. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein, as described below. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to Aβ. Optionally, antibodies are further screened for binding to a specific region of Aβ. The latter screening can be accomplished by determining binding of an antibody to a collection of deletion mutants of an Aβ peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to Aβ. If the test and reference antibodies compete, then they bind to the same epitope or epitopes sufficiently proximal that binding of one antibody interferes with binding of the other. The preferred isotype for such antibodies is mouse isotype IgG2a or equivalent isotype in other species. Mouse isotype IgG2a is the equivalent of human isotype IgG1.

iii. Chimeric and Humanized Antibodies

Chimeric and humanized antibodies have the same or similar binding specificity and affinity as a mouse or other non-human antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., *Proc. Natl. Acad. Sci. USA* 86:10029-10033 (1989), WO 90/07861, U.S. Pat. No. 5,693,762, U.S. Pat. No. 5,693,761, U.S. Pat. No. 5,585,089, U.S. Pat. No. 5,530,101, and Winter, U.S. Pat. No. 5,225,539 (each of which is incorporated by reference in its entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:
(1) noncovalently binds antigen directly,
(2) is adjacent to a CDR region,
(3) otherwise interacts with a CDR region (e.g. is within about 6 A of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

iv. Human Antibodies

Human antibodies against Aβ are provided by a variety of techniques described below. Some human antibodies are selected by competitive binding experiments, or otherwise, to have the same epitope specificity as a particular mouse antibody, such as one of the mouse monoclonals described in Example XI. Human antibodies can also be screened for a particular epitope specificity by using only a fragment of Aβ as the immunogen, and/or by screening antibodies against a collection of deletion mutants of Aβ. Human antibodies preferably have isotype specificity human IgG1.

(1) Trioma Methodology

The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells-two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with Aβ, a fragment thereof, larger polypeptide containing Aβ or fragment, or an anti-idiotypic antibody to an antibody to Aβ. In some methods, B cells are isolated from the same patient who is ultimately to be administered antibody therapy. For in vitro immunization, B-lymphocytes are typically exposed to antigen for a period of 7-14 days in a media such as RPMI-1640 (see Engleman, supra) supplemented with 10% human plasma.

The immunized B-lymphocytes are fused to a xenogeneic hybrid cell such as SPAZ-4 by well-known methods. For example, the cells are treated with 40-50% polyethylene glycol of MW 1000-4000, at about 37 degrees C., for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

(2) Transgenic Non-Human Mammals

Human antibodies against Aβ can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/1222, U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741 (each of which is incorporated by reference in its entirety for all purposes). Transgenic mice are particularly suitable. Anti-Aβ antibodies are obtained by immunizing a transgenic nonhuman mammal, such as described by Lonberg or Kucherlapati, supra, with Aβ or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using Aβ or other amyloid peptide as an affinity reagent.

(3) Phage Display Methods

A further approach for obtaining human anti-Aβ antibodies is to screen a DNA library from human B cells according to the general protocol outlined by Huse et al., Science 246: 1275-1281 (1989). As described for trioma methodology, such B cells can be obtained from a human immunized with Aβ fragments, longer polypeptides containing Aβ or fragments, or anti-idiotypic antibodies. Optionally, such B cells are obtained from a patient who is ultimately to receive antibody treatment. Antibodies binding to Aβ or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an Aβ peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for Aβ (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for Aβ are selected. These phage display the variable regions of completely human anti-Aβ antibodies. These antibodies usually have the same or similar epitope specificity as the murine starting material.

(4) Nanobody Methods

Antibodies against Aβ can also be produced via the Nanobody™ methods (Ablynx N.V.). Nanobodies are antibody-derived therapeutic proteins that contain the properties of naturally-occurring heavy chain antibodies. Nanobodies can function as a single, relatively small, functional antigen-binding structural unit, domain or protein. The Nanobody™ technology was originally developed following the discovery that camelidae (camels and llamas) possess fully functional antibodies that lack light chains. These heavy-chain antibodies contain a single variable domain (VHH) and two constant domains (CH2 and CH3). VHH is used to distinguish them from the heavy chain variable domains that are present in conventional 4-chain antibodies (which are referred to as "VH domains"). The cloned and isolated VHH domain is a stable polypeptide harboring the full antigen-binding capacity of the original heavy-chain antibody. VHH domains and nanobodies can also be engineered into multivalent and multispecific formats. Nanobodies with an amino acid sequence that corresponds to the amino acid sequence of a naturally occurring VHH domain can be humanized, i.e., by replacing one or more amino acid residues in the amino acid sequence of the naturally occurring VHH sequence (and in particular in the framework sequences) by one or more of the amino acid residues that occur at the corresponding position(s) in a VH domain from a conventional 4-chain antibody from a human being. For details, see e.g., US 20050130266, US 20040253638, WO/2006/040153, US 20050214857, WO/2006/079372, or WO/2006/122825, each of which is incorporated herein by reference for all purposes.

v. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')$_2$, and Fv, or as single chain antibodies in which heavy and light chain variable domains are linked through a spacer.

vi. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high-level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast, are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, *From Genes to Clones*, (VCH Publishers, NY, 1987). A number of suitable host cell lines capable of secreting intact heterologous proteins have been developed in the art, and include CHO cell lines, various COS cell lines, HeLa cells, L cells, human embryonic kidney cell, and myeloma cell lines. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. No. 5,741,957, U.S. Pat. No. 5,304,489, U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

3D6 or a chimeric or humanized form thereof is a preferred antibody (see U.S. Patent Publication No. 20030165496A1, U.S. Patent Publication No. 20040087777A1, International Patent Publication No. WO 02/46237A3 and International Patent Publication No. WO 04/080419A2). Description of 3D6 can also be found, for example, in International Patent Publication No. WO 02/088306A2 and International Patent Publication No. WO02/088307A2. Additional 3D6 antibodies are described in U.S. patent application Ser. No. 11/303,478 and International Application No. PCT/US05/45614. 3D6 is a monoclonal antibody (mAb) that specifically binds to an N-terminal epitope located in the human β-amyloid peptide, specifically, residues 1-5. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and has deposit number PTA-5130.

Bapineuzumab (International Non-Proprietary Name designated by the World Health Organization) means a humanized 3D6 antibody comprising a light chain having a mature variable region having the amino acid sequence designated SEQ ID NO: 1 and a heavy chain having a mature variable region having the amino acid sequence designated SEQ ID NO: 2 is shown below. (The heavy and light chain constant regions of the antibody designated bapineuzumab by WHO are human IgG1 and human kappa, respectively.)

```
Humanized 3D6 Light Chain Variable Region
Asp Val Val Met Thr Gln Ser Pro Leu Ser Leu Pro Val Thr Pro Gly Glu Pro Ala Ser Ile Ser    (SEQ ID NO: 1)

Cys Lys Ser Ser Gln Ser Leu Leu Asp Ser Asp Gly Lys Thr Tyr Leu Asn Trp Leu Leu Gln

Lys Pro Gly Gln Ser Pro Gln Arg Leu Ile Tyr Leu Val Ser Lys Leu Asp Ser Gly Val Pro Asp

Arg Phe Ser Gly Ser Gly Ser Gly Thr Asp Phe Thr Leu Lys Ile Ser Arg Val Glu Ala Glu Asp

Val Gly Val Tyr Tyr Cys Trp Gln Gly Thr His Phe Pro Arg Thr Phe Gly Gln Gly Thr Lys

Val Glu Ile Lys

Humanized 3D6 Heavy Chain Variable Region
Glu Val Gln Leu Leu Glu Ser Gly Gly Gly Leu Val Gln Pro Gly Gly Ser Leu Arg Leu Ser    (SEQ ID NO: 2)

Cys Ala Ala Ser Gly Phe Thr Phe Ser Asn Tyr Gly Met Ser Trp Val Arg Gln Ala Pro Gly

Lys Gly Leu Glu Trp Val Ala Ser Ile Arg Ser Gly Gly Gly Arg Thr Tyr Tyr Ser Asp Asn Val

Lys Gly Arg Phe Thr Ile Ser Arg Asp Asn Ser Lys Asn Thr Leu Tyr Leu Gln Met Asn Ser

Leu Arg Ala Glu Asp Thr Ala Val Tyr Tyr Cys Val Arg Tyr Asp His Tyr Ser Gly Ser Ser

Asp Tyr Trp Gly Gln Gly Thr Leu Val Thr Val Ser Ser
```

Bapineuzumab is known as AAB-001.

A second version of humanized 3D6 antibody comprising a light chain having a mature variable region having the amino acid sequence designated SEQ ID NO: 3 and a heavy chain having a mature variable region having the amino acid sequence designated SEQ ID NO: 4 is shown below.

```
Humanized 3D6 Light Chain Variable Region
Tyr Val Val Met Thr Gln Ser Pro Leu Ser Leu Pro Val Thr Pro Gly Glu Pro Ala Ser Ile Ser    (SEQ ID NO: 3)

Cys Lys Ser Ser Gln Ser Leu Leu Asp Ser Asp Gly Lys Thr Tyr Leu Asn Trp Leu Leu Gln

Lys Pro Gly Gln Ser Pro Gln Arg Leu Ile Tyr Leu Val Ser Lys Leu Asp Ser Gly Val Pro Asp

Arg Phe Ser Gly Ser Gly Ser Gly Thr Asp Phe Thr Leu Lys Ile Ser Arg Val Glu Ala Glu Asp

Val Gly Val Tyr Tyr Cys Trp Gln Gly Thr His Phe Pro Arg Thr Phe Gly Gln Gly Thr Lys

Val Glu Ile Lys
```

```
Humanized 3D6 Heavy Chain Variable Region
Glu Val Gln Leu Leu Glu Ser Gly Gly Gly Leu Val Gln Pro Gly Gly Ser Leu Arg Leu Ser      (SEQ ID NO: 4)

Cys Ala Ala Ser Gly Phe Thr Phe Ser Asn Tyr Gly Met Ser Trp Val Arg Gln Ala Pro Gly

Lys Gly Leu Glu Trp Val Ala Ser Ile Arg Ser Gly Gly Gly Arg Thr Tyr Tyr Ser Asp Asn Val

Lys Gly Arg Phe Thr Ile Ser Arg Asp Asn Ala Lys Asn Ser Leu Tyr Leu Gln Met Asn Ser

Leu Arg Ala Glu Asp Thr Ala Leu Tyr Tyr Cys Val Arg Tyr Asp His Tyr Ser Gly Ser Ser

Asp Tyr Trp Gly Gln Gly Thr Leu Val Thr Val Ser Ser
```

A third version of humanized 3D6 antibody comprising a light chain having the amino acid sequence designated SEQ ID NO: 5 and a heavy chain having the amino acid sequence designated SEQ ID NO: 6 is described in US 2005/0090649 A1 published on Apr. 28, 2005, which is incorporated herein by reference for all purposes.

```
Humanized 3D6 Light Chain
Asp Val Val Met Thr Gln Ser Pro Leu Ser Leu Pro Val Thr Leu Gly Gln Pro Ala Ser Ile Ser      (SEQ ID NO: 5)

Cys Lys Ser Ser Gln Ser Leu Leu Asp Ser Asp Gly Lys Thr Tyr Leu Asn Trp Leu Gln Gln

Arg Pro Gly Gln Ser Pro Arg Arg Leu Ile Tyr Leu Val Ser Lys Leu Asp Ser Gly Val Pro Asp

Arg Phe Ser Gly Ser Gly Ser Gly Thr Asp Phe Thr Leu Lys Ile Ser Arg Val Glu Ala Glu Asp

Val Gly Val Tyr Tyr Cys Trp Gln Gly Thr His Phe Pro Arg Thr Phe Gly Gly Gly Thr Lys

Val Glu Ile Lys Arg Thr Val Ala Ala Pro Ser Val Phe Ile Phe Pro Pro Ser Asp Glu Gln Leu

Lys Ser Gly Thr Ala Ser Val Val Cys Leu Leu Asn Asn Phe Tyr Pro Arg Glu Ala Lys Val

Gln Trp Lys Val Asp Asn Ala Leu Gln Ser Gly Asn Ser Gln Glu Ser Val Thr Glu Gln Asp

Ser Lys Asp Ser Thr Tyr Ser Leu Ser Ser Thr Leu Thr Leu Ser Lys Ala Asp Tyr Glu Lys His

Lys Val Tyr Ala Cys Glu Val Thr His Gln Gly Leu Ser Ser Pro Val Thr Lys Ser Phe Asn Arg

Gly Glu Cys

Humanized 3D6 Heavy Chain
Glu Val Gln Leu Val Glu Ser Gly Gly Gly Leu Val Gln Pro Gly Gly Ser Leu Arg Leu Ser      (SEQ ID NO: 6)

Cys Ala Gly Ser Gly Phe Thr Phe Ser Asn Tyr Gly Met Ser Trp Val Arg Gln Ala Pro Gly

Lys Gly Leu Glu Trp Val Ala Ser Ile Arg Ser Gly Gly Gly Arg Thr Tyr Tyr Ser Asp Asn Val

Lys Gly Arg Phe Thr Ile Ser Arg Glu Asn Ala Lys Asn Ser Leu Tyr Leu Gln Met Asn Ser

Leu Arg Ala Glu Asp Thr Ala Val Tyr Tyr Cys Val Arg Tyr Asp His Tyr Ser Gly Ser Ser

Asp Tyr Trp Gly Gln Gly Thr Leu Val Thr Val Ser Ser Ala Ser Thr Lys Gly Pro Ser Val Phe

Pro Leu Ala Pro Ser Ser Lys Ser Thr Ser Gly Gly Thr Ala Ala Leu Gly Cys Leu Val Lys Asp

Tyr Phe Pro Glu Pro Val Thr Val Ser Trp Asn Ser Gly Ala Leu Thr Ser Gly Val His Thr Phe

Pro Ala Val Leu Gln Ser Ser Gly Leu Tyr Ser Leu Ser Ser Val Val Thr Val Pro Ser Ser Ser

Leu Gly Thr Gln Thr Tyr Ile Cys Asn Val Asn His Lys Pro Ser Asn Thr Lys Val Asp Lys

Lys Val Glu Pro Lys Ser Cys Asp Lys Thr His Thr Cys Pro Pro Cys Pro Ala Pro Glu Leu

Leu Gly Gly Pro Ser Val Phe Leu Phe Pro Pro Lys Pro Lys Asp Thr Leu Met Ile Ser Arg Thr

Pro Glu Val Thr Cys Val Val Val Asp Val Ser His Glu Asp Pro Glu Val Lys Phe Asn Trp

Tyr Val Asp Gly Val Glu Val His Asn Ala Lys Thr Lys Pro Arg Glu Glu Gln Tyr Asn Ser

Thr Tyr Arg Val Val Ser Val Leu Thr Val Leu His Gln Asp Trp Leu Asn Gly Lys Glu Tyr

Lys Cys Lys Val Ser Asn Lys Ala Leu Pro Ala Pro Ile Glu Lys Thr Ile Ser Lys Ala Lys Gly

Gln Pro Arg Glu Pro Gln Val Tyr Thr Leu Pro Pro Ser Arg Asp Glu Leu Thr Lys Asn Gln

Val Ser Leu Thr Cys Leu Val Lys Gly Phe Tyr Pro Ser Asp Ile Ala Val Glu Trp GluSer Asn

Gly Gln Pro Glu Asn Asn Tyr Lys Thr Thr Pro Pro Val Leu Asp Ser Asp Gly Ser Phe Phe
```

-continued

```
Leu Tyr Ser Lys Leu Thr Val Asp Lys Ser Arg Trp Gln Gln Gly Asn Val Phe Ser Cys Ser

Val Met His Glu Ala Leu His Asn His Tyr Thr Gln Lys Ser Leu Ser Leu Ser Pro Gly Lys
```

12A11 or a chimeric or humanized or nanobody form thereof is a preferred antibody. The 12A11 antibody or a variant thereof, is described in U.S. Patent Publication No. 20050118651, U.S. Patent Publication No. 20060198851, International Patent Publication No. WO 04/108895, and International Patent Publication No. WO 06/066089, all of which are incorporated by reference in their entirety herein for all purposes. 12A11 is a mAb that specifically binds to an N-terminal epitope located in the human β-amyloid peptide, specifically, residues 3-7. A cell line producing the 12A11 monoclonal antibody was deposited at the ATCC (American Type Culture Collection, 10801 University Boulevard, Manassas, Va. 20110-2209) on Dec. 12, 2005 and has the ATCC accession number PTA-7271.

A first version of the humanized 12A11 antibody comprising a light chain having the amino acid sequence designated SEQ ID NO: 7 and a heavy chain having the amino acid sequence designated SEQ ID NO: 8 (version 1) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile Ser    (SEQ ID NO: 7)

Cys Arg Ser Ser Gln Ser Ile Val His Ser Asn Gly Asn Thr Tyr Leu Glu Trp Tyr Leu Gln Lys

Pro Gly Gln Ser Pro Gln Leu Leu Ile Tyr Lys Val Ser Asn Arg Phe Ser Gly Val Pro Asp Arg

Phe Ser Gly Ser Gly Ser Gly Thr Asp Phe Thr Leu Lys Ile Ser Arg Val Glu Ala Glu Asp Val

Gly Val Tyr Tyr Cys Phe Gln Ser Ser His Val Pro Leu Thr Phe Gly Gln Gly Thr Lys Leu

Glu Ile Lys

Humanized 12A11 Heavy Chain (version 1)
Gln Val Gln Leu Val Glu Ser Gly Gly Gly Val Val Gln Pro Gly Arg Ser Leu Arg Leu Ser    (SEQ ID NO: 8)

Cys Ala Phe Ser Gly Phe Ser Leu Ser Thr Ser Gly Met Ser Val Gly Trp Ile Arg Gln Ala Pro

Gly Lys Gly Leu Glu Trp Leu Ala His Ile Trp Trp Asp Asp Lys Tyr Tyr Asn Pro Ser

Leu Lys Ser Arg Leu Thr Ile Ser Lys Asp Thr Ser Lys Asn Thr Val Tyr Leu Gln Met Asn

Ser Leu Arg Ala Glu Asp Thr Ala Val Tyr Tyr Cys Ala Arg Arg Thr Thr Thr Ala Asp Tyr

Phe Ala Tyr Trp Gly Gln Gly Thr Thr Val Thr Val Ser Ser
```

A second version of the humanized 12A11 antibody comprising a light chain having the amino acid sequence designated SEQ ID NO: 7 and a heavy chain having the amino acid sequence designated SEQ ID NO: 9 (version 2) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile Ser    (SEQ ID NO. 7)

Cys Arg Ser Ser Gln Ser Ile Val His Ser Asn Gly Asn Thr Tyr Leu Glu Trp Tyr Leu Gln Lys

Pro Gly Gln Ser Pro Gln Leu Leu Ile Tyr Lys Val Ser Asn Arg Phe Ser Gly Val Pro Asp Arg

Phe Ser Gly Ser Gly Ser Gly Thr Asp Phe Thr Leu Lys Ile Ser Arg Val Glu Ala Glu Asp Val

Gly Val Tyr Tyr Cys Phe Gln Ser Ser His Val Pro Leu Thr Phe Gly Gln Gly Thr Lys Leu

Glu Ile Lys

Humanized 12A11 Heavy Chain (version 2)
Gln Val Gln Leu Val Glu Ser Gly Gly Gly Val Val Gln Pro Gly Arg Ser Leu Arg Leu Ser    (SEQ ID NO: 9)

Cys Ala Phe Ser Gly Phe Thr Leu Ser Thr Ser Gly Met Ser Val Gly Trp Ile Arg Gln Ala Pro

Gly Lys Gly Leu Glu Trp Val Ala His Ile Trp Trp Asp Asp Lys Tyr Tyr Asn Pro Ser

Leu Lys Ser Arg Phe Thr Ile Ser Lys Asp Thr Ser Lys Asn Thr Leu Tyr Leu Gln Met Asn

Ser Leu Arg Ala Glu Asp Thr Ala Val Tyr Tyr Cys Ala Arg Arg Thr Thr Thr Ala Asp Tyr

Phe Ala Tyr Trp Gly Gln Gly Thr Thr Val Thr Val Ser Ser
```

A third version of the humanized 12A11 antibody comprising a light chain having the amino acid sequence designated SEQ ID NO: 7 and a heavy chain having the amino acid sequence designated SEQ ID NO: 10 (version 2.1) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile     (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A1 1 Heavy Chain (version 2.1)
Gln Val Gln Leu Val Glu Ser Gly Gly Gly Val Val Gln Pro Gly Arg Ser Leu Arg Leu Ser     (SEQ ID NO: 10)

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Asp Lys Tyr Tyr Asn Pro

Ser Leu Lys Ser Arg Phe Thr Ile Ser Lys Asp Asn Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A fourth version of the humanized 12A11 antibody comprising a light chain having the amino acid sequence designated SEQ ID NO: 7 and a heavy chain having the amino acid sequence designated SEQ ID NO: 11 (version 3) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile     (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 3)
Gln Val Gln Leu Val Glu Ser Gly Gly Gly Val Val Gln Pro Gly Arg Ser Leu Arg Leu Ser     (SEQ ID NO: 11)

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Asp Lys Tyr Tyr Asn Pro

Ser Leu Lys Ser Arg Phe Thr Ile Ser Arg Asp Asn Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A fifth version of the humanized 12A11 antibody comprising a light chain having the amino acid sequence designated SEQ ID NO: 7 and a heavy chain having the amino acid sequence designated SEQ ID NO: 12 (version 4.1) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO. 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 4.1)
Gln Val Gln Leu Val Glu Ser Gly Gly Gly Val Val Gln Pro Gly Arg Ser Leu Arg Leu Ser    (SEQ ID NO: 12)

Cys Ala Phe Ser Gly Phe Thr Leu Ser Thr Ser Gly Met Ser Val Gly Trp Ile Arg Gln Ala

Pro Gly Lys Gly Leu Glu Trp Leu Ala His Ile Trp Trp Asp Asp Lys Tyr Tyr Asn Pro

Ser Leu Lys Ser Arg Leu Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A sixth version of the humanized 12A11 antibody comprising a light chain having the amino acid sequence designated SEQ ID NO: 7 and a heavy chain having the amino acid sequence designated SEQ ID NO: 13 (version 4.2) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 4.2)
Gln Val Gln Leu Val Glu Ser Gly Gly Gly Val Val Gln Pro Gly Arg Ser Leu Arg Leu Ser    (SEQ ID NO: 13)

Cys Ala Phe Ser Gly Phe Ser Leu Ser Thr Ser Gly Met Ser Val Gly Trp Ile Arg Gln Ala

Pro Gly Lys Gly Leu Glu Trp Val Ala His Ile Trp Trp Asp Asp Lys Tyr Tyr Asn Pro

Ser Leu Lys Ser Arg Leu Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

An seventh version of the humanized 12A11 antibody comprising a light chain having the amino acid sequence designated SEQ ID NO: 7 and a heavy chain having the amino acid sequence designated SEQ ID NO: 14 (version 4.3) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 4.3)
Gln Val Gln Leu Val Glu Ser Gly Gly Gly Val Val Gln Pro Gly Arg Ser Leu Arg Leu Ser      (SEQ ID NO: 14)

Cys Ala Phe Ser Gly Phe Ser Leu Ser Thr Ser Gly Met Ser Val Gly Trp Ile Arg Gln Ala

Pro Gly Lys Gly Leu Glu Trp Leu Ala His Ile Trp Trp Asp Asp Asp Lys Tyr Tyr Asn Pro

Ser Leu Lys Ser Arg Phe Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A eighth version of the humanized 12A11 antibody comprising a light chain having the amino acid sequence designated SEQ ID NO: 7 and a heavy chain having the amino acid sequence designated SEQ ID NO: 15 (version 4.4) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 4.4)
Gln Val Gln Leu Val Glu Ser Gly Gly Gly Val Val Gln Pro Gly Arg Ser Leu Arg Leu Ser      (SEQ ID NO: 15)

Cys Ala Phe Ser Gly Phe Ser Leu Ser Thr Ser Gly Met Ser Val Gly Trp Ile Arg Gln Ala

Pro Gly Lys Gly Leu Glu Trp Leu Ala His Ile Trp Trp Asp Asp Asp Lys Tyr Tyr Asn Pro

Ser Leu Lys Ser Arg Leu Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A ninth version of the humanized 12A11 antibody comprising a light chain having the amino acid sequence designated SEQ ID NO: 7 and a heavy chain having the amino acid sequence designated SEQ ID NO: 16 (version 5.1) is described in U.S. Pat. No. 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID. NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val
```

-continued

```
Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Gln Ile Lys

Humanized 12A11 Heavy Chain (version 5.1)
Gln Val Gln Leu Val Glu Ser Gly Gly Gly Val Val Gln Pro Gly Arg Ser Leu Arg Leu Ser    (SEQ ID NO: 16)

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Lys Tyr Tyr Asn Pro

Ser Leu Lys Ser Arg Leu Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A tenth version of the humanized 12A11 antibody comprising a light chain having the amino acid sequence designated SEQ ID NO: 7 and a heavy chain having the amino acid sequence designated SEQ ID NO: 17 (version 5.2) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 5.2)
Gln Val Gln Leu Val Glu Ser Gly Gly Gly Val Val Gln Pro Gly Arg Ser Leu Arg Leu Ser    (SEQ ID NO: 17)

Cys Ala Phe Ser Gly Phe Thr Leu Ser Thr Ser Gly Met Ser Val Gly Trp Ile Arg Gln Ala

Pro Gly Lys Gly Leu Glu Trp Leu Ala His Ile Trp Trp Asp Asp Lys Tyr Tyr Asn Pro

Ser Leu Lys Ser Arg Phe Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

An eleventh version of the humanized 12A11 antibody comprising a light chain having the amino acid sequence designated SEQ ID NO: 7 and a heavy chain having the amino acid sequence designated SEQ ID NO: 18 (version 5.3) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 5.3)
Gln Val Gln Leu Val Glu Ser Gly Gly Gly Val Val Gln Pro Gly Arg Ser Leu Arg Leu Ser    (SEQ ID NO: 18)
```

```
Cys Ala Phe Ser Gly Phe Thr Leu Ser Thr Ser Gly Met Ser Val Gly Trp Ile Arg Gln Ala

Pro Gly Lys Gly Leu Glu Trp Leu Ala His Ile Trp Trp Asp Asp Lys Tyr Tyr Asn Pro

Ser Leu Lys Ser Arg Leu Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser Val
```

A twelfth version of the humanized 12A11 antibody comprising a light chain having the amino acid sequence designated SEQ ID NO: 7 and a heavy chain having the amino acid sequence designated SEQ ID NO: 19 (version 5.4) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 5.4)
Gln Val Gln Leu Val Glu Ser Gly Gly Gly Val Val Gln Pro Gly Arg Ser Leu Arg Leu Ser    (SEQ ID NO: 19)

Cys Ala Phe Ser Gly Phe Ser Leu Ser Thr Ser Gly Met Ser Val Gly Trp Ile Arg Gln Ala

Pro Gly Lys Gly Leu Glu Trp Val Ala His Ile Trp Trp Asp Asp Lys Tyr Tyr Asn Pro

Ser Leu Lys Ser Arg Phe Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser Val
```

A thirteenth version of the humanized 12A11 antibody comprising a light chain having the amino acid sequence designated SEQ ID NO: 7 and a heavy chain having the amino acid sequence designated SEQ ID NO: 20 (version 5.5) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Gln

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 5.5)
Gln Val Gln Leu Val Glu Ser Gly Gly Gly Val Val Gln Pro Gly Arg Ser Leu Arg Leu Ser    (SEQ ID NO: 20)

Cys Ala Phe Ser Gly Phe Ser Leu Ser Thr Ser Gly Met Ser Val Gly Trp Ile Arg Gln Ala

Pro Gly Lys Gly Leu Glu Trp Val Ala His Ile Trp Trp Asp Asp Lys Tyr Tyr Asn Pro

Ser Leu Lys Ser Arg Leu Thr Ile Ser Lys Asp Thr Ser Lys Asn Thr Leu Tyr Leu Gln Met
```

```
Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A fourteenth version of the humanized 12A11 antibody comprising a light chain having the amino acid sequence designated SEQ ID NO: 7 and a heavy chain having the amino acid sequence designated SEQ ID NO: 21 (version 5.6) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 5.6)
Gln Val Gln Leu Val Glu Ser Gly Gly Gly Val Val Gln Pro Gly Arg Ser Leu Arg Leu Ser    (SEQ ID NO: 21)

Cys Ala Phe Ser Gly Phe Ser Leu Ser Thr Ser Gly Met Ser Val Gly Trp Ile Arg Gln Ala

Pro Gly Lys Gly Leu Glu Trp Leu Ala His Ile Trp Trp Asp Asp Asp Lys Tyr Tyr Asn Pro

Ser Leu Lys Ser Arg Phe Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A fifteenth version of the humanized 12A11 antibody comprising a light chain having the amino acid sequence designated SEQ ID NO: 7 and a heavy chain having the amino acid sequence designated SEQ ID NO: 22 (version 6.1) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile    (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 6.1)
Gln Val Gln Leu Val Glu Ser Gly Gly Gly Val Val Gln Pro Gly Arg Ser Leu Arg Leu Ser    (SEQ ID NO: 22)

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Asp Lys Tyr Tyr Asn Pro

Ser Leu Lys Ser Arg Phe Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A sixteenth version of the humanized 12A11 antibody comprising a light chain having the amino acid sequence designated SEQ ID NO: 7 and a heavy chain having the amino acid sequence designated SEQ ID NO: 23 (version 6.2) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 6.2)
Gln Val Gln Leu Val Glu Ser Gly Gly Gly Val Val Gln Pro Gly Arg Ser Leu Arg Leu Ser     (SEQ ID NO: 23)

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Lys Tyr Tyr Asn Pro

Ser Leu Lys Ser Arg Leu Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A seventeenth version of the humanized 12A11 antibody comprising a light chain having the amino acid sequence designated SEQ ID NO: 7 and a heavy chain having the amino acid sequence designated SEQ ID NO: 24 (version 6.3) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 6.3)
Gln Val Gln Leu Val Glu Ser Gly Gly Gly Val Val Gln Pro Gly Arg Ser Leu Arg Leu Ser     (SEQ ID NO: 24)

Cys Ala Phe Ser Gly Phe Thr Leu Ser Thr Ser Gly Met Ser Val Gly Trp Ile Arg Gln Ala

Pro Gly Lys Gly Leu Glu Trp Leu Ala His Ile Trp Trp Asp Asp Lys Tyr Tyr Asn Pro

Ser Leu Lys Ser Arg Phe Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A eighteenth version of the humanized 12A11 antibody comprising a light chain having the amino acid sequence designated SEQ ID NO: 7 and a heavy chain having the amino acid sequence designated SEQ ID NO: 25 (version 6.4) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Gln Ile Lys

Humanized 12A11 Heavy Chain (version 6.4)
Gln Val Gln Leu Val Glu Ser Gly Gly Gly Val Val Gln Pro Gly Arg Ser Leu Arg Leu Ser     (SEQ ID NO: 25)

Cys Ala Phe Ser Gly Phe Ser Leu Ser Thr Ser Gly Met Ser Val Gly Trp Ile Arg Gln Ala

Pro Gly Lys Gly Leu Glu Trp Val Ala His Ile Trp Trp Asp Asp Lys Tyr Tyr Asn Pro

Ser Leu Lys Ser Arg Phe Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A nineteenth version of the humanized 12A11 antibody comprising a light chain having the amino acid sequence designated SEQ ID NO: 7 and a heavy chain having the amino acid sequence designated SEQ ID NO: 26 (version 7) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile      (SEQ ID NO: 7)

Ser Cys Arg Ser Ser Gln Ser Ile Val His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Ser Ser His Val Pro Leu Thr Phe Gly Gln

Gly Thr Lys Leu Glu Ile Lys

Humanized 12A11 Heavy Chain (version 7)
Gln Val Gln Leu Val Glu Ser Gly Gly Gly Val Val Gln Pro Gly Arg Ser Leu Arg Leu Ser     (SEQ ID NO: 26)

Cys Ala Phe Ser Gly Phe Thr Leu Ser Thr Ser Gly Met Ser Val Gly Trp Val Arg Gln Ala

Pro Gly Lys Gly Leu Glu Trp Leu Ala His Ile Trp Trp Asp Asp Lys Tyr Tyr Asn Pro

Ser Leu Lys Ser Arg Leu Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala Asp

Tyr Phe Ala Tyr Trp Gly Gln Gly Thr Thr Val Thr Val Ser Ser
```

A twentieth version of the humanized 12A11 antibody comprising a light chain having the amino acid sequence designated SEQ ID NO: 7 and a heavy chain having the amino acid sequence designated SEQ ID NO: 27 (version 8) is described in US 20050118651 A1 published on Jun. 2, 2005, which is incorporated herein by reference for all purposes.

```
Humanized 12A11 Light Chain
Asp Val Val Met Thr Gln Ser Pro Leu Ser Leu Pro Val Thr Pro Gly Glu Pro Ala Ser Ile Ser     (SEQ ID NO: 7)

Cys Arg Ser Ser Gln Ser Ile Val His Ser Asn Gly Asn Thr Tyr Leu Glu Trp Tyr Leu Gln Lys

Pro Gly Gln Ser Pro Gln Leu Leu Ile Tyr Lys Val Ser Asn Arg Phe Ser Gly Val Pro Asp Arg

Phe Ser Gly Ser Gly Ser Gly Thr Asp Phe Thr Leu Lys Ile Ser Arg Val Glu Ala Glu Asp Val
```

-continued

```
Gly Val Tyr Tyr Cys Phe Gln Ser Ser His Val Pro Leu Thr Phe Gly Gln Gly Thr Lys Leu

Gln Ile Lys

Humanized 12A11 Heavy Chain (version 8)
Gln Val Gln Leu Val Glu Ser Gly Gly Gly Val Val Gln Pro Gly Arg Ser Leu Arg Leu Ser        (SEQ ID NO: 27)

Cys Ala Phe Ser Gly Phe Ser Leu Ser Thr Ser Gly Met Ser Val Gly Trp Ile Arg Gln Ala Pro

Gly Lys Gly Leu Glu Trp Leu Ala His Ile Trp Trp Asp Asp Lys Tyr Tyr Asn Pro Ser

Leu Lys Ser Arg Leu Thr Ile Ser Lys Asp Asn Ser Lys Asn Thr Val Tyr Leu Gln Met Asn

Ser Leu Arg Ala Glu Asp Thr Ala Val Tyr Tyr Cys Ala Arg Arg Thr Thr Thr Ala Asp Tyr

Phe Ala Tyr Trp Gly Gln Gly Thr Thr Val Thr Val Ser Ser
```

Any of the antibodies described above can be produced with different isotypes or mutant isotypes to control the extent of binding to different Fc receptors. Antibodies lacking an Fc region (e.g., Fab fragments) lack binding to Fc receptors. Selection of isotype also affects binding to Fc receptors. The respective affinities of various human IgG isotypes for the three Fcγ receptors, FcγRI, FcγRII, and FcγRIII, have been determined (see Ravetch & Kinet, Annu. Rev. Immunol. 9, 457 (1991)). FcγRI is a high affinity receptor that binds to IgGs in monomeric form, and the latter two are low affinity receptors that bind IgGs only in multimeric form. In general, both IgG1 and IgG3 have significant binding activity to all three receptors, IgG4 to FcRI, and IgG2 to only one type of FcRII called IIa$_{LR}$ (see Parren et al., J. Immunol. 148, 695 (1992). Therefore, human isotype IgG1 is usually selected for stronger binding to Fcγ receptors is desired, and IgG2 is usually selected for weaker binding.

Mutations on adjacent or close sites in the hinge link region (e.g., replacing residues 234, 235, 236 and/or 237 with another residue) in all of the isotypes reduce affinity for Fcγ receptors, particularly FcγRI receptor. Optionally, positions 234, 236 and/or 237 are substituted with alanine and position 235 with glutamine. (See, e.g., U.S. Pat. No. 5,624,821.) Position 236 is missing in the human IgG2 isotype. Exemplary segments of amino acids for positions 234, 235 and 237 for human IgG2 are ala ala gly, val ala ala, ala ala ala, val glu ala, and ala glu ala. A preferred combination of mutants is L234A, L235A, and G237A for human isotype IgG1. A particular preferred antibody is bapineuzumab having human isotype IgG and these three mutations of the Fc region. Other substitutions that decrease finding to Fc gamma receptors are an E233P mutation (particularly in mouse IgG1) and D265A.

Amino acids in the constant region are numbered by alignment with the human antibody EU (see Cunningham et al., J. Biol. Chem., 9, 3161 (1970)). That is, the heavy and light chains of an antibody are aligned with the heavy and light chains of EU to maximize amino acid sequence identity and each amino acid in the antibody is assigned the same number as the corresponding amino acid in EU. The EU numbering system is conventional (see generally, Kabat et al, *Sequences of Protein of Immunological Interest*, NIH Publication No. 91-3242, US Department of Health and Human Services (1991)).

The affinity of an antibody for complement component Clq can be altered by mutating at least one of the amino acid residues 318, 320, and 322 of the heavy chain has been changed to a residue having a different side chain. Other suitable alterations for altering, e.g., reducing or abolishing specific Clq-binding to an antibody include changing any one of residues 318 (Glu), 320 (Lys) and 322 (Lys), to Ala. Clq binding activity can be abolished by replacing any one of the three specified residues with a residue having an inappropriate functionality on its side chain. It is not necessary to replace the ionic residues only with Ala to abolish Clq binding. It is also possible to use other alkyl-substituted non-ionic residues, such as Gly, ile, Leu, or Val, or such aromatic non-polar residues as Phe, Tyr, Trp and Pro in place of any one of the three residues in order to abolish Clq binding. In addition, it is also be possible to use such polar non-ionic residues as Ser, Thr, Cys, and Met in place of residues 320 and 322, but not 318, to abolish Clq binding activity. Replacement of the 318 (Glu) residue by a polar residue may modify but not abolish Clq binding activity. Replacing residue 297 (Asn) with Ala results in removal of lytic activity while only slightly reducing (about three fold weaker) affinity for Clq. This alteration destroys the glycosylation site and the presence of carbohydrate that is required for complement activation. Any other substitution at this site also destroy the glycosylation site.

III. Patients Amenable to (CAA) Treatment Regimes

Cerebral amyloid angiopathy is also known as congophilic angiopathy or cerebrovascular amyloidosis. It is a disease of small blood vessels in the brain in which deposits of amyloid protein in the vessel walls may lead to stroke, brain hemorrhage, white matter ischemia or dementia. Amyloid protein resembles a starch and is deposited in tissues during the course of certain chronic diseases.

CAA may affect patients over age 45, but is most common in patients over age 65, and becomes more common with increasing age. Men and women are equally affected. In some cases, CAA is sporadic but it may also be inherited as an autosomal dominant condition (a form of inheritance in which only one copy of a gene coding for a disease need be present for that disease to be expressed; if either parent has the disease, a child has a 50% chance of inheriting the disease). CAA is responsible for 5-20% of brain hemorrhage, and up to 30% of lobar hemorrhages localized to one lobe of the brain. CAA may be found during an autopsy in over one-third of persons over age 60, even though they may not have had brain hemorrhage, stroke, or other manifestations of the disease during life. In Alzheimer's disease, CAA is more common than in the general population, and may occur in more than 80% of Alzheimer's patients over age 60.

The cause of amyloid deposits in blood vessels in the brain in sporadic CAA is not known. In hereditary CAA, genetic defects, typically on chromosome 21, allow accumulation of amyloid, a protein made up of units called beta-pleated sheet fibrils. The fibrils tend to clump together, so that the amyloid cannot be dissolved and builds up in the brain blood vessel walls. One form of amyloid fibril subunit proteins is the amyloid beta protein. Cerebral amyloid angiopathy is a common neuropathological feature of Alzheimer's disease and is characterized by vascular deposition of fibrillar amyloid b-protein (VAβ). Vascular structural changes are associated with VAβ deposits, including localized loss of smooth muscle cells (SMC) and changes in extracellular matrix (ECM). Vascular phenotype may be characterized quantification of vascular elements along the vessel perimeter, e.g., vessel layer thickness, vessel size, luminal perimeter, intensity, the relative position of vessel elements, and area of the brain.

Amyloid deposits may destroy endothelial or smooth muscle cells, or both endothelial or smooth muscle cells, or cause inflammation in the blood vessel wall and may also cause the blood vessel to break more easily. Bleeding into the brain may also occur as tiny blood vessels carrying amyloid deposits become heavier and more brittle, and are therefore more likely to burst with minor trauma or with fluctuating blood pressure. Aneurysms, or ballooning of the blood vessel wall, may develop, and may also rupture as the stretched wall becomes thinner and is under more pressure.

The most common form of CAA is the sporadic form associated with aging. This type of CAA usually causes lobar hemorrhage, which may recur in different lobes of the brain. The frontal lobe (behind the forehead) and parietal lobe (behind the frontal lobe) are most often affected; the temporal lobe (near the temple) and occipital lobe (at the back of the brain) are affected less often; and the cerebellum (under the occipital lobe) is rarely affected. Approximately 10-50% of hemorrhages in sporadic CAA involve more than one lobe.

Symptoms of lobar hemorrhage in CAA include sudden onset of headache, neurologic symptoms such as weakness, sensory loss, visual changes, or speech problems, depending on which lobe is involved; and decreased level of consciousness (a patient who is difficult to arouse), nausea, and vomiting. Sporadic CAA may be associated with symptoms unrelated to lobar hemorrhage. Petechial hemorrhages (tiny hemorrhages involving many small vessels) may produce recurrent, brief neurologic symptoms secondary to seizures or decreased blood flow, or may produce rapidly progressive dementia (loss of memory and other brain functions) that worsens in distinct steps rather than gradually. Over 40% of patients with hemorrhage secondary to CAA also have dementia.

Genetic factors play a role in certain types of CAA and in diseases associated with CAA:

Dutch type of hereditary cerebral hemorrhage with amyloidosis (build up of amyloid protein in blood vessels): autosomal dominant, with a genetic mutation involving the amyloid precursor protein. Onset is at age 40-60 with headaches, brain hemorrhage often in the parietal lobe, strokes, and dementia. More than half of patients die from their first hemorrhage. Patients with the Dutch type of CAA may produce an abnormal anticoagulant, or blood thinner, which makes hemorrhage more likely.

Flemish type of hereditary cerebral hemorrhage with amyloidosis: autosomal dominant, with a mutation involving the amyloid precursor protein. Symptoms include brain hemorrhage or dementia.

Familial Alzheimer's disease: autosomal dominant, comprising 5-10% of all Alzheimer's disease cases (a brain disease in which death of nerve cells leads to progressive dementia).

Down Syndrome: caused by trisomy 21 (three rather than two copies of chromosome 21), causing excess amyloid precursor protein gene. Children with Down syndrome are mentally handicapped and may have heart problems.

Icelandic type of hereditary cerebral hemorrhage with amyloidosis: autosomal dominant, with mutation in the gene coding for cystatin C. Symptoms often begin at age 30-40 with multiple brain hemorrhages, dementia, paralysis (weakness), and death in 10-20 years. Headache occurs in more than half of patients, and seizures occur in one-quarter. Unlike most other forms of CAA, most hemorrhages involve the basal ganglia deep within the brain. (Basal ganglia are islands of tissues in the cerebellum part of the brain.)

Familial oculo-leptomeningeal amyloidosis: autosomal dominant with unknown gene defect(s), described in Japanese, Italian, and North American families. Symptoms can include dementia, ataxia (problems with coordination), spasticity (limb stiffness), strokes, seizures, peripheral neuropathy (disease affecting the nerves supplying the limbs), migraine, spinal cord problems, blindness, and deafness. Brain hemorrhage is rare as the amyloid protein is deposited in blood vessels in the eye and meninges (brain coverings), but not in the brain itself. In Italian families with the disease, patients may be affected as early as 20-30 years of age.

British type of familial amyloidosis: autosomal dominant with unknown gene defect(s), associated with progressive dementia, spasticity, and ataxia. Brain stem, spinal cord, and cerebellum all exhibit amyloid deposits, but hemorrhage typically does not occur.

In some methods, a patient has CAA and is free of symptoms of Alzheimer's or other disease amenable to treatment by antibodies to Aβ or agents capable of inducing the same. In other methods, the patient has concurrent CAA and Alzheimer's or other disease amenable to treatment by antibodies to Aβ or agents capable of inducing the same. In other methods, a patient is free of CAA and Alzheimer's disease and any other disease amenable to treatment by antibodies to Aβ or agents capable of inducing the same.

In asymptomatic patients, treatment can begin at any age (e.g., 10, 20, or 30). Usually, however, it is not necessary to begin treatment until a patient reaches 40, 50, 60, or 70. Treatment typically entails multiple dosages over a period of time. Treatment can be monitored by assaying antibody, or activated T-cell or B-cell responses to the therapeutic agent (antibody to Aβ, or a fragment thereof) over time. If the response falls, a booster dosage is indicated.

Optionally, presence of absence of symptoms, signs or risk factors of a disease is determined before beginning treatment.

IV. Diagnosis and Monitoring of CAA Patients

As in most neurologic diseases, diagnosis is made most often from the patient's history, with careful inquiry into family history and the patient's onset and pattern of symptoms, as well as neurologic examination. Brain computed tomography scan (CT) or magnetic resonance imaging (MRI) may identify lobar hemorrhage, stroke, or petechial hemorrhages, and are important in excluding arteriovenous malformation, brain tumor, or other causes of hemorrhage. Angiography (x-ray study of the interior of blood vessels and the heart) is not helpful in diagnosis of CAA, but may be needed to exclude aneurysm. Brain biopsy (surgical removal of a small piece of brain tissue) may show characteristic amyloid deposits. If diagnosis is uncertain, biopsy may be needed to rule out conditions which are potentially treatable. Lumbar puncture to examine cerebrospinal fluid proteins may show characteristic abnormalities.

CAA with hemorrhage must be distinguished from other types of brain hemorrhage. In CAA, hemorrhage typically occurs in the lobar region, often ruptures into the subarachnoid space between the brain and its coverings, and occurs at night. In hemorrhage related to high blood pressure, hemorrhage is usually deeper within the brain, ruptures into the ventricles or cavities deep inside the brain, and occurs during daytime activities. Other causes of brain hemorrhage are arteriovenous malformations, trauma, aneurysms, bleeding into a brain tumor, vasculitis (inflammation of blood vessels), or bleeding disorders. Patients can be monitored for cerebral microhemorrhage by MRI and/or for vascular amyloid removal by positron emission tomography (PET) scan.

The invention provides methods of monitoring cerebral vascular phenotype in a patient suffering from vascular Aβ deposits. The methods are particularly useful for monitoring a course of treatment being administered to a patient. The methods are useful for monitoring both active immunization (e.g., antibody produced in response to administration of immunogen) and passive immunization (e.g., measuring level of administered antibody). The monitoring may comprise quantification of vascular elements along the vessel perimeter. Vascular elements to be measured include vessel layer thickness, vessel size, luminal perimeter, intensity, and the relative position of vessel elements.

Patients amenable to treatment include individuals at risk of a CAA but not showing symptoms, as well as patients presently showing symptoms.

V. Treatment Regimes

In prophylactic applications, pharmaceutical compositions or medicaments are administered to a patient susceptible to, or otherwise at risk of a CAA in regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a patient suspected of, or already suffering from such a disease in a regime comprising an amount and frequency of administration of the composition sufficient to cure, or at least partially arrest, the symptoms of the disease (physiological, biochemical, histologic and/or behavioral), including its complications and intermediate pathological phenotypes in development of the disease. An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylactically-effective regime. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 μg per patient and more usually from 5-500 μg per injection for human administration. Typically about 10, 20, 50 or 100 μg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage regime is usually 0.01 to 5 mg/kg, of the host body weight. In particular, the dosage ranges from about 0.5 to less than 5 mg/kg, and more usually 0.5 to 3 mg/kg, of the host body weight. For example dosages can be less than 5 mg/kg body weight or 1.5 mg/kg body weight or within the range of 0.5 to 1.5 mg/kg, preferably at least 1.5 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Exemplary passive dosage schedules include 1.5-3 mg/kg or 1.5 mg/kg every thirteen weeks. Agents of the invention are usually administered on multiple occasions. Intervals between single dosages can be weekly, monthly, every thirteen weeks, or yearly. Intervals can also be irregular as indicated by measuring blood levels of antibody to Aβ in the patient.

In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

Preferred regimes for administering antibodies specific for the N-terminus of Aβ achieve an average serum concentration of administered antibody of 1-15 μg/ml in a patient. The serum concentration can be determined by actual measurement or predicted from standard pharmacokinetics (e.g., Win-Nonline Version 4.0.1 (Pharsight Corporation, Cary, USA)) based on the amount of antibody administered, frequency of administration, route of administration and antibody half-life. The average antibody concentration in the serum is preferably within a range of 1-10, 1-5 or 2-4 μg/ml.

For intravenous administration, doses of 0.1 to 5 mg/kg of antibody administered between monthly and quarterly (every 13 weeks are preferred). For quarterly administration, the dose is preferably in a range of 0.5-3, 0.5-2 or 0.5-1.5 mg/kg. Preferred doses of antibody for monthly intravenous administration occur in the range of 0.1-1.0 mg/kg antibody or preferably 0.5-1.0 mg/kg antibody.

For more frequent dosing, e.g., from weekly to monthly dosing, subcutaneous administration is preferred. The doses used for subcutaneous dosing are usually in the range of 0.1 to 0.6 mg/kg or 0.01-0.35 mg/kg, preferably, 0.05-0.25 mg/kg. For weekly or biweekly dosing, the dose is preferably in the range of 0.015-0.2 mg/kg, or 0.05-0.15 mg/kg. For weekly dosing, the dose is preferably 0.05 to 0.07 mg/kg, e.g., 0.06 mg/kg. For biweekly dosing, the dose is preferably 0.1 to 0.15 mg/kg. For monthly dosing, the dose is preferably 0.1 to 0.3 mg/kg or 2 mg/kg. Monthly dosing includes dosing by the calendar month or lunar month (i.e., every four weeks).

The treatment regime is usually continued so that the average serum concentrations of antibody described above are maintained for at least six months or a year, and sometimes for life. The serum concentration can be measured at any time during treatment and the dose and/or frequency of administration increased if the average concentration falls beneath a target range or the dose and/or frequency decreased if the average concentration falls above a target range.

Although determining optimal plasma concentrations of antibody is useful in determining a dosage regime or optimizing dosage in an individual patient, in practice once an effective dosage regime in terms of mg/kg or mg and frequency of administration has been determined, the same dosage regime can be used on many other patients without the need for detailed calculation or measurement of patient titers. Thus, any of the above mentioned dosages and treatment regimes can be used irrespective whether a titer is measured or predicted in a particular patient. For example, one suitable regime is intravenous administration at monthly intervals with a dose in range of 0.1-1.0 mg/kg antibody or preferably 0.5-1.0 mg/kg antibody. For subcutaneous dosing the dose used is usually in the range of 0.01-0.6 mg/kg or 0.01-0.35 mg/kg, preferably, 0.05-0.25 mg/kg. For weekly or biweekly dosing, the dose is preferably in the range of 0.015-0.2 mg/kg, or 0.05-0.15 mg/kg. For weekly dosing, the dose is preferably 0.05 to 0.07 mg/kg, e.g., 0.06 mg/kg. For biweekly dosing, the dose is preferably 0.1 to 0.15 mg/kg. For monthly dosing, the dose is preferably 0.1 to 0.3 mg/kg or 2 mg/kg.

Here as elsewhere in the application, dosages expressed in mg/kg can be converted to absolute mass dosages by multiplying by the mass of a typical patient (e.g., 70 or 75 kg) typically rounding to a whole number. Expressed in terms of absolute mass, antibodies are usually administered at a dose of 1-40 mg at a frequency of between weekly and monthly. Preferred ranges are 5-25 mg or 2.5-15 mg at a frequency of weekly to monthly. For weekly to biweekly administration, the dose is often 1-12 mg or 2.5 to 10 mg. For weekly administration, the dose is often 2.5 to 5 mg or 4-5 mg. For biweekly administration, the dose can be 7-10 mg. The mass of antibody packaged for administration in unit doses is usually round to whole number, such as 1, 5, 10, 20, 30, 40, 50, 75 or 100 mg.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 10 to 250 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Agents of the invention can optionally be administered in combination with other agents that are at least partly effective in treatment of amyloidogenic disease. In the case of CAA, in which amyloid deposits occur in the brain vasculature, agents of the invention can also be administered in conjunction with other agents that increase passage of the agents of the invention across the blood-brain barrier.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Agents for inducing an immune response can be administered by parenteral, topical, intravenous, oral, subcutaneous, intraarterial, intracranial, intrathecal, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

As noted above, agents inducing an immunogenic response against Aβ respectively can be administered in combination. The agents can be combined in a single preparation or kit for simultaneous, sequential or separate use. The agents can occupy separate vials in the preparation or kit or can be combined in a single vial. These agents of the invention can optionally be administered in combination with other agents that are at least partly effective in treatment of CAA. The glycosaminoglycan-mimetic CEREBRILL (Neurochem) is currently in clinical trials for treatment of CAA. Most patients with CAA should be counseled to avoid agents that "thin the blood" or interfere with blood clotting. The medicine with the strongest effect on blood clotting (and thus the riskiest for CAA patients) is warfarin (also known by its trade name "Coumadin"). Other medicines that have weaker effects on the blood are aspirin, ticlopidine ("Ticlid"), clopidogrel ("Plavix"), and most of the anti-inflammatory medications such as ibuprofen. Also it is usually prudent to monitor the blood pressure after a patient recovers from a bleeding stroke and maintain it in the normal range. Seizures, or recurrent neurologic symptoms thought to be seizures, should be treated with anti-epileptic drugs, although Depakote (sodium valproate) should be avoided because of its antiplatelet effect. Anti-epileptic drugs are sometimes given to patients with large lobar hemorrhage in an attempt to prevent seizures, although the benefit of this is unclear. Surgery may be needed to remove brain hemorrhage. CAA may be rarely associated with cerebral vasculitis, or inflammation of the blood vessel walls. In these cases treatment with steroids or immune system suppressants may be helpful.

Immunogenic agents of the invention, such as peptides, are sometimes administered in combination with an adjuvant. A variety of adjuvants can be used in combination with a peptide to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., *Vaccine Design: The Subunit and Adjuvant Approach* (eds. Powell & Newman, Plenum Press, NY, 1995); U.S. Pat. No. 5,057,540, Aquila BioPharmaceuticals, Framingham, Mass. Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Alternatively, Aβ can be coupled to an adjuvant. However, such coupling should not substantially change the conformation of the immunogenalphaso as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucosaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include RC-529, GM-CSF and pharmaceutically acceptable grades of Incomplete Freund's Adjuvant (IFA) (sold under the trade name of Montanide). Other adjuvants include cytokines, such as interleukins (e.g., IL-1, IL-2, IL-4, IL-6, IL-12, IL-13, and IL-15), macrophage colony stimulating factor (M-CSF), granulocyte-macrophage colony stimulating factor (GM-CSF), and tumor necrosis factor (TNF). Another class of adjuvants is glycolipid analogues including N-glycosylamides, N-glycosylureas and N-glycosylcarbamates, each of which is substituted in the sugar residue by an amino acid, as immuno-modulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body. For example, compositions containing biologics are typically sterilized by filter sterilization. Compositions can be formulated for single dose administration.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin patch or using transferosomes (Paul et al., *Eur. J. Immunol.* 25, 3521-24 (1995); Cevc et al., *Biochem. Biophys. Acta* 1368, 201-15 (1998)).

VI. Kits

The invention further provides therapeutic products. The products comprise a glass vial and instructions. The glass vial contains a formulation comprising about 10 mg to about 250 mg of a humanized anti Aβ antibody, about 4% mannitol or about 150 mM NaCl, about 5 mM to about 10 mM histidine, and about 10 mM methionine. The instructions include monitoring the patient for cerebral microhemorrhage by MRI or monitoring the patient for vascular amyloid removal by PET scan.

EXAMPLES

Example 1

Materials and Methods

Study Design. The effects of chronic, passive immunization on established VAβ in the PDAPP mouse were examined in two studies. Study A was designed to compare the efficacy of an N-terminal antibody (3D6, recognizing Aβ1-5) with a mid-region antibody (266, recognizing Aβ16-23) at a single dose. Study B was a 3D6 dose-response study. In both studies, 12-month-old, female, heterozygous PDAPP mice were divided into groups of 40; the groups were matched as closely as possible for age and transgenic parent. In a separate assessment, a group of 40 animals was sacrificed at to determine vascular amyloid levels at 12 months of age. As outlined in Table 1, mice in treatment groups were injected intraperitoneally with murine monoclonal antibodies 3D6 γ2a (at 3 dose levels), 266 γ1, or TY11-15 (as negative control). All treated animals received an initial loading dose of 250% of the planned weekly dose. Doses per animal were calculated based on the historical average weight of a PDAPP mouse in this age range, 50 grams. Animals were treated weekly for approximately 6 months (26 weeks). After termination of the in-life phase, VAβ and microhemorrhage presence and extent were evaluated. All work was performed in accordance with Elan IACUC guidelines.

Preparation of antibodies. Preparation methods for antibodies 3D6 (recognizing Aβ 1-5), 266 (recognizing Aβ 16-23), and 12A11 (recognizing Aβ 3-7) have been described previously (see K. Johnson-Wood et al., *Proc Natl Acad Sci USA* 94, 1550-5 (1997), P. Seubert et al., *Nature* 359, 325-7 (1992), F. Bard et al., *Proc Natl Acad Sci USA* 100, 2023-8 (2003)). TY11/15 (IgG$_{2a}$ isotype) served as the irrelevant control antibody. It recognizes an unknown human lymphocyte antigen and does not recognize mouse lymphocytes. Antibodies 3D6 and 12A11 were labeled with NHS-biotin as described previously (see P. Seubert et al., *Nature* 359, 325-7 (1992)).

Brain tissue preparation for histochemistry. Animals were deeply anesthetized with isofluorane and perfused with saline intracardially. One hemisphere from each brain was immersion-fixed for 48 hours in 4% paraformaldehyde at 4° C. and sectioned coronally at 40 µm on a vibrating-blade microtome. The sections were stored in antifreeze solution (30% glycerol/30% ethylene glycol in 40 mM Na$_2$HPO$_4$, pH 7.4) at −20° C. prior to immunostaining. Four to 6 sections, spanning the rostral hippocampal level at 240-µm intervals, were selected from each brain for analysis. Brains and sections in which the frontal cortex was damaged during the removal from the skull were excluded from analyses. Final numbers are indicated in the Results. Sections were stained and analyzed by investigators blinded to the treatment status.

VAβ and microhemorrhage co-labeling histochemical procedure: Aβ deposits were labeled with biotinylated antibodies 3D6 (3.0 µg/ml) or 12A11 (3.0 µg/ml) in 1% horse serum in PBS overnight at 4° C. The floating sections were then reacted with an avidin-biotinylated horseradish peroxidase complex and developed using 3,3-diaminobenzidene. Sections were then mounted on slides and co-stained with a Perls iron reaction (see M. M. Racke et al., supra) modified by incubation at 37° C. to intensify hemosiderin reaction product. The presence of hemosiderin is an indication of a past microhemorrhage event.

VAβ analysis: 3D6-immunoreactive blood vessels were assessed in each animal by classifying the animal to one of 2 categories reflecting the amount of VAβ: "none to little VAβ" (≦3 amyloid-positive vessels in any single section per animal) or "moderate VAβ" (>3 amyloid-positive vessels in any single section per animal). This classification method was developed by counting the number of all amyloid-containing vessels in the tissues from studies A and B and using a ROC curve to identify a cutoff that was the optimal one to balance the sensitivity and specificity. Vessels were counted if they contained any amount of amyloid, so both partially cleared vessels and uncleared vessels were counted. Pairwise comparisons using Fisher's Exact Test (FET) were performed to identify significant differences in VAβ. Within each study, the Hochberg method (see Y. Hochberg, *Biometrika* 75, 800-802 (1988)) was used to adjust for multiple pairwise comparisons.

Microhemorrhage analysis: Each animal was scored on a 0-3 scale for presence, amount, location, and intensity of hemosiderin staining across the sections. A score of "0" indicated very little or no staining, a "1" indicated small punctuate or weak staining in a few sections per animal, a "2" was assigned to contiguous accumulations with greater staining intensity in multiple sections, and "3" reflected the darkest observed staining in most of the sections, usually encompassing most of the surrounding affected vessel. These ratings were designed to reflect the range of hemosiderin-positive staining confined to the present preclinical animal study, and therefore do not represent or translate to ratings of clinical hemorrhagic disorders. Pair-wise comparisons using Fisher's exact test were performed to test for differences between treatment groups. Observations were also made regarding the morphological appearance of the immunolabeled amyloid and its spatial relationship with hemosiderin. Within each study, the Hochberg method (see Y. Hochberg, supra) was used to adjust for multiple pairwise comparisons.

Results

Vascular Aβ. VAβ was prominent in the leptomeninges and superficial parenchyma of untreated, 18-month-old PDAPP mice as revealed by thioflavin S staining (FIG. 1*a*) for compact amyloid and by antibody 3D6 (FIG. 1*b*), which recognizes both compact and diffuse amyloid in the PDAPP mouse and human AD (FIG. 1*c*). VAβ was largely confined to the meninges and immediately underlying superficial brain layers (FIG. 1*d*). It was especially predominant in the cortex, particularly in midline vessels of the sagittal sinus, and similar distributions of VAβ were revealed by thioflavin S (FIG. 1) and antibody 3D6 (FIG. 1*b*) in both mouse and human tissues (FIG. 1*c*).

In the single dose comparison study of the N-terminal and mid-region antibodies (Study A), 3D6 at 3 mg/kg completely cleared or prevented VAβ compared with either 266 or TY11-15 (FIG. 2*a-e*); these differences were statistically significant (p-values<0.0001 for both comparisons). 3D6 treatment also lowered the parenchymal amyloid plaque burden by 98% (p<0.0001), while 266 produced no effect. VAβ was present at moderate levels in 23% of 12-month-old mice before the start of treatment. FET p-values<0.025 are statistically significant using the Hochberg method of multiple comparisons.

Figure 3:
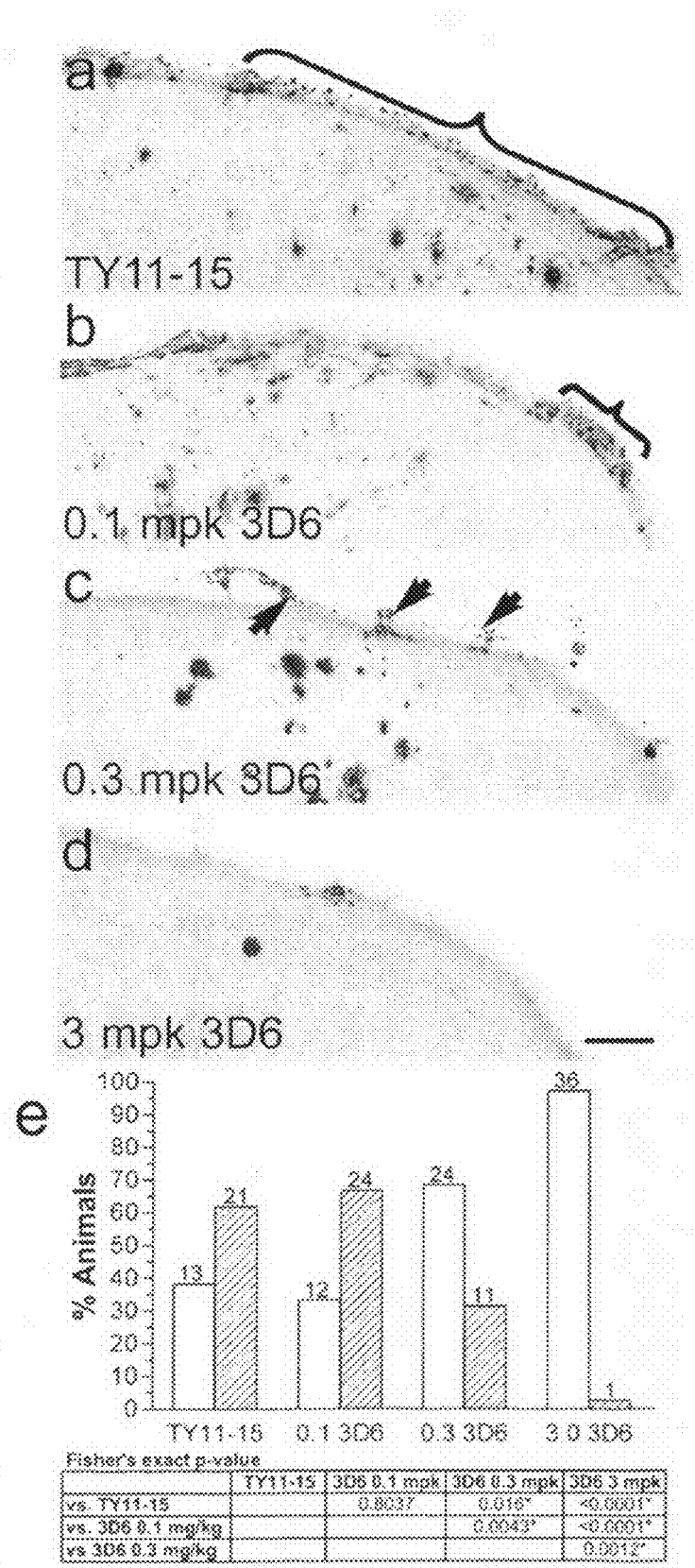
FIG. 3a shows control-treated brain.
FIG. 3b shows 0.1 mg/kg 3D6-treated brain.
FIG. 3c shows 0.3 mg/kg 3D6-treated brain.
FIG. 3d shows 3 mg/kg 3D6-treated brain with 3D6 immunolabeling of VAβ in leptomeningeal vessels. Brackets and arrows, VAβ, Scale bars=100 μm.
Figure 4:
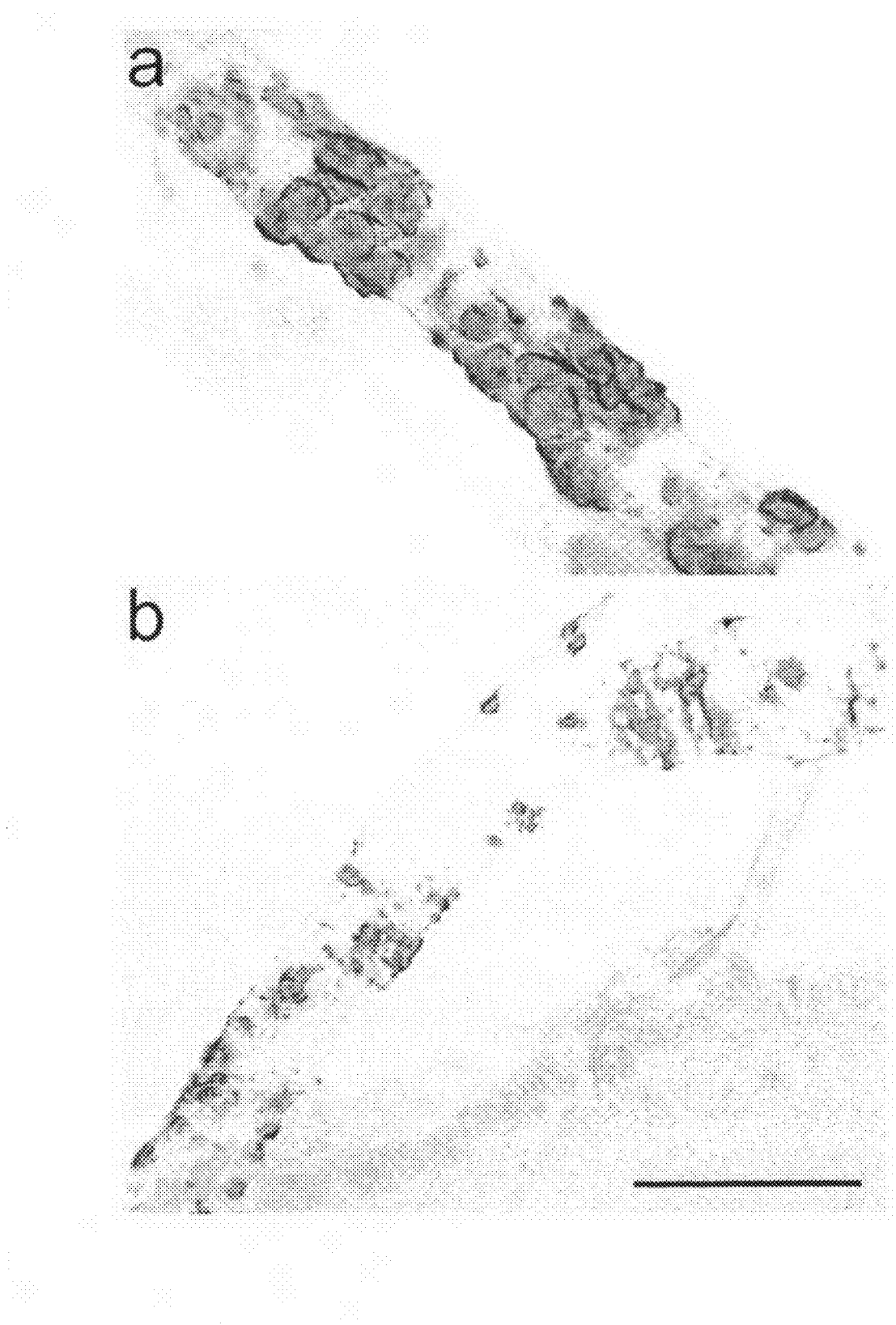
FIG. 4a shows 3D6 immunolabeling of rounded masses and bands of intact VAβ encompassing an unaffected leptomeningeal vessel in a 0.1 mg/kg 3D6-treated mouse.
FIG. 4b shows 3D6 immunolabeling of patchy, eroded VAβ during partial clearance in a 0.1 mg/kg 3D6-treated mouse. Scale bar=50 μm.

In the 3D6 dose-response study (Study B, FIG. 3*a-d*), VAβ was again significantly cleared or prevented by 3D6 treatment at the 3.0 mg/kg 3D6 dose level compared to treatment with the TY11-15 control (p<0.001). There was also clearance or prevention of VAβ at the intermediate dose level (0.3 mg/kg) vs. control (p=0.016). There was no difference between the 0.1 mg/kg dose group and the TY11-15 control group (p=0.8037). FET p-values<0.025 are statistically significant, using the Hochberg method of multiple comparisons. Although the number of vessels was not significantly different, partial clearance of amyloid was observed from vessels in this group at the microscopic level (FIG. 4*a, b*). While intact Aβ forms masses and bands that encompass an unaffected leptomeningeal vessel as shown in FIG. 4*a*, VAβ has a patchy, eroded appearance during partial clearance (FIG. 4*b*). This morphology is not seen in untreated mice.

Figure 2:
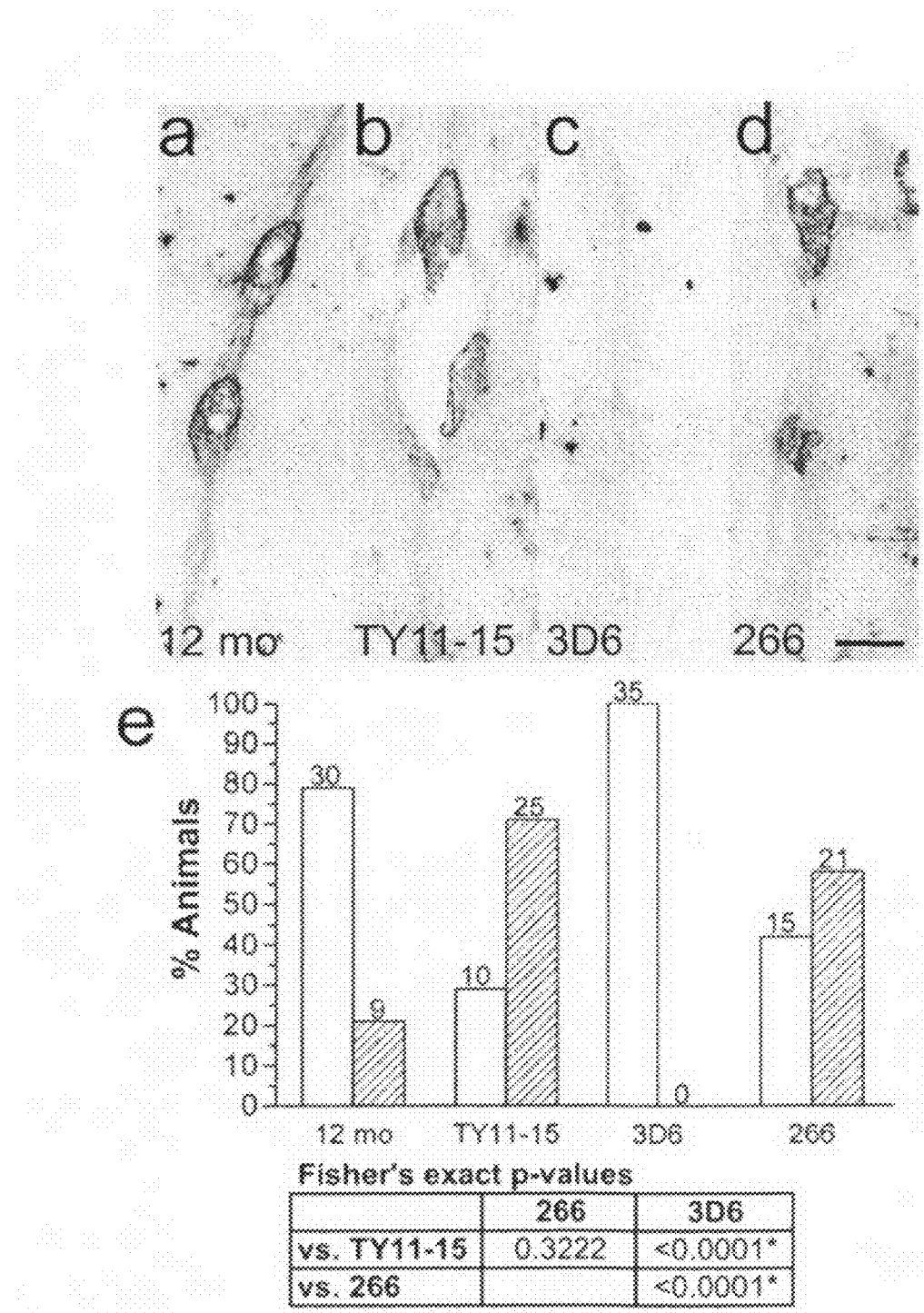
FIG. 2a shows untreated 12-month-old mouse brain.
FIG. 2b shows control-treated mouse brain.
FIG. 2c shows 3 mg/kg 3D6-treated mouse brain.
FIG. 2d shows 3 mg/kg 266-treated mouse brain with 3D6 immunolabeling of VAβ in midline vessels. Scale bar=50 μm.
FIG. 2e is a graph which shows the percentage of animals in each group with none-little VAβ (white bars) and moderate VAβ (cross-hatched bars).
FIG. 2f is a graph which shows the percentage of animals in each group with none-little VAβ (white bars) and moderate VAβ (cross-hatched bars).
Figure 5:
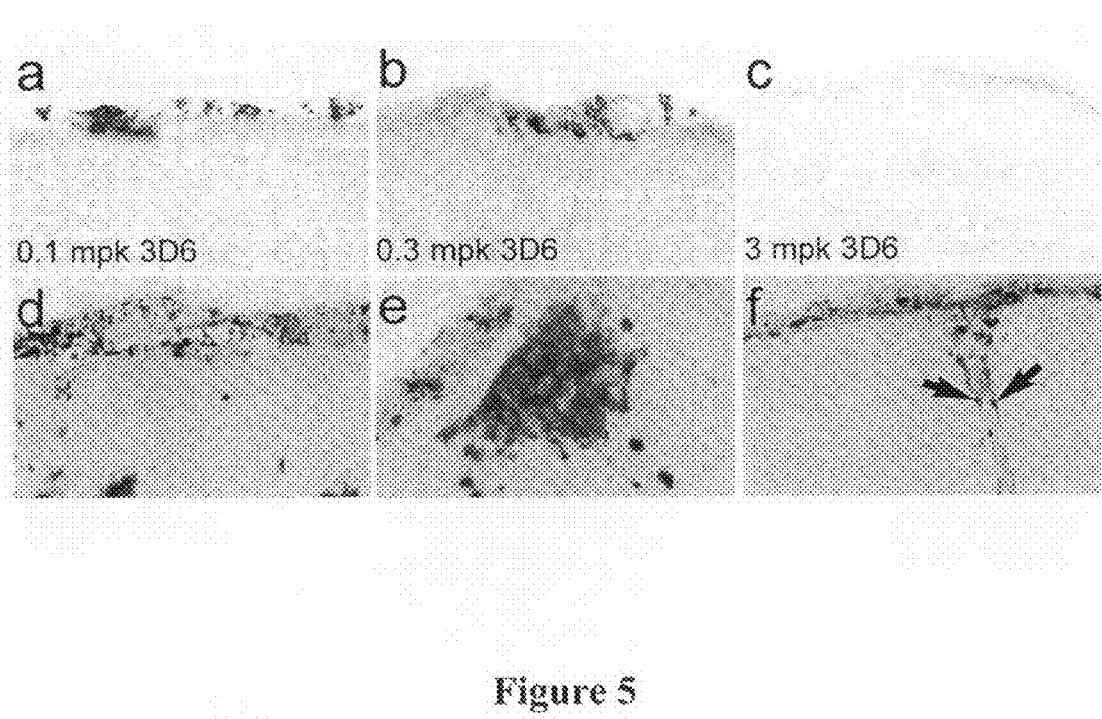
FIGS. 5a and 5b show partial clearance or prevention of VAβ at lower doses of 3D6 with no evidence of microhemorrhage in most animals.
FIG. 5c shows complete clearance or prevention of VAβ at 3 mg/kg 3D6 with no evidence of microhemorrhage in most animals.
FIGS. 5d and 5e show microhemorrhage at sites of partial clearance at lower doses of 3D6.
FIG. 5f shows microhemorrhage at sites of complete clearance at 3 mg/kg 3D6. Arrows, macrophages. Scale bar=100 μm.

Hemosiderin rating. In order to distinguish the subtle differences among treatment groups, a hemosiderin rating scale was developed that reflects the range of staining densities found within this study. Hemosiderin staining, indicative of microhemorrhage, was limited and confined to the structural boundaries of the vasculature without spread into the surrounding parenchyma. Focal hemosiderin deposits were found in vessels of the leptomeninges of the cortex (FIG. 5*a-f*) and the hippocampal thalamic interface, the sagittal sinus vessels at the medial cortex, a few parenchymal vessels at right angles and connected to the leptomeningeal vessels. Hemosiderin was usually concentrated within macrophage-like cells in these areas. The foci of hemosiderin were often associated with altered VAβ morphology: instead of the characteristic distinct bands and scales of VAβ deposition (e.g., FIG. 4*a*), the amyloid had an unusual patchy, degraded appearance (e.g., FIG. 4*b*) or was completely absent. These features were particularly notable in the leptomeningeal (FIG. 5) and sagittal sinus vessels, which often displayed well-developed VAβ morphology in the TY11-15 control groups and untreated mice (FIGS. 2 and 3).

Figure 6:
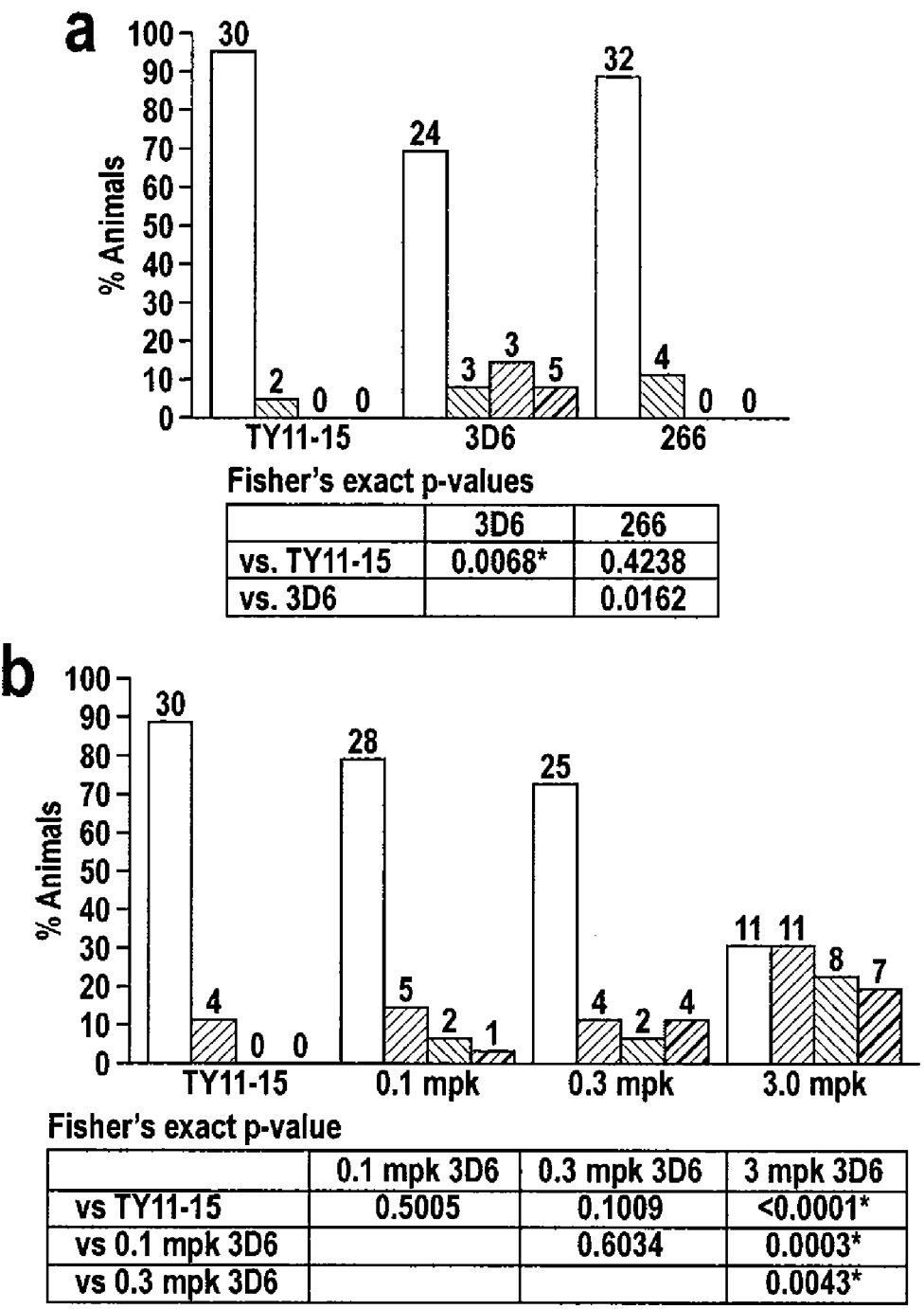
FIG. 6a shows hemosiderin ratings of control and treatment groups in Study A.
FIG. 6b shows hemosiderin ratings of control and treatment groups in Study B.

Hemosiderin staining was predominantly absent or mild in all treatment groups, with the majority of animals across groups having scores of 0 or 1 (FIG. 6). Scores in the 3D6 3 mg/kg treatment groups of both studies were significantly higher, indicating that these were more likely than the control to have hemosiderin scores greater than 0. In Study A, the distributions of hemosiderin scores were similar in the TY11-15 and 266 groups indicating that treatment with 266 antibody was not likely to increase hemosiderin scores. In Study B, the incidence of microhemorrhage was shown to be mitigated by dose. No significant differences were found between the TY11-15 control group and the 0.1 mg/kg 3D6 and 0.3 mg/kg 3D6 groups, indicating that the low and intermediate doses were not likely to increase hemosiderin ratings beyond baseline levels. These differed from the 3.0 mg/kg group, which, again, significantly differed from controls. Compared to Study A, the higher hemosiderin scores in the 3.0 mg/kg group could be due to differences in antibody exposure levels over time and slightly higher baseline levels in the cohort as scores were slightly elevated in the control group.

Association of VAβ clearance and microhemorrhage. Significant clearance or prevention of vascular amyloid was observed in the 0.3 mg/kg and 3.0 mg/kg groups in both studies. The majority of animals in these groups had hemosiderin scores of 0 or 1, indicating that most brains with reduced VAβ had little or no evidence of microhemorrhage. Several examples of hemosiderin-negative vessels with unusually sparse VAβ and an eroded appearance were found in all of the treatment groups (e.g., FIG. 4*b*); these may be vessels in which amyloid was being cleared in the absence of microhemorrhage. When hemosiderin staining was seen in 0.1 mg/kg 3D6-treated animals (FIG. 5*d*), it was typically accompanied a patchy, perivascular distribution of amyloid, possibly indicative of clearance in progress. These perivascular patches of amyloid occurred at sites of vessel-associated hemosiderin labeling within the cortical meninges, parenchyma, and the sagittal sinus vessels. Hemosiderin staining in the 0.3 mg/kg 3D6-treated animals also accompanied a patchy, perivascular distribution of amyloid (FIG. 5e). The amyloid morphology was similar to that in the 0.1 mg/kg 3D6-treated animals, but amyloid was less abundant, and some hemosiderin-positive vessels were cleared of amyloid. Both complete and partial amyloid removal were observed at sites of vessel-associated hemosiderin staining, including the cortical meninges and parenchyma. In contrast, hemosiderin-positive vessels in the 3 mg/kg 3D6-treated animals were often completely devoid of amyloid (FIG. 5f). This feature was never observed in untreated mice and likely illustrates a residual hemosiderin "footprint" that occurred in a subset of vessels with complete VAβ removal. Another feature in these areas was the presence of cells that have phagocytosed hemosiderin (FIG. 5f). These macrophage-like cells were not immunoreactive for Aβ and therefore appear to be a separate population from the microglia and macrophages that remove plaque-associated amyloid.

Discussion

CAA has been identified as an independent risk factor for cognitive impairment and is associated with significant pathologies such as hemorrhage and ischemic damage (see S. M. Greenberg et al., Stroke 35, 2616-9 (2004)). In typical cases, progressive CAA leads to the destruction of smooth muscle cells in the meningeal and parenchymal vasculature, presumably leading to tonal impairment and compromise of both perfusion and perivascular clearance systems (see R. Christie et al., Am J Pathol 158, 1065-71 (2001), S. D. Preston et al., Neuropathol Appl Neurobiol 29, 106-17 (2003)). We show here for the first time evidence of the near-complete clearance or prevention of VAβ by an N-terminal-specific Aβ antibody (3D6) in a chronic immunotherapeutic treatment paradigm with peripherally administered antibody. Although an understanding of mechanism is not required for practice of the invention, the effect was likely dependent on the ability to robustly bind deposited amyloid, since a mid-region Aβ antibody (266), which binds deposited Aβ in vivo much less avidly, showed no evidence of clearing or preventing VAβ. Although a growing body of evidence suggests that the formation and composition of vascular amyloid may differ from that of parenchymal plaques (see M. C. Herzig et al., Nat Neurosci 7, 954-60 (2004)), antibody 3D6 is competent to clear both forms and thus has a broad spectrum of amyloid-reducing activity.

Previous studies investigating the effects of Aβ immunotherapy and brain microvasculature in APP transgenic mice have reported an increased incidence of microhemorrhage. However, a clear cause-and-effect relationship between VAβ and microhemorrhage has not been described. In this report we showed that the majority of deposited vascular amyloid was cleared without inducing microhemorrhage and augmented earlier observations by demonstrating that the incidence of microhemorrhage was associated with VAβ removal. Moreover, the limited areas with microhemorrhages were focally restricted to the architectural boundaries of the vasculature that did not involve the parenchyma. These were associated with either partial or complete removal of VAβ. Importantly, microhemorrhage could be significantly mitigated by modulating the antibody dose within ranges that still effectively cleared parenchymal amyloid plaques.

Racke and colleagues (see M. M. Racke et al., supra) reported the infrequent occurrence of microhemorrhage in PDAPP mice following a significantly larger dose of 3D6 after a 6-week treatment period. Notably, the extent of the reported microhemorrhage was also larger than any observed incidence in the current study, in keeping with our findings of a positive correlation between antibody dose and microhemorrhage scores. Our observations agree with their findings regarding the inability of 266 to bind deposited amyloid or induce microhemorrhage and extend these findings to show that 266 is also not able to clear VAβ.

In APP transgenic mice with very severe VAβ pathology (APP23 mice) cerebral hemorrhage occurs spontaneously and, similarly to human patients, likely is a result of derangement and loss of smooth muscle cells and other destructive consequences of Aβ-related toxicity (see R. Christie et al., supra). Passive immunization of APP23 mice using an N-terminal region Aβ antibody initially exacerbated the incidence and extent of the baseline hemorrhage (see M. Pfeifer et al., Science 298, 1379 (2002)). However, subsequent ultrastructural studies could not find structural differences in the vasculature of treated and non-immunized control (see G. J. Burbach et al., supra). The conclusion was that immunotherapy did not lead to or exacerbate overt damage to the vascular wall, despite the severity of the baseline VAβ pathology. The present study differs from the previous report by examining a model with little spontaneous microhemorrhage and in which Aβ and hemosiderin were co-labeled. We documented the co-localization of Aβ removal and microhemorrhage and found that focal microhemorrhage occurred only in a subset of vessels being cleared of amyloid. Since our quantitation method did not distinguish between partially cleared and intact VAβ, the absolute degree of clearance was likely underestimated.

The relationship between clearance of parenchymal and vascular amyloid is not entirely understood. However, recent reports indicate a co-modulatory relationship likely exists between the two pathologies which may be further clarified in the context of plaque removal (see D. M. Wilcock et al, supra; M. C. Herzig et al., supra; J. A. Nicoll et al., J Neuropathol Exp Neurol 65, 1040-8 (2006)). For example, breeding mutant APP mice with heavy VAβ to those with heavy parenchymal plaque loads actually decreases VAβ, suggesting that plaques can provide a template for Aβ that would otherwise deposit onto the vasculature (see M. C. Herzig et al., supra). Conversely, Wilcock and colleagues (see D. M. Wilcock et al, supra) showed an increase in both VAβ during the course of parenchymal plaque removal in a passive immunization paradigm, suggesting Aβ displacement from parenchymal to vascular compartments may occur during the course of immunotherapy.

In the current study we demonstrate that VAβ can be nearly completely cleared or prevented following passive immunization, which is accompanied by an increased incidence of microhemorrhage that could be diminished by antibody dosage. Aβ patients and APP transgenic mouse models of Aβ both show increased incidence of microhemorrhage associated with the progression of VAβ. The microhemorrhage described here could potentially be explained by an increase in VAβ during the period of clearance of parenchymal plaques as described by Wilcock (see D. M. Wilcock et al, supra), which in the present model would be expected to be transient, since VAβ was ultimately cleared by the termination of the study. Alternatively, in the Wilcock study, a different mouse model and antibody was used, thus the VAβ changes may reflect a fundamental mechanistic difference in regards to different antibody epitopes and animal models. In any event, it seems likely that the eventual cumulative incidence of microhemorrhage may actually be lower following 3D6 treatment, assuming that the removal of existing VAβ and prevention of further deposition will have a prophylactic effect towards further microhemorrhage associated with progressive VAβ. In other words, both treatment-related VAβ and VAβ-contingent microhemorrhage might be transient phenomena that would not persist after VAβ is ultimately removed. Taken together, findings from preclinical models indicate that mechanisms associated with the formation and clearance of VAβ warrant further study. Importantly, a recent study has shown that immunization with full length Aβ peptide in TG 2576 mice actually improves the integrity of the blood brain barrier (i.e. reduced the permeability of Evan's blue), suggesting that these multiple factors might in fact have a positive impact on the vasculature (see D. L. Dickstein et al., supra). It should be noted the immunization with the total Aβ peptide results in antibodies directed primarily to the N terminus similar to the epitope of 3D6.

About 80% of Aβ patients are affected by at least mild CAA, with clinically detrimental consequences of hemorrhage, white matter degeneration, ischemia and inflammation (see S. M. Greenberg et al., supra). The findings from our study provide evidence that Aβ immunotherapy can potentially reverse or prevent the progression of a significant vascular pathology for which there is currently no treatment and further extend the potential therapeutic benefits of anti-Aβ immunotherapy.

Example 2

The effects of structural changes induced by amyloid on smooth muscle cells (SMC) and extracellular matrix (ECM) of PDAPP mouse vessels and the effects of passive immunization on SMC and ECM of PDAPP mouse vessels were examined.
Materials and Methods Mice were immunized weekly for either 3 or 9 months with 1 or 3 mg/Kg of 3D6 antibody. High-resolution, quantitative immunohistochemical (IHC) analyses of vascular components (α-actin for SMC and collagen-IV for ECM) were performed on meningeal vessels from the sagittal sinus, where VAβ deposition is prominent (~70% of vessels affected). Microhemorrhage events were monitored by hemosiderin detection or ferritin immunohistochemistry.
Results In the current study we demonstrate that changes in the vascular wall are invariably associated with VAβ, and they included both degeneration (decreased thickness) and hyperplasia/hypertrophy (increased thickness) of SMC and ECM. These two contrasting findings were often observed in the same vessel and were not present in wild type animals or PDAPP vessels lacking amyloid. The extreme degrees of thickening and thinning of the SM resulted in a widely variable vascular phenotype in untreated PDAPP mice.

Passive immunotherapy restored the pattern of vascular SMC and ECM thicknesses and reduced the phenotypic variability in a dose- and time-dependent manner, with the high dose of 3D6 reaching control levels (wild type) at 9 months (p>0.05). Although the incidence of microhemorrhage increased in the 3-month group, it reduced to control levels after 9 months of treatment (p>0.05). Our results suggest that passive immunotherapy allows the recovery of meningeal vessels from amyloid-induced structural changes. Furthermore, the treatment-related increase in microhemorrhage appears to be a transient event that resolves during VAβ clearance. Mechanisms of repair may be triggered by VAβ removal, which ultimately lead to recovery from vascular dysfunction.

Example 3

Figure 7:
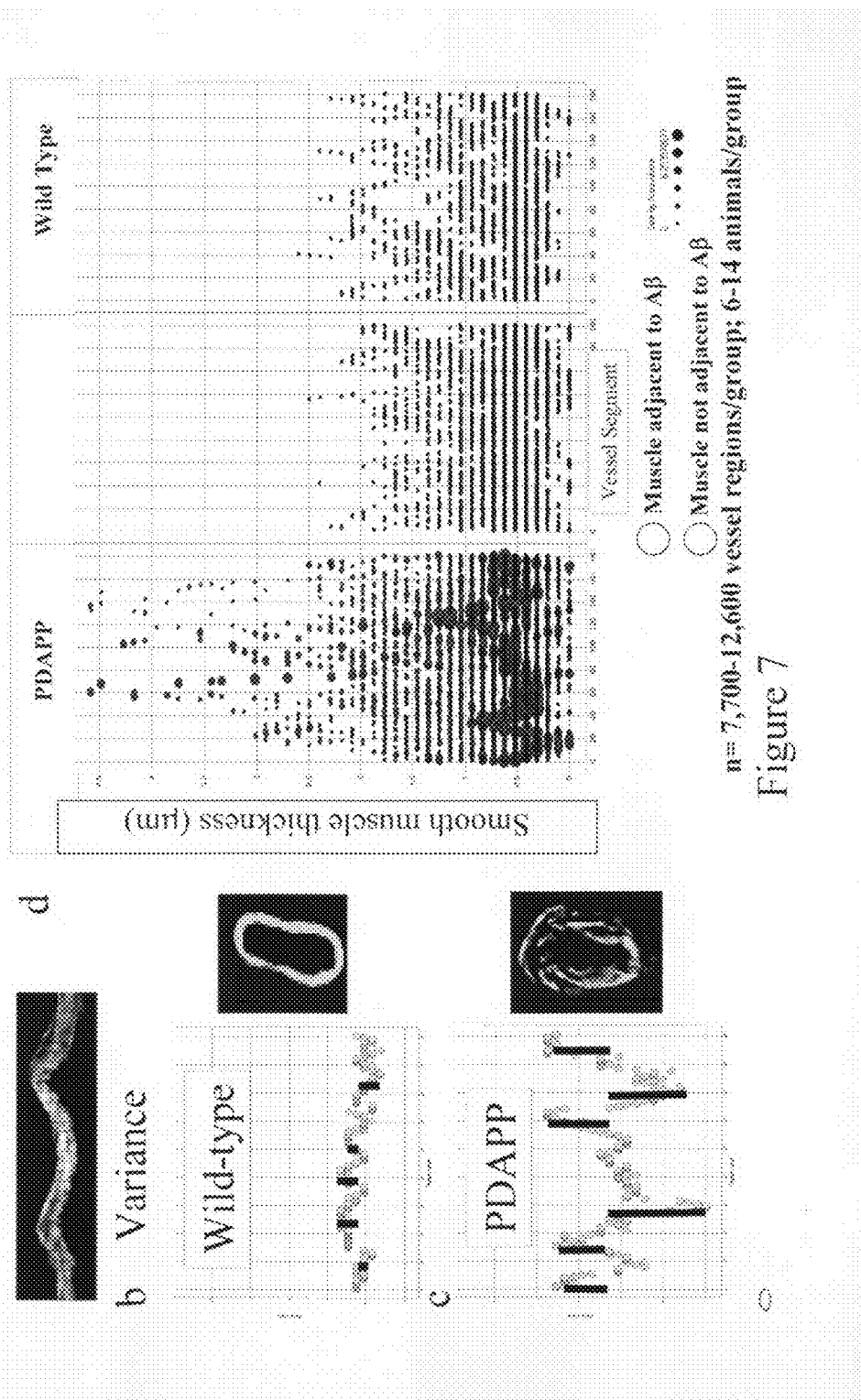
FIG. 7 shows increased variation in vascular smooth muscle thickness associated with Aβ deposition.
Figure 8:
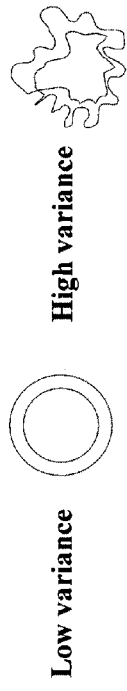
FIG. 8a shows the mean smooth muscle thickness (percent of control) of treatment groups and wild type mice.
FIG. 8b shows the variance of smooth muscle thickness (percent of control) of treatment groups and wild type mice.
Figure 8:
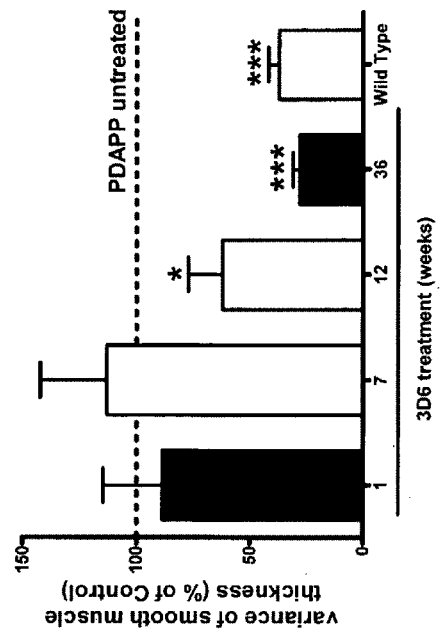
Figure 8:
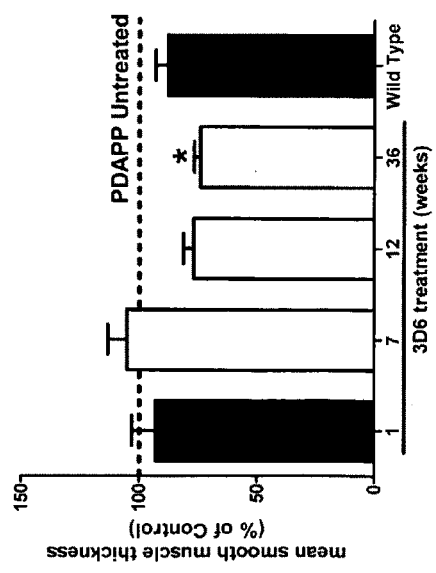
Figure 9:
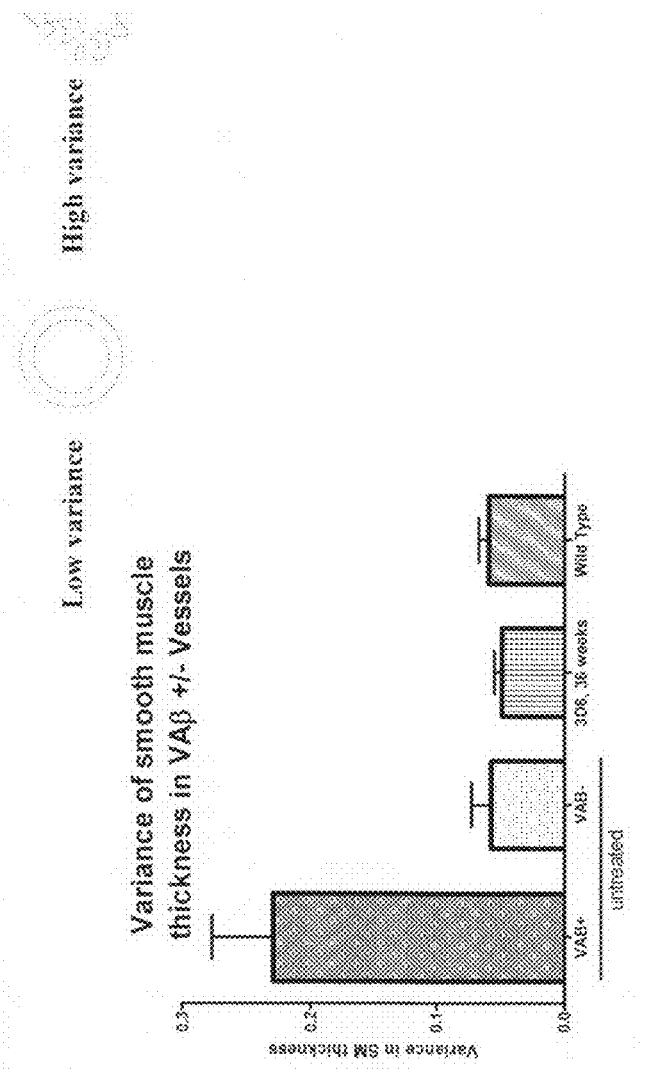
FIG. 9 shows increased variation in vascular smooth muscle thickness is associated with VAβ deposition.
Figure 10:
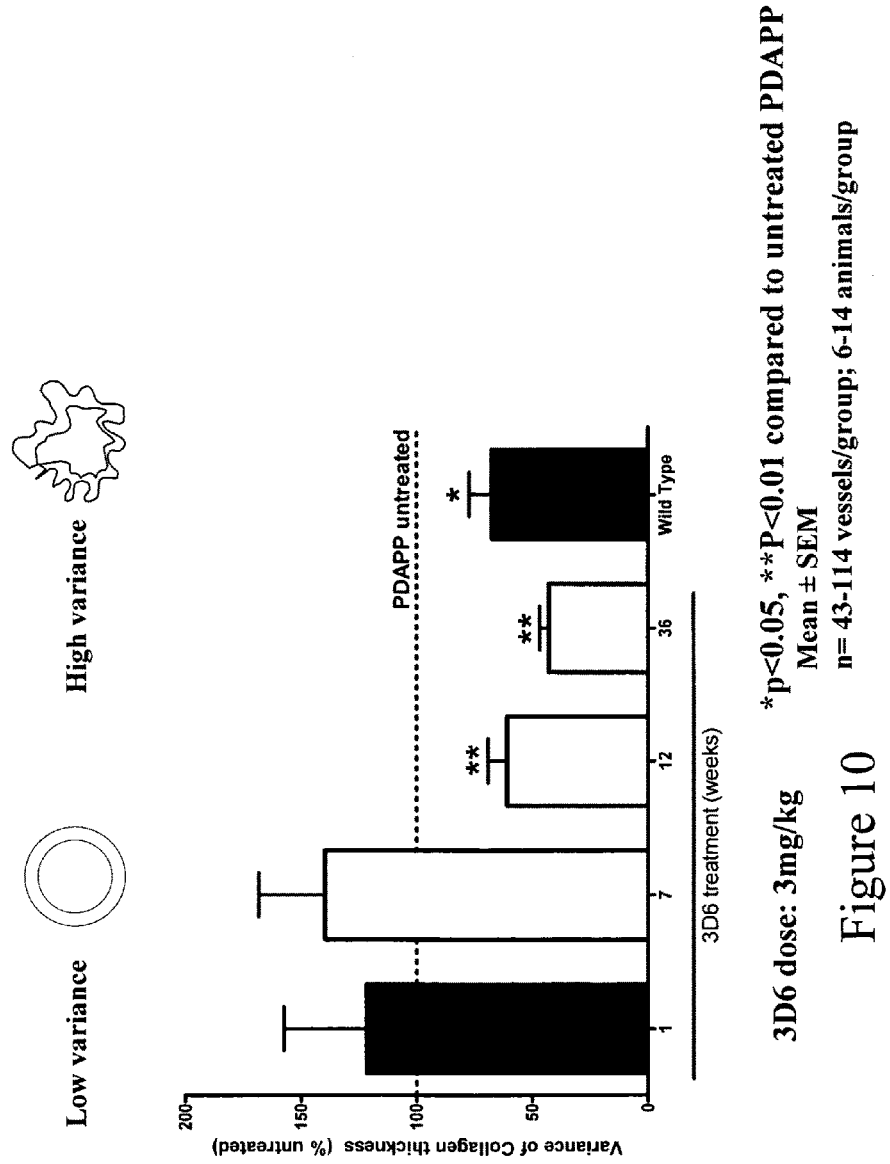
FIG. 10 shows the variance of collagen (percent of untreated mice) of treatment group and wild type mice.

Evidence of vascular recovery after removal of vascular Aβ by passive immunotherapy in PDAPP mice.
Materials and Methods Mice were immunized weekly for either 3 or 9 months with 1 or 3 mg/Kg of 3D6 antibody. High-resolution, quantitative IHC analyses of vascular components (alpha-actin for smooth muscle cells (SMC) and collagen-IV for extracellular matrix (ECM)) were performed on meningeal vessels from the sagittal sinus, where VAβ deposition is prominent (approximately 70% of vessels affected). The parameters measured included vessel layer thickness, vessel size, luminal perimeter, intensity, relative position of vessel elements, and area of brain. Microhemorrhage events were monitored by hemosiderin detection or ferritin immunohistochemistry.
Results In the current study we characterized structural changes induced by amyloid on SMC and ECM of PDAPP mouse vessels and assessed the effects of passive immunotherapy. We demonstrate that changes in the vascular wall are invariably associated with VAβ, and they included both degeneration (decreased thickness) and hyperplasia/hypertrophy (increased thickness) of SMC and ECM. These two contrasting findings were often observed in the same vessel and were not present in wild type animals or PDAPP vessels lacking amyloid. The extreme degrees of thickening and thinning of the SM resulted in a widely variable vascular phenotype in untreated PDAPP mice. Passive immunotherapy restored the pattern of vascular SMC and ECM thicknesses and reduced the phenotypic variability in a dose- and time-dependent manner, with mice treated with the high dose of 3D6 improving to control levels (wild type) at 9 months (p>0.05). In this example, the phenotype of vascular muscle wall was restored to wild type after amyloid removal. FIG. 7a shows the regions where a vessel is sectioned. FIG. 7b shows a vessel plot for wild type mice. FIG. 7c shows a vessel plot for untreated PDAP mice. FIG. 7d shows smooth muscle thickness (μm) for vessel sements of untreated PDAPP mice, treated PDAPP mice and wild type mice. FIG. 8a shows the mean smooth muscle thickness (percent of control) of PDAPP mice treated with 3D6 after one, seven, twelve, and 36 weeks of treatment and of wild type mice. FIG. 8b shows the variance of smooth muscle thickness (percent of control) of PDAPP mice treated with 3D6 after one, seven, twelve, and 36 weeks of treatment and of wild type mice. The phenotype of vascular muscle elastic layers was restored to wild type after amyloid removal. Increased variation in vascular smooth muscle thickness was associated with VAβ deposition. FIG. 9 shows the variance of smooth muscle VAβ+/−vessels, 36 week treatment group and wild type mice. FIG. 10 shows the variance of collagen (percent of untreated mice) of PDAPP mice treated with 3D6 after one, seven, twelve, and 36 weeks of treatment and of wild type mice. Although the incidence of microhemorrhage increased in the 3-month group, it was reduced to control levels after 9 months of treatment (p>0.05). Our results indicate that passive immunotherapy allows the recovery of meningeal vessels from amyloid-induced structural changes. Furthermore, the treatment-related increase in microhemorrhage appears to be a transient event that resolves during VAβ clearance. Mechanisms of repair may be triggered by VAβ removal, which ultimately lead to recovery from vascular dysfunction.

The current study demonstrated that vascular Aβ deposition causes structural changes in smooth muscle and elastic components resulting in a widely variable vascular phenotype in PDAPP mice. Passive immunotherapy with an antibody that is specific for the N-terminus of Aβ restores normal vascular phenotype in a time-dependent manner.

Although the foregoing invention has been described in detail for purposes of clarity of understanding, it will be obvious that certain modifications may be practiced within the scope of the appended claims. All publications and patent documents cited herein, as well as text appearing in the figures, are hereby incorporated by reference in their entirety for all purposes to the same extent as if each were so individually denoted.

What is claimed is:

1. A method of restoring cerebral vascular phenotype in a patient suffering from vascular Aβ deposits, comprising administering an antibody that is specific for Aβ in a treatment regime associated with efficacious vascular amyloid removal, wherein the administration of the antibody restores cerebral vascular phenotype, wherein the antibody binds to an epitope within residues 1-10 of Aβ and the antibody is administered intravenously at a quarterly frequency at a dose of 0.5-1.5 mg/kg, or monthly at a dose of 0.1-1 mg/kg, or is administered subcutaneously at a frequency between weekly and monthly at a dose of between 0.01 mg/kg to 0.35 mg/kg and the antibody is administered at least for a year.

2. The method of claim 1, wherein the antibody binds within residues 1-5 of Aβ.

3. The method of claim 1, wherein the antibody is a humanized, human, or chimeric antibody.

4. The method of claim 3, wherein the antibody is humanized 3D6 or humanized 12A11.

5. The method of claim 4, wherein the humanized 3D6 antibody is bapineuzumab.

6. The method of any one of claims 1 and 2, 5, further comprising monitoring cerebral vascular phenotype.

7. The method of claim 6, wherein the monitoring comprises quantification of vascular elements along the vessel perimeter.

8. The method of claim 7, wherein the vascular elements are selected from the group consisting of vessel layer thickness, vessel size, luminal perimeter, intensity, and the relative position of vessel elements.

9. A method of restoring cerebral vascular meningeal vessel phenotype from structural damage from amyloid induced structural changes comprising:
monitoring for amyloid induced structural changes involving degeneration and hyperplasia/hypertrophy of smooth muscle cells and extracellular matrix in the vessel walls, and
subcutaneously or intravenously administering an antibody that is specific for Aβ in a treatment regime associated with efficacious vascular amyloid removal, wherein the administration of the antibody restores vessels to normal phenotype; wherein the antibody binds to an epitope within residues 1-10 of Aβ.

10. The method of claim 9, wherein the antibody binds within residues 1-5 of Aβ.

11. The method of claim 9, wherein the antibody is a humanized, human, or chimeric antibody.

12. The method of claim 11, wherein the antibody is humanized 3D6 or humanized 12A11.

13. The method of claim 12, wherein the humanized 3D6 antibody is bapineuzumab.

* * * * *

UNITED STATES PATENT AND TRADEMARK OFFICE
CERTIFICATE OF CORRECTION

| | | |
|---|---|---|
| PATENT NO. | : 8,003,097 B2 | Page 1 of 1 |
| APPLICATION NO. | : 12/181238 | |
| DATED | : August 23, 2011 | |
| INVENTOR(S) | : Sally Schroeter et al. | |

It is certified that error appears in the above-identified patent and that said Letters Patent is hereby corrected as shown below:

Col. 97, line 43

In line 1 of claim 6, delete "2, 5" and insert -- 2-5 --

Signed and Sealed this
Fourth Day of October, 2011

David J. Kappos
*Director of the United States Patent and Trademark Office*